US010119124B2

(12) United States Patent  
Watanabe et al.

(10) Patent No.: US 10,119,124 B2  
(45) Date of Patent: *Nov. 6, 2018

(54) INFLUENZA M2 PROTEIN MUTANT VIRUSES AS LIVE INFLUENZA ATTENUATED VACCINES

(71) Applicant: Wisconsin Alumni Research Foundation (WARF), Madison, WI (US)

(72) Inventors: Tokiko Watanabe, Tokyo (JP); Yoshihiro Kawaoka, Middleton, WI (US)

(73) Assignee: Wisconsin Alumni Research Foundation (WARF), Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 15/292,595

(22) Filed: Oct. 13, 2016

(65) Prior Publication Data

US 2017/0096645 A1  Apr. 6, 2017

Related U.S. Application Data

(63) Continuation of application No. 12/214,414, filed on Jun. 18, 2008, now Pat. No. 9,474,798.

(60) Provisional application No. 60/944,680, filed on Jun. 18, 2007.

(51) Int. Cl.
| | | |
|---|---|---|
| *C12N 7/00* | (2006.01) | |
| *A61K 39/145* | (2006.01) | |
| *A61K 39/00* | (2006.01) | |

(52) U.S. Cl.
CPC .............. *C12N 7/00* (2013.01); *A61K 39/145* (2013.01); *A61K 2039/5254* (2013.01); *C12N 2760/16121* (2013.01); *C12N 2760/16134* (2013.01)

(58) Field of Classification Search
CPC ............ A61K 39/12; A61K 2039/5258; A61K 39/145; A61K 2039/53; A61K 39/42; A61K 2039/5254; A61K 2039/6075; C07K 14/005; C07K 16/1018; C12N 7/00; C12N 15/86; C12N 2760/16123; C12N 2760/16151; C12N 2760/16222; C12N 2760/16121; C12N 2760/16122; C12N 2760/16134; C12N 2760/16161
See application file for complete search history.

(56) References Cited

U.S. PATENT DOCUMENTS

| | | | |
|---|---|---|---|
| 4,071,618 A | 1/1978 | Konobe et al. | |
| 4,659,569 A | 4/1987 | Mitsuhashi et al. | |
| 5,166,057 A | 11/1992 | Palese et al. | |
| 5,716,821 A | 2/1998 | Wertz et al. | |
| 5,789,229 A | 8/1998 | Wertz et al. | |
| 5,820,871 A | 10/1998 | Palese et al. | |
| 5,840,520 A | 11/1998 | Clarke et al. | |
| 5,854,037 A | 12/1998 | Palese et al. | |
| 5,948,410 A | 9/1999 | Van Scharrenburg et al. | |
| 5,994,526 A | 11/1999 | Meulewaeter et al. | |
| 6,033,886 A | 3/2000 | Conzelmann | |
| 6,037,348 A | 3/2000 | Colacino et al. | |
| 6,146,642 A | 11/2000 | Garcia-Sastre et al. | |
| 6,169,175 B1 | 1/2001 | Frace et al. | |
| 6,194,546 B1 | 2/2001 | Newton et al. | |
| 6,455,298 B1 | 9/2002 | Groner et al. | |
| 6,544,785 B1 | 4/2003 | Palese et al. | |
| 6,656,720 B2 | 12/2003 | Groner et al. | |
| 6,825,036 B2 | 11/2004 | Makizumi et al. | |
| 6,872,395 B2 | 3/2005 | Kawaoka | |
| 6,951,752 B2 | 10/2005 | Reiter et al. | |
| 6,951,754 B2 | 10/2005 | Hoffmann | |
| 6,974,695 B2 | 12/2005 | Vogels et al. | |
| 7,037,707 B2 | 5/2006 | Webster et al. | |
| 7,176,021 B2 | 2/2007 | Kawaoka | |
| 7,226,774 B2 | 6/2007 | Kawaoka | |
| 7,312,064 B2 | 12/2007 | Hoffmann | |
| 7,507,411 B2 | 3/2009 | Zhou et al. | |
| 7,566,458 B2 | 7/2009 | Yang et al. | |
| 7,585,657 B2 | 9/2009 | Kawaoka | |
| 7,588,769 B2 | 9/2009 | Kawaoka | |
| 7,670,837 B2 | 3/2010 | Schwartz | |
| 7,833,788 B2 | 11/2010 | Pau et al. | |
| 7,883,844 B2 | 2/2011 | Nouchi et al. | |
| 7,955,833 B2 | 6/2011 | Reiter et al. | |
| 7,959,930 B2 | 6/2011 | De Wit et al. | |
| 7,972,843 B2 | 7/2011 | Hoffmann | |
| 7,993,924 B2 | 8/2011 | Billeter et al. | |
| 8,012,736 B2 | 9/2011 | Hoffman et al. | |

(Continued)

FOREIGN PATENT DOCUMENTS

| | | |
|---|---|---|
| AU | 2012204138 B2 | 5/2014 |
| CN | 1826407 B | 9/2013 |

(Continued)

OTHER PUBLICATIONS

FLUMIST™ Package Insert Template, [Online]. Retrieved from the Internet: http://www.fda.gov/downloads/BiologicsBloodVaccines!Vaccines/ApprovedProducts/UCM294307.pdf, (Mar. 1, 2012).

(Continued)

*Primary Examiner* — Rachel B Gill

(74) *Attorney, Agent, or Firm* — Schwegman Lundberg & Woessner, P.A.

(57) ABSTRACT

A method to prepare recombinant influenza viruses comprising a mutant M2 protein which has a deletion of two or more residues in the cytoplasmic tail and is attenuated in vivo, is provided, as well the resulting virus and vaccines with the virus.

20 Claims, 12 Drawing Sheets

Specification includes a Sequence Listing.

(56) References Cited

U.S. PATENT DOCUMENTS

| | | |
|---|---|---|
| 8,048,430 B2 | 11/2011 | Yang et al. |
| 8,057,806 B2 | 11/2011 | Kawaoka et al. |
| 8,093,033 B2 | 1/2012 | Kemble et al. |
| 8,114,415 B2 | 2/2012 | Hoffmann et al. |
| 8,119,337 B2 | 2/2012 | Gregersen |
| 8,119,388 B2 | 2/2012 | Schwartz et al. |
| 8,309,099 B2 | 11/2012 | Hoffmann |
| 8,354,114 B2 | 1/2013 | Lu et al. |
| 8,357,376 B2 | 1/2013 | Liu et al. |
| 8,409,843 B2 | 4/2013 | Kemble et al. |
| 8,460,914 B2 | 6/2013 | Gregersen |
| 8,475,806 B2 | 7/2013 | Kawaoka |
| 8,524,497 B2 | 9/2013 | Reiter et al. |
| 8,546,123 B2 | 10/2013 | Lewis |
| 8,574,591 B2 | 11/2013 | Hoffmann et al. |
| 8,574,593 B2 | 11/2013 | Yang et al. |
| 8,580,277 B2 | 11/2013 | Yang et al. |
| 8,591,914 B2 | 11/2013 | Yang et al. |
| 9,254,318 B2 | 2/2016 | Kawaoka et al. |
| 9,284,533 B2 | 3/2016 | Bilsel et al. |
| 9,474,798 B2 | 10/2016 | Watanabe et al. |
| 9,757,446 B2 | 9/2017 | LeFebvre et al. |
| 9,950,057 B2 | 4/2018 | Kawaoka et al. |
| 2002/0164770 A1 | 11/2002 | Hoffmann |
| 2002/0197705 A1 | 12/2002 | Kawaoka |
| 2003/0035814 A1 | 2/2003 | Kawaoka et al. |
| 2003/0044962 A1 | 3/2003 | Makizumi et al. |
| 2003/0073223 A1 | 4/2003 | Groner et al. |
| 2003/0119183 A1 | 6/2003 | Groner |
| 2003/0194694 A1 | 10/2003 | Kawaoka |
| 2004/0002061 A1 | 1/2004 | Kawaoka |
| 2004/0063141 A1 | 4/2004 | Lok |
| 2004/0077086 A1 | 4/2004 | Reiter et al. |
| 2004/0219170 A1 | 11/2004 | Kawaoka |
| 2005/0003349 A1 | 1/2005 | Kawaoka |
| 2005/0037487 A1 | 2/2005 | Kawaoka et al. |
| 2005/0118140 A1 | 6/2005 | Vorlop et al. |
| 2005/0158342 A1 | 7/2005 | Kemble et al. |
| 2005/0186563 A1 | 8/2005 | Hoffmann |
| 2005/0202553 A1 | 9/2005 | Groner et al. |
| 2005/0232950 A1 | 10/2005 | Kawaoka |
| 2005/0266026 A1 | 12/2005 | Hoffmann et al. |
| 2006/0057116 A1 | 3/2006 | Kawaoka et al. |
| 2006/0166321 A1 | 7/2006 | Kawaoka et al. |
| 2006/0188977 A1 | 8/2006 | Schwartz et al. |
| 2006/0246092 A1 | 11/2006 | Neirynck et al. |
| 2007/0231348 A1 | 10/2007 | Kawaoka et al. |
| 2008/0233560 A1 | 9/2008 | Hoffmann |
| 2008/0254067 A1 | 10/2008 | Trepanier et al. |
| 2008/0274141 A1 | 11/2008 | Groner et al. |
| 2008/0311148 A1 | 12/2008 | Hoffmann |
| 2008/0311149 A1 | 12/2008 | Hoffmann |
| 2009/0074812 A1 | 3/2009 | Watanabe et al. |
| 2009/0081252 A1 | 3/2009 | Gregersen |
| 2009/0181446 A1 | 7/2009 | Nouchi et al. |
| 2010/0112000 A1 | 5/2010 | Schwartz et al. |
| 2010/0183671 A1 | 7/2010 | Gregersen et al. |
| 2010/0247572 A1 | 9/2010 | Kawaoka |
| 2011/0027314 A1 | 2/2011 | Broeker |
| 2011/0045022 A1 | 2/2011 | Tsai |
| 2011/0110978 A1 | 5/2011 | Kawaoka et al. |
| 2011/0236417 A1 | 9/2011 | Watanabe et al. |
| 2012/0020997 A1 | 1/2012 | Hoffman et al. |
| 2012/0034600 A1 | 2/2012 | Gregersen |
| 2012/0115206 A1 | 5/2012 | Schwartz et al. |
| 2012/0156241 A1 | 6/2012 | De Wit et al. |
| 2012/0207785 A1 | 8/2012 | Fabry et al. |
| 2013/0095135 A1 | 4/2013 | Collignon et al. |
| 2013/0183741 A1 | 7/2013 | Park et al. |
| 2013/0316434 A1 | 11/2013 | Reiter et al. |
| 2015/0017205 A1 | 1/2015 | Kawaoka et al. |
| 2016/0208223 A1 | 7/2016 | Kawaoka et al. |
| 2017/0354730 A1 | 12/2017 | Kawaoka et al. |

FOREIGN PATENT DOCUMENTS

| | | |
|---|---|---|
| EP | 0702085 A1 | 3/1996 |
| EP | 1201760 A1 | 5/2002 |
| EP | 2010557 B1 | 2/2014 |
| EP | 1631663 B1 | 8/2016 |
| JP | 2004-500842 A | 1/2004 |
| JP | 2005-523698 A | 8/2005 |
| JP | 2005-245302 A | 9/2005 |
| JP | 2005-535288 A | 11/2005 |
| JP | 2009-532352 A | 9/2009 |
| JP | 4927290 B2 | 2/2012 |
| JP | 2014039551 A | 3/2014 |
| JP | 2014-131516 A | 7/2014 |
| JP | 2016-524915 A | 8/2016 |
| JP | 2016-169225 A | 9/2016 |
| WO | WO-9610631 A1 | 4/1996 |
| WO | WO-9610632 A1 | 4/1996 |
| WO | WO-9640955 A1 | 12/1996 |
| WO | WO-97/37000 A1 | 10/1997 |
| WO | WO-98/02530 A1 | 1/1998 |
| WO | WO-98/53078 A1 | 11/1998 |
| WO | WO-99/28445 A1 | 6/1999 |
| WO | WO-0053786 A1 | 9/2000 |
| WO | WO-0060050 A2 | 10/2000 |
| WO | WO-00/60050 A3 | 1/2001 |
| WO | WO-0179273 A2 | 10/2001 |
| WO | WO-01/83794 A2 | 11/2001 |
| WO | WO-03/068923 A2 | 8/2003 |
| WO | WO-03/076462 A1 | 9/2003 |
| WO | WO-03/091401 A2 | 11/2003 |
| WO | WO-2004094466 A2 | 11/2004 |
| WO | WO-2004/112831 A2 | 12/2004 |
| WO | WO-2004/112831 A3 | 12/2004 |
| WO | WO-2005/062820 A2 | 7/2005 |
| WO | WO-2007/126810 A2 | 11/2007 |
| WO | WO-2007/126810 A3 | 11/2007 |
| WO | WO-2008/156778 A3 | 12/2008 |
| WO | WO-2008156778 A2 | 12/2008 |
| WO | WO-2008156778 A9 | 2/2009 |
| WO | WO-2011/056591 A1 | 5/2011 |
| WO | WO-2012177924 | 12/2012 |
| WO | WO-2015/009743 A1 | 1/2015 |

OTHER PUBLICATIONS

"1.A.32 The Type B Influenza Virus NB Channel (NB-C) Family", Transport Protein Database, (University of California, San Diego, The Sailer Laboratory Bioinformatics Group) [online}. http://www.web.archive.org/web/200301311055254/http://tcdb.ucsd.edu/tcdb/tcfamilybrowse.php?tcname=1.A.32, (Archived Jan. 31, 2003), 1 pg.

"U.S. Appl. No. 09/834,095, Advisory Action dated Jan. 8, 2004", 3 pgs.

"U.S. Appl. No. 09/834,095, Final Office Action dated Aug. 26, 2003", 12 pgs.

"U.S. Appl. No. 09/834,095, Non-Final Office Action dated Nov. 4, 2002", 12 pgs.

"U.S. Appl. No. 09/834,095, Notice of Allowance dated Sep. 27, 2004", 13 pgs.

"U.S. Appl. No. 09/834,095, Office Action dated Apr. 20, 2004", 11 pgs.

"U.S. Appl. No. 09/834,095, Response filed Feb. 4, 2003 to Office Action dated Nov. 4, 2002", 14 pgs.

"U.S. Appl. No. 09/834,095, Response filed Jun. 12, 2003 to Restriction Requirement dated Apr. 22, 2003", 2 pgs.

"U.S. Appl. No. 09/834,095, Response filed Jun. 18, 2004 to Office Action dated Apr. 20, 2004", 11 pgs.

"U.S. Appl. No. 09/834,095, Response filed Aug. 1, 2002 to Restriction Requirement dated Jul. 1, 2002", 3 pgs.

"U.S. Appl. No. 09/834,095, Response filed Nov. 26, 2003 to Final Office Action dated Aug. 26, 2003", 10 pgs.

"U.S. Appl. No. 09/834,095, Restriction Requirement dated Apr. 22, 2003", 5 pgs.

(56) References Cited

OTHER PUBLICATIONS

"U.S. Appl. No. 09/834,095, Restriction Requirement dated Jul. 1, 2002", 9 pgs.
"U.S. Appl. No. 09/834,095, Supplemental Amendment filed Aug. 4, 2004", 7 pgs.
"U.S. Appl. No. 10/827,995, Final Office Action dated Nov. 15, 2006", 10 pgs.
"U.S. Appl. No. 10/827,995, Non-Final Office Action dated Jun. 2, 2006", 15 pgs.
"U.S. Appl. No. 10/827,995, Non-Final Office Action dated Oct. 25, 2007", 7 pgs.
"U.S. Appl. No. 10/827,995, Notice of Allowance dated Feb. 17, 2009", 9 pgs.
"U.S. Appl. No. 10/827,995, Notice of Allowance dated Oct. 17, 2008", 7 pgs.
"U.S. Appl. No. 10/827,995, Notice of Non-Compliant Amendment dated Jul. 25, 2007", 4 pgs.
"U.S. Appl. No. 10/827,995, Proposed Examiner's Amendment dated Jun. 5, 2008", 6 pgs.
"U.S. Appl. No. 10/827,995, Response filed Mar. 3, 2008 to Office Action dated Oct. 25, 2007", 10 pgs.
"U.S. Appl. No. 10/827,995, Response filed May 14, 2007 Final Office Action dated Nov. 15, 2006", 16 pgs.
"U.S. Appl. No. 10/827,995, Response filed Aug. 13, 2007 to Notice of Non-Compliant Amendment dated Jul. 25, 2007", 16 pgs.
"U.S. Appl. No. 10/827,995, Response filed Aug. 17, 2006 Non-Final Office Action dated Jun. 2, 2006", 15 pgs.
"U.S. Appl. No. 11/043,768 Non-Final Office Action dated Sep. 27, 2010", 8 pgs.
"U.S. Appl. No. 11/043,768, Final Office Action dated Jun. 27, 2008", 8 pgs.
"U.S. Appl. No. 11/043,768, Non-Final Office Action dated Feb. 23, 2010", 6 pgs.
"U.S. Appl. No. 11/043,768, Non-Final Office Action dated Feb. 23, 2009", 7 pgs.
"U.S. Appl. No. 11/043,768, Non-Final Office Action dated Nov. 28, 2007", 9 pgs.
"U.S. Appl. No. 11/043,768, Notice of Allowance dated Jun. 29, 2011", 12 pgs.
"U.S. Appl. No. 11/043,768, Response filed May 2, 2011 to Final Office Action dated Feb. 3, 2011", 11 pgs.
"U.S. Appl. No. 11/043,768, Response filed Jun. 15, 2010 to Non Final Office Action dated Feb. 23, 2010", 9 pgs.
"U.S. Appl. No. 11/043,768, Response filed Jun. 23, 2009 to Non-Final Office Action dated Feb. 23, 2009", 9 pgs.
"U.S. Appl. No. 11/043,768, Response filed Sep. 13, 2007 to Restriction Requirement dated Mar. 13, 2007", 10 pgs.
"U.S. Appl. No. 11/043,768, Response filed Oct. 26, 2010 to Non Final Office Action dated Sep. 27, 2010", 11 pgs.
"U.S. Appl. No. 11/043,768, Response filed Dec. 12, 2008 to Final Office Action dated Jun. 27, 2008", 9 pgs.
"U.S. Appl. No. 11/043,768, Response filed Mar. 10, 2008 to Office Action dated Nov. 28, 2007", 12 pgs.
"U.S. Appl. No. 11/043,768, Restriction Requirement dated Mar. 13, 2007", 9 pgs.
"U.S. Appl. No. 11/043,786, Final Office Action dated Feb. 3, 2011", 10 pgs.
"U.S. Appl. No. 12/214,414, Advisory Action dated Feb. 2, 2016", 5 pgs.
"U.S. Appl. No. 12/214,414, Advisory Action dated Apr. 15, 2015", 6 pgs.
"U.S. Appl. No. 12/214,414, Advisory Action dated Oct. 21, 2011", 5 pgs.
"U.S. Appl. No. 12/214,414, Examiner Interview Summary dated Dec. 11, 2015", 3 pgs.
"U.S. Appl. No. 12/214,414, Final Office Action dated Jan. 20, 2015", 28 pgs.
"U.S. Appl. No. 12/214,414, Final Office Action dated Aug. 2, 2011", 7 pgs.
"U.S. Appl. No. 12/214,414, Final Office Action dated Nov. 18, 2015", 17 pgs.
"U.S. Appl. No. 12/214,414, Non Final Office Action dated Jun. 12, 2014", 28 pgs.
"U.S. Appl. No. 12/214,414, Non Final Office Action dated Dec. 10, 2010", 6 pgs.
"U.S. Appl. No. 12/214,414, Non-Final Office Action dated Mar. 2, 2010", 9 pgs.
"U.S. Appl. No. 12/214,414, Notice of Allowance dated Jun. 7, 2016", 18 pgs.
"U.S. Appl. No. 12/214,414, Response filed Jan. 19, 2016 to Final Office Action dated Nov. 18, 2015", 14 pgs.
"U.S. Appl. No. 12/214,414, Response filed Feb. 18, 2016 to Final Office Action dated Nov. 18, 2015", 14 pgs.
"U.S. Appl. No. 12/214,414, Response filed Mar. 26, 2015 to Final Office Action dated Jan. 20, 2015", 13 pgs.
"U.S. Appl. No. 12/214,414, Response filed May 3, 2011 to Non Final Office Action dated Dec. 10, 2010", 12 pgs.
"U.S. Appl. No. 12/214,414, Response filed Jul. 20, 2015 to Advisory Action dated Apr. 15, 2015", 14 pgs.
"U.S. Appl. No. 12/214,414, Response filed Aug. 31, 2010 to Non Final Office Action dated Mar. 2, 2010", 11 pgs.
"U.S. Appl. No. 12/214,414, Response filed Oct. 3, 2011 to Non Final Office Action dated Aug. 2, 2011", 9 pgs.
"U.S. Appl. No. 12/214,414, Response filed Dec. 21, 2011 to Advisory Action dated Oct. 21, 2011", 10 pgs.
"U.S. Appl. No. 12/467,492, Restriction Requirement dated Nov. 22, 2010", 6 pgs.
"U.S. Appl. No. 12/214,414, Response filed Oct. 14, 2014 to Non Final Office Action dated Jun. 12, 2014", 16 pgs.
"Australian Application Serial No. 2001255336, Examiner's First Report dated Feb. 16, 2005", 2 pgs.
"Australian Application Serial No. 2001255336, Response filed Aug. 23, 2005 to Examiner's First Report dated Feb. 16, 2005", 10 pgs.
"Canadian Application Serial No. 2,406,180, Office Action dated Sep. 9, 2008", 5 pgs.
"Canadian Application Serial No. 2,406,180, Office Action dated Nov. 10, 2011", 3 pgs.
"Canadian Application Serial No. 2,406,180, Office action dated Nov. 23, 2009", 3 pgs.
"Canadian Application Serial No. 2,406,180, Office Action dated Dec. 10, 2010", 2 Pgs.
"Canadian Application Serial No. 2,406,180, Response filed Jan. 26, 2009 to Official Action dated Sep. 9, 2008", 22 pgs.
"Canadian Application Serial No. 2,406,180, Response filed May 21, 2010 to Office action dated Nov. 23, 2009", 13 pgs.
"Canadian Application Serial No. 2,406,180, Response filed Jun. 14, 2011 to Office Action dated Dec. 10, 2010", 10 pgs.
"Canadian Application Serial No. 2,522,081, Amendment After Allowance filed Aug. 10, 2012", 3 pgs.
"Canadian Application Serial No. 2,522,081, Office Action dated Jun. 6, 2011", 2 pgs.
"Canadian Application Serial No. 2,522,081, Office Action dated Aug. 30, 2010", 2 pgs.
"Canadian Application Serial No. 2,522,081, Office Action dated Oct. 8, 2009", 6 pgs.
"Canadian Application Serial No. 2,522,081, Response filed Feb. 28, 2011 to Office Action dated Aug. 30, 2010", 10 pgs.
"Canadian Application Serial No. 2,522,081, Response filed Apr. 8, 2010 to Office Action dated Oct. 8, 2009", 30 pgs.
"Canadian Application Serial No. 2,522,081, Response filed Nov. 18, 2011 to Office Action dated Jun. 6, 2011", 11 pgs.
"Canadian Application Serial No. 2406180, Response filed May 7, 2012 to Office Action dated Nov. 10, 2011", 11 pgs.
"Chinese Application Serial No. 200480017037, First Office Action dated May 25, 2007", (w/ English Translation), 10 pgs.
"Chinese Application Serial No. 200480017037, Response filed Oct. 30, 2007 to First Office Action dated May 25, 2007", (w/ English Translation of Claims), 26 pgs.
"Chinese Application Serial No. 200480017037.X, Response filed May 14, 2010 to Third Office Action dated Mar. 1, 2010", (w/ English Translation of Claims), 16 pgs.

(56) References Cited

OTHER PUBLICATIONS

"Chinese Application Serial No. 200480017037.X, Response filed Aug. 4, 2009 to Second Office Action dated Mar. 20, 2009", (w/ English Translation of Amended Claims), 15 pgs.
"Chinese Application Serial No. 200480017037.X, Second Office Action dated Mar. 20, 2009", (English Translation), 7 pgs.
"Chinese Application Serial No. 200480017037.X, Third Office Action dated Mar. 1, 2010", (w/ English Translation), 9 pgs.
"European Application 04750333.9, Communication dated Oct. 12, 2006", 6 pgs.
"European Application 04750333.9, Communication dated Dec. 8, 2006", 4 pgs.
"European Application 04750333.9, Communication dated Apr. 11, 2008", 6 pgs.
"European Application 04750333.9, Response filed Oct. 4, 2007 to Communication dated Dec. 8, 2006", 42 pgs.
"European Application 04750333.9, Response filed Nov. 21, 2006 to Communication dated Oct. 12, 2006", 14 pgs.
"European Application Serial No. 01928486.8 Office Action dated Oct. 1, 2009", 2 pgs.
"European Application Serial No. 01928486.8, Communication dated Aug. 10, 2007", 3 pgs.
"European Application Serial No. 01928486.8, Communication dated Sep. 20, 2005", 4 pgs.
"European Application Serial No. 01928486.8, Office Action dated Feb. 19, 2009", 3 pgs.
"European Application Serial No. 01928486.8, Response filed Aug. 28, 2009 to Communication dated Feb. 19, 2009", 5 pgs.
"European Application Serial No. 01928486.8, Response filed Jan. 21, 2008 to Communication dated Aug. 10, 2007", 11 pgs.
"European Application Serial No. 01928486.8, Response filed Jan. 30, 2006 to Communication dated Sep. 20, 2005", 9 pgs.
"European Application Serial No. 01928486.8, Response filed Dec. 9, 2009 to Office Action dated Oct. 1, 2009", 11 pgs.
"European Application Serial No. 04750333.9, Office Action dated Jan. 22, 2009", 5 pgs.
"European Application Serial No. 04750333.9, Response filed Oct. 21, 2008 to Communication dated Apr. 11, 2008", 15 pgs.
"European Application Serial No. 04750333.9, Response filed Nov. 17, 2009 to Communication dated Jan. 22, 2009", 17 pgs.
"European Application Serial No. 04750333.9, Summons to Attend Oral Proceedings dated Aug. 3, 2011", 13 pgs.
"Evaluation of Medicines for human Use", EMEA/CPMP/BWP/2289/01, London, The European Agency for the Evaluation of Medicinal Products, Committee for Proprietary Medicinal Products (CPMP), (Feb. 20, 2003), 14.
"FLUZONE® Influenza Virus Vaccine", Sanofi Aventis Pasteur, Swiftwater, (Jul. 2005), 12 pgs.
"Indian Application Serial No. 02082/KOLNP/2005, Examination Report dated Mar. 17, 2008", 1 pg.
"Indian Application Serial No. 02082/KOLNP/2005, Examination Report dated Dec. 28, 2007", 1 pg.
"Indian Application Serial No. 02082/KOLNP/2005, First Examination Report dated Jan. 25, 2007", 9 pgs.
"Indian Application Serial No. 02082/KOLNP/2005, Response filed Jan. 22, 2008 to Examination Report dated Dec. 28, 2007", 13 pgs.
"Indian Application Serial No. 02082/KOLNP/2005, Response filed Jun. 10, 2008 to Examination Report dated Mar. 17, 2008", 3 pgs.
"Indian Application Serial No. 02082/KOLNP/2005, Response filed Nov. 19, 2007 to First Examination Report dated Jan. 25, 2007", 26 pgs.
"International Application Serial No. PCT/US01/11963, Amendment filed Sep. 9, 2002 to Written Opinion dated Aug. 7, 2002", 12 pgs.
"International Application Serial No. PCT/US01/11963, International Preliminary Examination Report dated Oct. 15, 2002", 13 pgs.
"International Application Serial No. PCT/US01/11963, International Search Report dated May 7, 2002", 5 pgs.
"International Application Serial No. PCT/US01/11963, Response filed Sep. 9, 2002 to Written Opinion dated Aug. 7, 2002", 12 pgs.
"International Application Serial No. PCT/US01/11963, Written Opinion dated Jun. 14, 2002", 12 pgs.
"International Application Serial No. PCT/US01/11963, Written Opinion dated Aug. 7, 2002", 6 pgs.
"International Application Serial No. PCT/US2004/012050, International Search Report dated Feb. 2, 2005", 8 pgs.
"International Application Serial No. PCT/US2004/012050, Written Opinion dated Feb. 2, 2005", 12 pgs.
"International Application Serial No. PCT/US2008/007582, International Preliminary Report on Patentability dated Jan. 7, 2010", 9 pgs.
"International Application Serial No. PCT/US2008/007582, International Search Report dated Feb. 18, 2009".
"International Application Serial No. PCT/US2008/007582, Written Opinion dated Feb. 18, 2009".
"Israel Application Serial No. 171372, Office Action dated Feb. 21, 2010", (Translation), 2 pgs.
"Israel Application Serial No. 171372, Office Action dated Nov. 6, 2008", (Translation), 12 pgs.
"Israel Application Serial No. 171372, Office Action dated Feb. 20, 2011", (Translation), 2 pgs.
"Israeli Application Serial No. 171372, Response filed Nov. 18, 2010 to Office Action dated Feb. 21, 2010", (Translation), 19 pgs.
"Japanese Application No. 2001-576868, Office Action dated May 31, 2011", (w/ English Translation), 5 pgs.
"Japanese Application No. 2001-576868, Response filed Apr. 26, 2011 to Office Action dated Nov. 2, 2010", (w/ Translation of Amended Claims), 14 pgs.
"Japanese Application Serial No. 2001-576868, Office Action dated Nov. 2, 2010", w/ English Translation), 10 pgs.
"Japanese Application Serial No. 2001-576868, Response filed Dec. 1, 2011 to Office Action dated May 3, 2011", (w/ English Translation of Amended Claims), 37 pgs.
"Japanese Application Serial No. 2006-513125, Office Action dated Mar. 9, 2010", (English Translation), 11 pgs.
"Japanese Application Serial No. 2006-513125, Response filed Aug. 30, 2010 to Office Action dated Mar. 9, 2010", (w/ English Translation of Amended Claims), 60 pgs.
"Japanese Application Serial No. 2011-111048, Office Action dated Jun. 25, 2013", (w/ English Translation), 7 pgs.
"Japanese Application Serial No. 2011-111048, Office Action dated Sep. 18, 2012", (w/ English Translation), 10 pga.
"Japanese Application Serial No. 2011-111048, Response filed Sep. 25, 2012 to Office Action dated Jun. 25, 2013", (w/ English Translation of Amended Claims), 18 pgs.
"Japanese Application Serial No. 2011-111048. Response filed Mar. 15, 2013", (w/ Translation of Amended Claims), 14 pgs.
"Japanese Application Serial No. 2013-198377, Office Action dated Jan. 6, 2015", (w/ English Translation), 9 pgs.
"Japanese Application Serial No. 2006-513125,Final Office Action dated Jan. 18, 2011", (English Translation), 4 pgs.
"Korean Application Serial No. 10-2005-7020077, Response filed Apr. 28, 2008 to Examination Report dated Dec. 28, 2007", (w/ English Translation of Revised Claims), 41 pgs.
"Korean Application Serial No. 10-2005-7020077, Examination Report dated Dec. 28, 2007", (w/ English Translation), 8 pgs.
"Korean Application Serial No. 10-2005-7020077, Notice of Preliminary Rejection dated Jun. 28, 2007", (w/ EnglishTranslation), 9 pgs.
"Korean Application Serial No. 10-2005-7020077, Response filed Aug. 28, 2007 to Notice of Preliminary Rejection dated Jun. 28, 2007", (w/ EnglishTranslation), 40 pgs.
"New Zealand Application Serial No. 542935, Examination Report dated Feb. 25, 2008", 2 pgs.
"New Zealand Application Serial No. 542935, Examination Report dated Jun. 14, 2006", 2 pgs.
"New Zealand Application Serial No. 542935, Response filed Jun. 30, 2008 to Examination Report dated Feb. 25, 2008", 32 pgs.
"New Zealand Application Serial No. 542935, Response filed Aug. 7, 2007 to Examination Report dated Jun. 14, 2006", 18 pgs.

(56) References Cited

OTHER PUBLICATIONS

"New Zealand Application Serial No. 542935, Voluntary Amendments filed Sep. 12, 2007", 10 pgs.
"Russian Federation Application No. 2005136233, Response filed May 29, 2008 to Office Action dated Dec. 25, 2007", (w/ Partial English Translation), 7 pgs.
"Russian Federation Application Serial No. 2005136233, First Office Action dated Feb. 27, 2007", (w/ English Translation), 5 pgs.
"Russian Federation Application Serial No. 2005136233, Response filed Jun. 14, 2007 to First Office Action dated Feb. 27, 2007", (English Translation of Claims), 6 pgs.
"Russian Federation Application Serial No. 2005136233, Response filed Nov. 20, 2007 to Office Action", (w/ English Translation of Amended Claims), 18 pgs.
"Singapore Application Serial No. 200506858-0, Examination Report dated Feb. 9, 2007", 4 pgs.
"Singapore Application Serial No. 200506858-0, Response filed Dec. 22, 2006 to Written Opinion dated Jul. 26, 2006", 18 pgs.
"Singapore Application Serial No. 200506858-0, Written Opinion dated Jul. 26, 2006", 8 pgs.
"The Influenza Virus: Structure and Replication", Rapid Reference to Influenza. Elsevier Ltd, [Online]. Retrieved from the Internet: http://www.rapidreferenceinfluenza.com/chapter/B978-0-7234-3433-7.50009-8/aim/influenza-virus-structure, (2006).
"The Integral Membrane Proteins of Influenza A, B, and C Viruses", The Influenza Sequence Database, http://www.flu.lanl.gov/review/fluc.review2.html, (Observed Feb. 26, 2003), 1 pg.
Air, Gillian M., et al., "Antigenic, Sequence, and Crystal Variation in Influenza B Neuraminidase", Virology, 177(2), (1990), 578-587.
Author Unknown, "New Approaches to Influenza Vaccine". Medscape—Infections in Medicine, http://www.medscape.com/viewarticle/417404_3, (Observed Feb. 26, 1003), 4 pgs.
Avetisyan, G, et al., "Cell-mediated immune responses to influenza vaccination in healthy volunteers and allogeneic stem cell transplant recipients", Bone Marrow Transplant, (2005), 411-415.
Basler, C. F, et al., "Mutation of Neuraminidase Cysteine Residues Yields Temprature-Sensitive Influenza Viruses", Journal of Virology, 73(10), (Jun. 30, 1999), 8095-8103.
Betakova, T., et al., "The NB protein is an integral component of the membrane of influenza B virus.", J Gen Virol., 77 ( Pt 11), (Nov. 1996), 2689-94.
Bourmakina, S. V, et al., "Reverse genetics studies on the Filamentous morphology of influenza A Virus", Journal of General Virology (2003) 84,, (2003), 517-527.
Bowie, J. U., et al., "Deciphering the Message in Protein Sequences: Tolerance to Amino Acid Substitutions", Science, 247(4948), (1990), 1306-1310.
Brassard, D.L., et al., "Influenza B virus NB glycoprotein is a component of the virion", Virol., 220(2), No Document, (1996), 350-360.
Brooke, C B, "Biological activities of 'noninfectious' influenza A virus particles", Future Virol 9(1), (Jan. 2014), 41-51.
Castrucci, M. R, et al., "Reverse genetics system for generation of an influenza A virus mutant containing a deletion of the carboxyl-terminal residue of M2 protein.", Journal of Virology, 69(5), (1995), 2725-2728.
Castrucci, Maria R., et al., "Reverse genetics system for generation of an influenza A virus mutant containing a deletion of the carboxyl-terminal residue of M2 protein.", J Virol., 69(5), (May 1995), 2725-8.
Desheva, J. A, et al., "Characterization of an influenza A H5N2 reassortant as a candidate for live-attenuated and inactivated vaccines against hiahly pathogenic H5N1 viruses with pandemic potential", Vaccine, (2006), 6859-6866.
Dimmock, Nigel J, et al., "In vivo antiviral activity: defective interfering virus protects better against virulent Influenza A virus than avirulent virus", Journal of General Virology 87, (Jan. 8, 2006), 1259-1265.

Duff, K. C., et al., "The secondary structure of influenza A M2 transmembrane domain", FEBS Letters, 311 (3), , (Oct. 1992), pp. 256-258.
Duff, K. C., et al., "The Transmembrane Domain of Influenza A M2 Protein Forms Amantadine-Sensitive Proton Channels in Planar Lipid Bilayers", Vilology, 190(1), , (Sep. 1992), pp. 485-489.
Fan, J, et al., "Preclinical study of influenza virus A M2 peptide conjugate vaccines in mice, ferrets, and rhesus monkeys", Vaccine, 22, (2004), 2993-3003.
Fischer, W. B, et al., "Viral ion channels: structure and function.", Biochim Biophys Acta., 1561(1), (Mar. 19, 2002), 27-45.
Fleming, D. M, et al., "Comparison of the efficacy and safety of live attenuated cold-adapted influenza vaccine, trivalent, with trivalent inactivated influenza virus vaccine in children and adolescents with asthma", Pediatr Infect Dis J., 25(10), (2006), 860-869.
Fodor, E. et al., "Rescue of Influenza A Virus from Recombinant DNA", Journal of Virology, 73(11), XP002151487; ISSN:0022-538X, (Nov. 1999), 9679-9682.
Giddings, A M, et al., "The matrix protein of HIV-1 is not sufficient for assembly and release of virus-like particles", Virology, 248(1), (1998), 108-16.
Grambas, S., et al., "Influence of amantadine resistance mutations on the pH regulatory function of the M2 protein of influenza A viruses", Virology, 191(2), (Dec. 1992), 541-549.
Hai, Rong, et al., "Influenza B Virus NS1-Truncated Mutants: Live-Attenuated Vaccine Approach", Journal of Virology, 82(21), (2008), 10580-10590.
Harty, Ronald N, "A Proline-Rich Motif within the Matrix Protein of Vesicular Stomatitis Virus and Rabies Virus Interacts with WW Domains of Cellular Proteins: Implications for Viral Budding", Journal of Virology, 73 (4), (1999), 2921-2929.
Hatta, M., et al., "The NB Protein of Influenza B Virus Is Not Necessary for Virus Replication In Vitro", Journal of Virology, 77(10), (2003), 6050-6054.
Hay, A. J., et al., "The role of the M2 protein in influenza A virus infection", Proceedings of the International Conference on Options for the Control of Influenza, Courchevel, (1992), pp. 281-288.
Helenius, A., "Unpacking the Incoming Influenza Virus", Cell, 69, , (May 1992), pp. 577-578.
Hevey, Michael, et al., "Marburg virus vaccines based upon alphavirus replicons protect guinea pigs and nonhuman primates", Virology, 251(1), (Nov. 10, 1998), 28-37.
Hiromoto, Y., et al., "Phylogenetic Analysis of the Three Polymerase Genes (PB1, PB2 and PA) of Influenza B Virus", Journal of General Virology, 81, (Apr. 2000), 929-937.
Hoffmann, E., et al., "Rescue of Influenza B Virus from Eight Plasmids", Proceedings of the National Academy of Sciences of USA, National Academy of Science, 99(17), (Aug. 20, 2002), 11411-11416.
Holsinger, L. J., et al., "Influenza A Virus M2 Ion Channel Protein: a Structure-Function Analysis", Journal of Virology, 68 (3), (1994), pp. 1551-1563.
Hunt, R., "Virology—Chapter Eight—Vaccines: Past Successes and Future Prospects", Microbiology and Immunology On-Line, http://www.med.sc.edu:85/lecture/vaccines.htm, (Observed Feb. 26, 2003), 15 pgs.
Ives, J. A., et al., "The H274Y mutation in the influenza A/H1N1 neuraminidase active site following oseltamivir phosphate treatment leave virus severely compromised both in vitro and in vivo.", Antiviral Research, 55(2), (2002), 307-317.
Iwatsuki-Horimoto, K., et al., "The cytoplasmic tail of the influenza A virus M2 protein plays a role in viral assembly.", J Virol., 80(11), (Jun. 2006), 5233-40.
Jackson, D., et al., "A reverse genetics approach for recovery of recombinant influenza B viruses entirely from cDNA.", J Virol., 76(22), (Nov. 2002), 11744-7.
Jasenosky, Luke D, et al., "Ebola Virus VP40-Induced Particle Formation and Association with the Lipid Bilayer", Journal of Virology, 75 (110, (Jun. 2001), 5205-5214.
Kawaoka, Y, et al., "Sequence requirements for cleavage activation of influenza virus hemagglutinin expressed in mammalian cells", Proc Natl Acad Sci., 85(2), (1988), 324-328.

(56) References Cited

OTHER PUBLICATIONS

Kochendoerfer, G. G, et al. "Total Chemical Synthesis of the Integral Membrane Protein Influenza A Virus M2: Role of its C-Terminal Domain in Tetramer Assembly", Biochemistry 38, (1999), 11905-11913.

Krystal, M., et al., "Influenza B/Lee/40, hemagglutinin (seg 4), complete segment.", Database Accession No. K00423, Entrez Nucleotide Database, http://www.ncbi.nlm.nih.gov/entrez/viewer.fcgi?db-nucleotide&val=325175, (Apr. 25, 1990), 2 pgs.

Li, Y, et al., "Viral liposomes released from insect cells infected with recombinant baculovirus expressing the matrix protein of vesicular stomatitis virus", Journal of Virology, 67 (7), (1993), 4415-4420.

Lu, Xiuhua, et al., "Cross-protective immunity in mice induced by live-attenuated or inactivated vaccines against highly pathogenic influenza A (H5N1) viruses", Vaccine, 24(44-46), (2006), 6588-6593.

Luo, M., "Inhibitors of Influenza Virus Neuraminidase", Abstract No. WO296, from a paper presented at the Annual Meeting of the American Crystallographic Association, http://www.hwi.buffalo.edu/ACA/ACA98/abstracts/text/WO296.html, (Observed Feb. 27, 2003), 1 pg.

Mark, A, et al., "Effect of Mutations and Deletions in a Bicistronic mRNA on the Synthesis of Influenza B Virus NB and NA Glycoproteins", Journal of Virology, vol. 77, No. 10, (May 2003), 6050-6054.

McCown, M F, et al., "The influenza A virus M2 cytoplasmic tail is required for infectious virus production and efficient genome packaging.", J Virol., 79(6), (Mar. 2005), 3595-605.

McCown, M. F, et al., "Distinct domains of the influenza a virus M2 protein cytoplasmic tail mediate binding to the M1 protein and facilitate infectious virus production.", J Virol., 80(16), (Aug. 2006), 8178-89.

McKimm, J. L., et al., "Mutations in a Conserved Residue in the Influenza Virus Neuraminidase Active Site Decreases Sensitivity to Neu5Ac2en-Derived Inhibitors", Journal of Virology, 72(3), (1998), 2456-2462.

Mebatsion, Teshome, et al., "Budding of Rabies Virus Particles in the Absence of the Spike Glycoprotein", Cell, 84(6), (1996), 941-951.

Mebatsion, Teshome, et al., "Matrix Protein of Rabies Virus Is Responsible for the Assembly and Budding of Bullet-Shaped Particles and Interacts with the Transmembrane Spike Glycoprotein G", Journal of Virology, 73 (1), (Jan. 1999), 242/250.

Mena, I., "Rescue of a Synthetic Choramphenicol Acetyltransferase RNA into influenza Virus-Like Particles obtained from recombinant plasmids", Journal of Virology, 70(8), (1996), 5016-5024.

Mitnaul, et al., "The Cytoplasmic Tail of Influenza a Virus Neuraminidase (NA) Affects NA Incorporation into Virons, Viron Morphology, and Virulence in Mice but is not essential for Virus Replication", Journal of Virology, 70 (2), (1996), 873-879.

Monto, Arnold S, et al., "Comparative efficacy of inactivated and live attenuated influenza vaccines.", N Engl J Med., 361(13), (Sep. 24, 2009), 1260-7.

Murphy, Brian R, et al., "Virulence of Avian Influenza A Viruses for Squirrel Monkeys", Infection and Immunity 37 (3), (Sep. 1982), 1119-1126.

Muster, T., et al., "An Influenza A Virus Containing Influenza B Virus 5' and 3' Noncoding Regions on the Neuraminidase Gene is Attenuated in Mice", Proc. Natl. Acad. Sci. USA, 88, (1991), 5177-5181.

Neirynck, S., "A universal influenza A vaccine based on the extracellular domain of the M2 protein", Nature Medicine, 5 (10), (Oct. 1999), pp. 1157-1163.

Neumann, G., et al., "Generation of influenza A viruses entirely from cloned cDNAs", Proc. Natl. Acad. Sci. USA., 96(16), (1999), 9345-9350.

Neumann, G., et al., "Plasmid-driven formation of influenza virus-like particles", J Virol., 74(1), [Online] Retrieved From Internet: <http://www.ncbi.nlm.nih.gov/pmc/articles/PMC111569/>, (Jan. 2000), 547-551.

Neumann, G., et al., "RNA Polymerase I-Mediated Expression of Influenza Viral RNA Molecules", Virology, 202(1), (1994), 477-479.

Neumann, Gabriele, et al., "Reverse Genetics Demonstrates that Porteolytic Processing of the Ebola Virus Glycoprotein Is Not Essential for Replication in Cell Culture", Journal of Virology, 76 (1), (Jan. 2002), 406-410.

Palese, P., et al., "47. Orthomyxoviridae: The Viruses and Their Replication", In: Fields Virology (5th Edition), (2007), 90 pgs.

Park, Eun K., et al., "The M2 Ectodomain is important for its incorporation into influenza A virions", J. of Virology, vol. 72, No. 3, XP002196797, (Mar. 1998), 2449-2455.

Pekosz, A., et al., "Influenza C virus CM2 integral membrane glycoprotein is produced from a polypeptide precursor by cleavage of an internal signal sequence", PNAS, vol. 95, XP002196653, (Oct. 1998), 13233-13238.

Piller, S C., et al., "Vpr protein of human immunodeficiency virus type 1 forms cation-selective channels in planar lipid bilayers", PNAS, 93, , (1996), 111-1115.

Pinto, L. H., et al., "Influenza Virus M2 Protein Has Ion Channel Activity", Cell, 69, , (May 1992), pp. 517-528.

Pleschka, S., et al., "A Plasmid-Based Reverse Genetics System for Influenza A Virus", Journal of Virology, 70(6), (1996), 4188-4192.

Ruigrok, R W, et al., "Characterization of three highly purified influenza virus strains by electron microscopy", J Gen Virol 65 ( Pt 4), (Apr. 1984), 799-802.

Ruigrok, R W, et al., "Structural Characterization and Membrane Binding Properties of the Matrix Protein VP40 of Ebola Virus", Journal of Molecular Biology, 300(1), (2000), 103-112.

Sansom, M. S., et al., "Influenza virus M2 Protein: a molecular modelling study of the ion channel", Protein Engineering, 6 (1), (1993), pp. 65-74.

Schickli, J. H, et al., "Plasmid-only rescue of influenza A virus vaccine candidates.", Philos Trans R Soc Lond B Biol Sci., 356(1416), (Dec. 29, 2001), 1965-73.

Schnell, Matthias J, et al., "Requirement for a non-specific glycoprotein cytoplasmic domain sequence to drive efficient budding of vesicular stomatitis virus", EMBO Journal, 17(5), (1998), 1289-1296.

Shaw, M., et al., "Influenza B/Lee/40, neuraminidase & nb (seg 6)rna", Database accession No. J02095, Entrez Nucleotide Database, http://www.ncbi.nlm.nih.gov/entrez/viewer.fcgi?db=nucleotide&val=325235, (Jun. 13, 1985), 2 pgs.

Skehel, J. J., et al., "On the Mechanism of Inhibition of Influenza Virus Replication by Amantadine Hydrochloride", The Journal of General Virology, 38 (1), , (1977), pp. 97-110.

Sugrue, R. J., et al., "Specific structural alteration of the influenza haemagglutinin by amantadine", The EMBO Journal, 9 (11), (1990), pp. 3469-3476.

Sugrue, R. J., et al., "Structural Characteristics of the M2 Protein of Influenza A Viruses: Evidence That It Forms a Tetrameric Channel", Virology, 180, (1991), pp. 617-624.

Suguitan, A. L, et al., "Live, Attenuated Influenza A H5N1 Candidate Vaccines Provide Broad Cross-Protection in Mice and Ferrets", PLoS Med., 3(9), (2006), 1541-1555.

Sunstrom, N. A., et al., "Ion Channels formed by NB, an influenza B virus Protein", J. of Membrane Biology, vol. 150, XP002196654, (Dec. 1996), 127-132.

Sweet, T. M., et al., "Creation of amantadine resistant clones of influenza type A virus using a new transfection procedure.", J Virol Methods., 69(1-2), (Dec. 1997), 103-11.

Takeda, M., et al., "Influenza a virus M2 ion channel activity is essential for efficient replication in tissue culture.", J Virol., 76(3), (Feb. 2002), 1391-9.

Takeuchi, K., et al., "Influenza Virus M2 Protein Ion Channel Activity Stabilizes the Native Form of Fowl Plague Virus Hemagglutinin during Intracellular Transport", Journal of Virology, 68 (2), , (Feb. 1994), pp. 911-919.

Tannock, G. A, et al., "Relative immunogenicity of the cold-adapted influenza virus A/Ann Arbor/6/60 (A/AA/6/60-ca), recombinants of A/AA/6/60-ca, and parental strains with similar surface antigens.", Infect Immun., 43(2), (Feb. 1984), 457-62.

(56) References Cited

OTHER PUBLICATIONS

Tobler, K, "Effect of cytoplasmic tail truncations on the activity of the M(2) ion channel of influenza A virus", J Virol., (1999), 9695-701.
Uraki, R., et al., "A Novel Bivalent Vaccine Based on a PB2-Knockout Influenza Virus Protects Mice from Pandemic H1N1 and Highly Pathogenic H5N1 Virus Challenges", Journal of Virology, 87(14), (2013), 7874-7881.
Volchkov, Viktor E, et al., "Recovery of Infectious Ebola Virus from Complementary DNA: RNA Editing of the GP Gene and Viral Cytotoxicity", Science Magazine, 291, (Mar. 2001), 1965-1969.
Wagner, R., et al., "Interdependence of hemagglutinin glycosylation and neuraminidase as regulators of influenza virus growth: a study by reverse genetics", Journal of Virology, 74(14), (Jul. 2000), 6316-6323.
Wang, C., et al., "Ion Channel Activity of Influenza A Virus M2 Protein: Characterization of the Amantadine Block", Journal of Virology, 67 (9), (Sep. 1993), pp. 5585-5594.
Wareing, M. D, et al., "Immunogenic and isotype-specific responses to Russian and US cold-adapted influenza a vaccine donor strains A/Leningrad/134/17/57, A/Leningrad/134/47/57, and A/Ann Arbor/6/60 (H2N2) in mice.", J Med Virol., 65(1), (Sep. 2001), 171-7.
Watanabe, S., et al., "Influenza A Virus Lacking M2 Protein as a Live Attenuated Vaccine", Journal of Virology, 83(11), (2009), 5947-5950.
Watanabe, T., et al., "Influenza A virus can undergo multiple cycles of replication without M2 ion channel activity", J Virol., 75(12), (Jun. 2001), 5656-62.
Watanabe, T., et al., "Influenza A Virus with Defective M2 Ion Channel Activity as a Live Vaccine", Virology, 299(2), (Aug. 1, 2002), 266-270.
Watanabe, T., et al., "Influenza A virus with defective M2 ion channel activity as a live vaccine", Virology, 299(2), (Aug. 1, 2002), 266-70.
Williams, Mark A., et al., "Effect of Mutations and Deletions in a Bicistronic mRNA on the Synthesis of Influenza B Virus NB and NA Glycoproteins", Journal of Virology, 63(1), (1989), 28-35.
Wilson, Julie A, et al., "Epitopes Involved in Antibody-Mediated Protection from Ebola Virus", Science, 287, (Mar. 2000), 1664-1666.
Zebedee, S. L, et al., "Characterization of the Influenza Virus M2 Integral Membrane Protein and Expression at the Infected-Cell Surface from Cloned cDNA", Journal of Virology, 56(2), (Nov. 1985), 502-511.
"Result 17, NCBI Blast nucleotide search of SEQ ID No. 2, database "nr"", (Jul. 18, 2006), 3 pgs.
"Result 7, NCBI Blast nucleotide search of SEQ ID: 1, database "nr"", (Jul. 18, 2006), 3 pgs.
"Result 1, NCBI Blast nucleotide search of SEQ ID No. 3, database "nr""; Result 4, NCBI Blast nucleotide search of SEQ ID No. 4, database "nr", (Jul. 22, 2006), 11 pgs.
"Result 2, NCBI Blast nucleotide search of SEQ ID No. 5, database "nr""; Result 4, NCBI Blast nucleotide search of SEQ ID No. 6, database "nr", (Jul. 22, 2006), 6 pgs.
"Results 1, NCBI Blast nucleotide search of SEQ ID No. 7, database "nr""; Result 1, NCBI Blast nucleotide search of SEQ ID No. 8, database "nr", (Jul. 23, 2006), 8 pgs.
"U.S. Appl. No. 10/827,995, Notice of Allowance dated Jul. 2, 2008", 9 pgs.
"U.S. Appl. No. 10/855,875, Response filed May 17, 2012 to Non Final Office Action dated Mar. 15, 2012", 15 pgs.
"U.S. Appl. No. 10/855,875, Final Office Action dated Mar. 11, 2008", 20 pgs.
"U.S. Appl. No. 10/855,875, Final Office Action dated Dec. 10, 2010", 15 pgs.
"U.S. Appl. No. 10/855,875, Final Office Action dated Aug. 2, 2006", 34 pgs.
"U.S. Appl. No. 10/855,875, Non Final Office Action dated Mar. 15, 2012", 15 pgs.
"U.S. Appl. No. 10/855,875, Non-Final Office Action dated Feb. 19, 2010", 7 pgs.
"U.S. Appl. No. 10/855,875, Non-Final Office Action dated Aug. 7, 2009", 32 pgs.
"U.S. Appl. No. 10/855,875, Non-Final Office Action dated Nov. 6, 2008", 12 pgs.
"U.S. Appl. No. 10/855,875, Non-Final Office Action dated Nov. 30, 2005", 13 pgs.
"U.S. Appl. No. 10/855,875, Non-Final Office Action dated May 3, 2007", 13 pgs.
"U.S. Appl. No. 10/855,875, Notice of Allowance dated Mar. 4, 2013", 8 pgs.
"U.S. Appl. No. 10/855,875, Preliminary Amendment filed Feb. 2, 2007", 14 pgs.
"U.S. Appl. No. 10/855,875, Response filed Jan. 29, 2007 to Final Office Action dated Aug. 2, 2007", 14 pgs.
"U.S. Appl. No. 10/855,875, Response filed Mar. 18, 2011 to Final Office Action dated Dec. 10, 2010", 15 pgs.
"U.S. Appl. No. 10/855,875, Response filed Aug. 17, 2010 to Non Final Office Action dated Feb. 19, 2010", 20 pgs.
"U.S. Appl. No. 10/855,875, Response Filed Dec. 7, 2009 to Non-Final Office Action dated Aug. 7, 2009", 15 pgs.
"U.S. Appl. No. 10/855,875, Response filed Mar. 31, 2009 to Non Final Office Action dated Nov. 6, 2008", 14 pgs.
"U.S. Appl. No. 10/855,875, Response filed May 1, 2006 Non-Final Office Action dated Nov. 30, 2005", 13 pgs.
"U.S. Appl. No. 10/855,875, Response filed Aug. 18, 2008 to final Office Action dated Mar. 11, 2008", 15 pgs.
"U.S. Appl. No. 10/855,875, Response filed Sep. 20, 2005 to Restriction Requirement dated Jul. 26, 2005", 4 pgs.
"U.S. Appl. No. 10/855,875, Restriction Requirement dated Dec. 23, 2011", 9 pgs.
"U.S. Appl. No. 10/855,875, Restriction Requirement dated Jul. 26, 2005", 9 pgs.
"U.S. Appl. No. 10/855,875, Response filed Nov. 2, 2007 to Office Action dated May 3, 2007", 16 pgs.
"U.S. Appl. No. 11/729,557, Advisory Action dated May 9, 2011", 3 pgs.
"U.S. Appl. No. 11/729,557, Advisory Action dated Dec. 24, 2014", 3 pgs.
"U.S. Appl. No. 11/729,557, Final Office Action dated Feb. 2, 2011", 14 pgs.
"U.S. Appl. No. 11/729,557, Final Office Action dated Aug. 20, 2009", 13 Pgs.
"U.S. Appl. No. 11/729,557, Final Office Action dated Sep. 12, 2014", 14 pgs.
"U.S. Appl. No. 11/729,557, Non Final Office Action dated Feb. 18, 2015", 13 pgs.
"U.S. Appl. No. 11/729,557, Non Final Office Action dated Feb. 26, 2014", 16 pgs.
"U.S. Appl. No. 11/729,557, Non-Final Office Action dated Jan. 30, 2009", 20 pgs.
"U.S. Appl. No. 11/729,557, Non-Final Office Action dated Feb. 22, 2010", 16 pgs.
"U.S. Appl. No. 11/729,557, Non-Final Office Action dated Aug. 23, 2010", 15 pgs.
"U.S. Appl. No. 11/729,557, Notice of Allowance dated Sep. 30, 2015", 11 pgs.
"U.S. Appl. No. 11/729,557, Respons filed Jun. 22, 2010 to Non Final Office Action dated Feb. 22, 2010", 33 pgs.
"U.S. Appl. No. 11/729,557, Response filed Apr. 27, 2011 to Final Office Action dated Feb. 2, 2011", 14 pgs.
"U.S. Appl. No. 11/729,557, Response filed Apr. 30, 2009 to Non Final Office Action dated Jan. 30, 2009", 18 pgs.
"U.S. Appl. No. 11/729,557, Response filed May 22, 2014 to Non Final Office Action dated Feb. 26, 2014", 13 pgs.
"U.S. Appl. No. 11/729,557, Response filed May 28, 2008 to Restriction Requirement dated Nov. 28, 2007", 13 pgs.
"U.S. Appl. No. 11/729,557, Response filed Jun. 22, 2010 to Non Final Office Action dated Feb. 22, 2010", 16 pgs.
"U.S. Appl. No. 11/729,557, Response filed Jun. 22, 2015 to non Final Office Action dated Feb. 18, 2015", 13 pgs.

(56) References Cited

OTHER PUBLICATIONS

"U.S. Appl. No. 11/729,557, Response filed Oct. 28, 2010 to Non Final Office Action dated Aug. 23, 2010", 13 pgs.
"U.S. Appl. No. 11/729,557, Response filed Dec. 1, 2009 to Final Office Action dated Aug. 26, 2009", 16 pgs.
"U.S. Appl. No. 11/729,557, Response filed Dec. 11, 2014 to Final Office Action dated Sep. 12, 2014", 15 pgs.
"U.S. Appl. No. 11/729,557, Restriction Requirement dated Nov. 28, 2007", 9 pgs.
"U.S. Appl. No. 12/912,411, Advisory Action dated Feb. 5, 2014", 3 pgs.
"U.S. Appl. No. 12/912,411, Examiner Interview Summary dated Feb. 11, 2014", 2 pgs.
"U.S. Appl. No. 12/912,411, Final Office Action dated Jan. 14, 2015", 10 pgs.
"U.S. Appl. No. 12/912,411, Final Office Action dated Oct. 25, 2013", 11 pgs.
"U.S. Appl. No. 12/912,411, Non Final Office Action dated Jun. 7, 2013", 8 pgs.
"U.S. Appl. No. 12/912,411, Non Final Office Action dated Sep. 24, 2014", 11 pgs.
"U.S. Appl. No. 12/912,411, Response filed Jan. 27, 2014 to Final Office Action dated Oct. 25, 2013", 11 pgs.
"U.S. Appl. No. 12/912,411, Response filed Feb. 18, 2013 to Restriction Requirement dated Oct. 17, 2012", 9 pgs.
"U.S. Appl. No. 12/912,411, Response filed Feb. 25, 2014 to Final Office Action dated Oct. 25, 2013", 11 pgs.
"U.S. Appl. No. 12/912,411, Response filed Oct. 7, 2013 to Non Final Office Action dated Jun. 7, 2013", 10 pgs.
"U.S. Appl. No. 12/912,411, Response filed Dec. 31, 2014 to Non Final Office Action dated Sep. 24, 2014", 12 pgs.
"U.S. Appl. No. 12/912,411, Restriction Requirement dated Oct. 17, 2012", 9 pgs.
"U.S. Appl. No. 13/070,110, Advisory Action dated Mar. 3, 2017", 5 pgs.
"U.S. Appl. No. 13/070,110, Final Office Action dated Apr. 3, 2015", 18 pgs.
"U.S. Appl. No. 13/070,110, Final Office Action dated Jun. 12, 2013", 7 pgs.
"U.S. Appl. No. 13/070,110, Final Office Action dated Sep. 14, 2016", 12 pgs.
"U.S. Appl. No. 13/070,110, Non Final Office Action dated Jul. 21, 2017", 14 pgs.
"U.S. Appl. No. 13/070,110, Non Final Office Action dated Oct. 2, 2014", 24 pgs.
"U.S. Appl. No. 13/070,110, Non Final Office Action dated Dec. 11, 2015", 19 pgs.
"U.S. Appl. No. 13/070,110, Non Final Office Action dated Dec. 21, 2012", 7 pgs.
"U.S. Appl. No. 13/070,110, Preliminary Amendment filed Jun. 6, 2011", 4 pgs.
"U.S. Appl. No. 13/070,110, Response filed Feb. 14, 2017 to Final Office Action dated Sep. 14, 2016", 8 pgs.
"U.S. Appl. No. 13/070,110, Response filed Mar. 22, 2013 to Non Final Office Action dated Dec. 21, 2012", 8 pgs.
"U.S. Appl. No. 13/070,110, Response filed May 27, 2016 to Non Final Office Action dated Dec. 11, 2015", 13 pgs.
"U.S. Appl. No. 13/070,110, Response filed Jun. 20, 2017 to Advisory Action dated Mar. 3, 2017", 13 pgs.
"U.S. Appl. No. 13/070,110, Response filed 09-0314 to Restriction Requirement dated Jul. 8, 2014", 7 pgs.
"U.S. Appl. No. 13/070,110, Response filed Oct. 2, 2015 to Final Office Action dated Apr. 3, 2015", 11 pgs.
"U.S. Appl. No. 13/070,110, Response filed Nov. 21, 2013 to Final Office Action dated Jun. 12, 2013", 9 pgs.
"U.S. Appl. No. 13/070,110, Response filed Dec. 30, 2014 to Non Final Office Action dated Oct. 2, 2014", 13 pgs.
"U.S. Appl. No. 13/070,110, Restriction Requirement dated Jul. 8, 2014", 7 pgs.

"U.S. Appl. No. 14/332,121, Non Final Office Action dated May 16, 2016", 9 pgs.
"U.S. Appl. No. 14/332,121, Notice of Allowance dated Feb. 15, 2017", 10 pgs.
"U.S. Appl. No. 14/332,121, Notice of Allowance dated Jun. 15, 2017", 8 pgs.
"U.S. Appl. No. 14/332,121, Notice of Allowance dated Oct. 11, 2017", 8 pgs.
"U.S. Appl. No. 14/332,121, Preliminary Amendment filed Sep. 30, 2014", 5 pgs.
"U.S. Appl. No. 14/332,121, Response filed Jan. 29, 2016 to Restriction Requirement dated Jul. 30, 2015", 9 pgs.
"U.S. Appl. No. 14/332,121, Response filed Sep. 7, 2017 to Notice of Allowability dated Jun. 15, 2017", 8 pgs.
"U.S. Appl. No. 14/332,121, Response filed Oct. 11, 2016 to Non Final Office Action dated May 16, 2016", 9 pgs.
"U.S. Appl. No. 14/332,121, Restriction Requirement dated Jul. 30, 2015", 9 pgs.
"U.S. Appl. No. 14/332,121, Supplemental Amendment filed Jan. 23, 2017", 10 pgs.
"U.S. Appl. No. 15/000,851, Preliminary Amendment filed Feb. 3, 2016", 3 pgs.
"U.S. Appl. No. 15/000,851, Response filed Oct. 12, 2016 to Restriction Requirement dated May 12, 2016", 11 pgs.
"U.S. Appl. No. 15/000,851, Restriction Requirement dated May 12, 2016", 6 pgs.
"U.S. Appl. No. 15/000,851, Supplemental Amendment filed Apr. 4, 2016", 10 pgs.
"U.S. Appl. No. 15/593,039, Preliminary Amendment filed Jul. 25, 2017", 7 pgs.
"U.S. Appl. No. 15/593,039, Response filed Dec. 18, 2017 to Restriction Requirement dated Oct. 18, 2017", 8 pgs.
"U.S. Appl. No. 15/593,039, Restriction Requirement dated Oct. 18, 2017", 6 pgs.
"U.S. Appl. No. 15/593,039, Supplemental Preliminary Amendment filed Jul. 26, 2017", 4 pgs.
"Application Serial No. 200480021259.9 Office Action dated Sep. 11, 2009", 7 pgs.
"Application Serial No. 200480021259.9 Office Action Response Filed Aug. 20, 2010", 26 pgs.
"Application Serial No. 2006-533439 Office Action dated Mar. 9, 2010", 20 pgs.
"Australian Application Serial No. 2004249133, First Examiners Report dated May 5, 2008", 4 pgs.
"Australian Application Serial No. 2004249133, Response filed Mar. 30, 2009 to First Examiner's Report dated May 5, 2008", 30 pgs.
"Australian Application Serial No. 2007245192, Office Action dated Aug. 25, 2011", 2 pgs.
"Australian Application Serial No. 2007245192, Response filed Feb. 28, 2012 to Office Action dated Aug. 25, 2011", 22 pgs.
"Australian Application Serial No. 2012204138, First Examiner Report dated Jul. 16, 2013", 4 pgs.
"Australian Application Serial No. 2012204138, Response filed Dec. 24, 2013 to First Examiner Report dated Jul. 16, 2013", 21 pgs.
"Australian Application Serial No. 2014202470, First Examiner Report dated Jul. 20, 2015", 2 pgs.
"Australian Application Serial No. 2014202470, Respojnse filed Jul. 4, 2016 to Subsequent Examiners Report dated Feb. 1, 2016", 3 pgs.
"Australian Application Serial No. 2014202470, Response filed Jul. 20, 2016 to Subsequent Examiners Report dated Jul. 19, 2016", 15 pgs.
"Australian Application Serial No. 2014202470, Response filed Dec. 1, 2015 to First Examiner Report dated Jul. 20, 2015", 22 pgs.
"Australian Application Serial No. 2014202470, Subsequent Examiners Report dated Feb. 1, 2016", 2 pgs.
"Australian Application Serial No. 2014202470, Subsequent Examiners Report dated Jul. 19, 2016", 3 pgs.
"Brazilian Application Serial No. PI0410702-0, Office Action dated Feb. 23, 2012", (w/ English Translation), 4 pgs.

(56) References Cited

OTHER PUBLICATIONS

"Brazilian Application Serial No. PI0410702-0, Response filed May 7, 2012 to Office Action dated Feb. 23, 2012", (w/ English Translation of Claims), 11 pgs.
"Canadian Application Serial No. 2,522,081, Office Action filed Nov. 18, 2011", 11 pgs.
"Canadian Application Serial No. 2,525,953, Office Action dated Jan. 21, 2016", 6 pgs.
"Canadian Application Serial No. 2,525,953, Office Action dated Jul. 31, 2012", 4 pgs.
"Canadian Application Serial No. 2,525,953, Office Action dated Aug. 1, 2016", 6 pgs.
"Canadian Application Serial No. 2,525,953, Office Action dated Aug. 16, 2013", 3 pgs.
"Canadian Application Serial No. 2,525,953, Office Action dated Nov. 6, 2014", 3 pgs.
"Canadian Application Serial No. 2,525,953, Office Action dated Jun. 22, 2011", 4 pgs.
"Canadian Application Serial No. 2,525,953, Response filed Feb. 14, 2014 to Office Action dated Aug. 16, 2013", 16 pgs.
"Canadian Application Serial No. 2,525,953, Response filed Jul. 11, 2016 to Office Action dated Jan. 21, 2016", 21 pgs.
"Canadian Application Serial No. 2,525,953, Response filed Dec. 22, 2011 to Office Action dated Jun. 22, 2011", 17 pgs.
"Canadian Application Serial No. 2,647,985, Office Action dated May 15, 2013", 3 pgs.
"Canadian Application Serial No. 2,647,985, Response filed Sep. 30, 2013 to Office Action dated May 15, 2013", 20 pgs.
"Chinese Application Serial No. 200480021259.9, First Office Action dated Aug. 24, 2007", (w/ English Translation), 9 pgs.
"Chinese Application Serial No. 200480021259.9, Notice of Reexamination dated Jul. 3, 2012", (w/ English Translation), 10 pgs.
"Chinese Application Serial No. 200480021259.9, Office Action dated Jan. 11, 2011", (w/ English Translation), 15 pgs.
"Chinese Application Serial No. 200480021259.9, Office Action dated May 6, 2010", (w/ English Translation), 12 pgs.
"Chinese Application Serial No. 200480021259.9, Office Action dated Jul. 3, 2012", (w/ English Translation), 10 pgs.
"Chinese Application Serial No. 200480021259.9, Request for Reexamination filed Apr. 26, 2011", (w/ English Translation of Amended Claims), 23 pgs.
"Chinese Application Serial No. 200480021259.9, Response filed Mar. 7, 2008 to Office Action dated Aug. 24, 2007", (w/ English Translation of Claims), 13 pgs.
"Chinese Application Serial No. 200480021259.9, Response filed Oct. 16, 2012 to Office Action dated Jul. 3, 2012", (w/ English Translation of Claims), 13 pgs.
"Chinese Application Serial No. 200780020095.1, Decision on Rejection dated Jul. 22, 2013", (w/ English Translation), 11 pgs.
"Chinese Application Serial No. 200780020095.1, First Office Action dated Jun. 24, 2011", (w/ English Translation), 13 pgs.
"Chinese Application Serial No. 200780020095.1, Office Action dated Jan. 29, 2013", (w/ English Translation), 10 pgs.
"Chinese Application Serial No. 200780020095.1, Office Action dated Mar. 5, 2015", (w/ English Translation), 12 pgs.
"Chinese Application Serial No. 200780020095.1, Office Action dated Apr. 26, 2016", (w/ English Summary), 4 pgs.
"Chinese Application Serial No. 200780020095.1, Office Action dated May 3, 2012", (w/ English Translation), 10 pgs.
"Chinese Application Serial No. 200780020095.1, Office Action dated Nov. 2, 2016", (w/ English Translation), 11 pgs.
"Chinese Application Serial No. 200780020095.1, Response filed Jun. 9, 2013 to Office Action dated Jan. 29, 2013", (w/ English Translation of Claims), 10 pgs.
"Chinese Application Serial No. 200780020095.1, Response filed Jun. 23, 2015 to Office Action dated Mar. 5, 2015", (w/ English Translation of Claims), 16 pgs.
"Chinese Application Serial No. 200780020095.1, Response filed Jun. 30, 2016 to Office Action dated Apr. 26, 2016", (w/ English Translation of Claims), 22 pgs.

"Chinese Application Serial No. 200780020095.1, Response filed Sep. 17, 2012 to Office Action dated May 3, 2012", (w/ English Translation of Claims), 17 pgs.
"Chinese Application Serial No. 200780020095.1, Response filed Nov. 5, 2013 to to Decision on Rejection dated Jul. 22, 2013", (w/ English Translation of Claims), 12 pgs.
"Chinese Application Serial No. 200780020095.1, Response filed Nov. 8, 2011 to Office Action dated Jun. 24, 2011", (w/ English Translation of Amended Claims), 20 pgs.
"Chinese Application Serial No. 200480021259.9, Office Action dated May 8, 2009", (w/ English Translation), 6 pgs.
"Eurasian Application No. 200501890, Notice of Allowance dated Jun. 23, 2009", 1 pg.
"Eurasian Application Serial No. 200501890, Office Action dated Mar. 23, 2007", (w/ English Translation), 2 pgs.
"Eurasian Application Serial No. 200501890, Office Action dated Sep. 4, 2008", (English Translation), 1 pg.
"Eurasian Application Serial No. 200501890, Office Action dated Dec. 17, 2007", (w/ English Translation), 6 pgs.
"Eurasian Application Serial No. 200501890, Response filed Mar. 26, 2008 to Office Action dated Dec. 17, 2007", (w/ English Translation of Claims), 15 pgs.
"Eurasian Application Serial No. 200501890, Response filed Jun. 14, 2007 to Office Action dated Mar. 23, 2007", (w/ English Translation of Claims), 11 pgs.
"Eurasian Application Serial No. 200501890, Response filed Dec. 17, 2008 to Office Action", (w/ English Translation of Claims), 13 pgs.
"Eurasian Application Serial No. 200501890, Response filed Dec. 17, 2008 to Office Action dated Sep. 4, 2008", (w/ English Translation of Claims), 14 pgs.
"European Application Serial No. 04776133.3, Communication dated Mar. 30, 2006", 3 pgs.
"European Application Serial No. 04776133.3, Examination Notification Art. 94(3) dated Jul. 28, 2015", 4 pgs.
"European Application Serial No. 04776133.3, Examination Notification Art. 94(3) dated Nov. 25, 2013", 5 pgs.
"European Application Serial No. 04776133.3, Office Action dated Jan. 5, 2010", 4 pgs.
"European Application Serial No. 04776133.3, Response filed Jan. 25, 2007 to Communication dated Mar. 30, 2006", 20 pgs.
"European Application Serial No. 04776133.3, Response filed Apr. 30, 2014 to Examination Notification Art. 94(3) dated Nov. 25, 2013", 12 pgs.
"European Application Serial No. 04776133.3, Response filed Jul. 15, 2010 to Office Action dated Jan. 5, 2010", 9 pgs.
"European Application Serial No. 04776133.3, Response filed Sep. 18, 2015 to Examination Notification Art. 94(3) dated Jul. 28, 2015", 47 pgs.
"European Application Serial No. 07754132.4, Office Action dated Apr. 28, 2009", 4 pgs.
"European Application Serial No. 07754132.4, Office Action dated Sep. 5, 2011", 5 pgs.
"European Application Serial No. 07754132.4, Office Action dated Nov. 2, 2012", 4 pgs.
"European Application Serial No. 07754132.4, Response filed Feb. 5, 2010 to Office Action dated Apr. 28, 2009", 15 pgs.
"European Application Serial No. 07754132.4, Response filed Mar. 15, 2012 to Office Action dated Sep. 5, 2011", 21 pgs.
"European Application Serial No. 07754132.4, Response filed May 10, 2013 to Office Action dated Nov. 2, 2012", 14 pgs.
"European Application Serial No. 07754132.4, Response filed Jun. 26, 2013", 8 pgs.
"European Application Serial No. 10777154.5, Examination Notification Art. 94(3) dated Oct. 6, 2014", 7 pgs.
"European Application Serial No. 10777154.5, Office Action dated Jul. 4, 2012", 2 pgs.
"European Application Serial No. 10777154.5, Response filed Jan. 14, 2013 to Office Action dated Jul. 4, 2012", 12 pgs.
"European Application Serial No. 14745060.5, Office Action dated Feb. 23, 2016", 2 pgs.

(56) References Cited

OTHER PUBLICATIONS

"Hemagglutinin [Influenza A virus (A/swine/France/WVL13/ 1995(H1N1))]", GenBank Accession# AC025026, (May 22, 2009), 1 pg.
"Indian Application Serial No. 1026/KOLNP/2009, First Examiner Report dated Mar. 13, 2014", 2 pgs.
"Indian Application Serial No. 2272/KOLNP/2005, First Examination Report dated Mar. 17, 2008", 10 pgs.
"Indian Application Serial No. 2272/KOLNP/2005, Response filed Mar. 16, 2009 to Subsequent Examination Report dated Mar. 6, 2009", 12 pgs.
"Indian Application Serial No. 2272/KOLNP/2005, Response filed Oct. 11, 2008 to First Examination Report dated Mar. 17, 2008", 27 pgs.
"Indian Application Serial No. 2272/KOLNP/2005, Subsequent Examination Report dated Mar. 6, 2009", 1 pg.
"Influenza B/lee/40, neuraminidase & nb (seg 6) ma", Database EM_VI E.B.I. Hinxton U.K., (Jun. 13, 1985), 10 pgs.
International Application Serial No. PCT/US2004/016680, International Search Report dated Feb. 2, 2005, 7 pgs.
"International Application Serial No. PCT/US2004/016680, International Preliminary Report on Patentability dated Dec. 15, 2005", 11 pgs.
"International Application Serial No. PCT/US2007/007562, International Preliminary Report on Patentability dated Oct. 9, 2008", 5 pgs.
"International Application Serial No. PCT/US2007/007562, International Search Report dated Jan. 14, 2008", 8 pgs.
"International Application Serial No. PCT/US2007/007562, Written Opinion dated Jan. 14, 2008", 9 pgs.
"International Application Serial No. PCT/US2010/054128, Preliminary Report on Patentability dated May 10, 2012", 10 pgs.
"International Application Serial No. PCT/US2010/054128, Search Report dated Feb. 23, 2011", 6 pgs.
"International Application Serial No. PCT/US2010/054128, Written Opinion dated Feb. 23, 2011", 8 pgs.
"International Application Serial No. PCT/US2014/046731, International Preliminary Report on Patentability dated Jan. 28, 2016", 12 pgs.
"International Application Serial No. PCT/US2014/046731, International Search Report dated Nov. 25, 2014", 9 pgs.
"International Application Serial No. PCT/US2014/046731, Written Opinion dated Nov. 25, 2014", 10 pgs.
"Israeli Application Serial No. 171831, Notification of Defects dated Nov. 10, 2008", (English Translation), 10 pgs.
"Israeli Application Serial No. 171831, Office Action dated Feb. 21, 2010", (English Translation), 2 pgs.
"Israeli Application Serial No. 171831, Office Action dated Apr. 18, 2012", (English Translation), 2 pgs.
"Israeli Application Serial No. 171831, Response filed Jan. 20, 2011 to Office Action dated Feb. 21, 2010", (English Translation), 18 pgs.
"Israeli Application Serial No. 171831, Response filed Jun. 24, 2009 to Notification of Defects dated Nov. 10, 2008", (w/ English Translation of Claims), 10 pgs.
"Israeli Application Serial No. 171831, Response filed Nov. 6, 2012 to Office Action dated Apr. 18, 2012", (w/ English Translation of Amended Claims), 54 pgs.
"Israeli Application Serial No. 238584, Office Action dated Apr. 14, 2016", (English Translation), 3 pgs.
"Israeli Application Serial No. 238584, Response filed Aug. 3, 2016 to Office Action dated Apr. 14, 2016", (English Translation of Claims), 19 pgs.
"Japanese Application Serial No. 2006-533439, Decision of Final Rejection dated Aug. 14, 2012", (w/ English Translation), 5 pgs.
"Japanese Application Serial No. 2006-533439, Office Action dated Mar. 27, 2012", w/ English Translation, 8 pgs.
"Japanese Application Serial No. 2006-533439, Response filed May 21, 2012 to Office Action dated Mar. 27, 2012", (w/ English Translation of Amended Claims), 19 pgs.
"Japanese Application Serial No. 2006-533439, Response filed Aug. 3, 2011 to Office Action dated Feb. 15, 2011", (w/ English Translation of Amended Claims), 18 pgs.
"Japanese Application Serial No. 2006-533439,Office Action dated Feb. 15, 2011", (w/ English Translation), 13 pgs.
"Japanese Application Serial No. 2006-533439; Office Action Response filed Jul. 9, 2010", (w/ English Translation of Claims), 25 pgs.
"Japanese Application Serial No. 2009-502945, Examiners Decision of Final Refusal dated Nov. 12, 2013", (w/ English Translation), 8 pgs.
"Japanese Application Serial No. 2009-502945, Office Action dated Oct. 23, 2012", (w/ English Translation), 16 pgs.
"Japanese Application Serial No. 2009-502945, Response filed Apr. 10, 2013 to Office Action dated Oct. 23, 2012", (w/ English Translation of Claims), 18 pgs.
"Japanese Application Serial No. 2012-273898, Office Action dated Jun. 10, 2014", (w/ English Translation), 7 pgs.
"Japanese Application Serial No. 2012-273898, Response filed Sep. 4, 2014 to Office Action dated Jun. 10, 2014", W/ English Claims, 9 pgs.
"Japanese Application Serial No. 2012-536963, Office Action dated Jan. 6, 2015", (w/ English Translation), 14 pgs.
"Japanese Application Serial No. 2012-536963, Voluntary Amendment filed Jun. 27, 2012", (w/ English Translation of Amended Claims), 17 pgs.
"Japanese Application Serial No. 2014-049025 Response filed Sep. 4, 2015 to Office Action dated Jun. 16, 2015", (w/ Amended Claims), 12 pgs.
"Japanese Application Serial No. 2014-049025, Examiners Decision of Final Refusal dated Feb. 2, 2016", (w/ English Translation), 5 pgs.
"Japanese Application Serial No. 2014-049025, Office Action dated Jun. 16, 2015", (w/ English Translation), 6 pgs.
"Korean Application Serial No. 10-2005-7022564, Notice of Preliminary Rejection dated Jul. 25, 2007", (w/ English Translation), 5 pgs.
"Korean Application Serial No. 10-2005-7022564, Office Action dated Aug. 6, 2008", (w/ English Translation), 4 pgs.
"Korean Application Serial No. 10-2005-7022564, Response and Amendment filed Dec. 29, 2008 to Office Action dated Aug. 6, 2008", (w/ English Translation), 16 pgs.
"Korean Application Serial No. 10-2005-7022564, Response filed Mar. 25, 2008 to Notice of Preliminary Rejection dated Jul. 25, 2007", (w/ English Translation of Claims), 35 pgs.
"Korean Application Serial No. 10-2005-7022564, Response filed Dec. 29, 2008 to Office Action dated Aug. 6, 2008", (w/ English Translation of Claims), 16 pgs.
"Mexican Application No. PA/a/2005/012712 Office Action dated Jul. 21, 2009", (w/ English Translation), 9 pgs.
"Mexican Application Serial No. MX/a/2009/006341, Office Action dated Mar. 29, 2012", (English Translation), 1 pg.
"Mexican Application Serial No. MX/a/2009/006341, Response filed Jun. 4, 2012 to Mar. 29, 2012", (w/ English Translation of Amended Claims), 16 pgs.
"Mexican Application Serial No. MX/a/2012/009249 Response filed Sep. 10, 2015 to Office Action dated May 19, 2015", (w/ English Translation of Claims), 21 pgs.
"Mexican Application Serial No. MX/a/2012/009249, Office Action dated Feb. 5, 2016", (w/ English Claims), 2 pgs.
"Mexican Application Serial No. MX/a/2012/009249, Office Action dated May 19, 2015", (English Translation), 1 pg.
"Mexican Application Serial No. MX/a/2012/009249, Response filed Mar. 29, 2016 to Office Action dated Feb. 5, 2016", (English Translation of Claims), 18 pgs.
"Mexican Application Serial No. PA/a/2005/011250, Office Action dated Aug. 23, 2010", (w/ English Translation), 4 pgs.
"Mexican Application Serial No. PA/a/2005/011250, Response Filed Dec. 20, 2010 to Office Action dated Aug. 23, 2010", (wl English Translation of Claims), 14 pgs.
"Mexican Application Serial No. PA/a/2005/012712 , Office Action dated Aug. 11, 2009", (English Translation), 5 pgs.
"Mexican Application Serial No. PA/a/2005/012712, Office Action dated May 12, 2010", (w/ English Translation), 19 pgs.

(56) References Cited

OTHER PUBLICATIONS

"Mexican Application Serial No. PA/a/2005/012712, Office Action dated Jun. 9, 2010", (w/ English Translation), 11 pgs.
"Mexican Application Serial No. PA/a/2005/012712, Office Action dated Nov. 30, 2009", (w/ English Translation), 14 pgs.
"Mexican Application Serial No. PA/a/2005/012712, Official Action dated Mar. 5, 2009", (English Translation), 2 pgs.
"Mexican Application Serial No. PA/a/2005/012712, Response filed Sep. 27, 2010 to Office Action dated May 12, 2010", (w/ English Translation of Claims), 19 pgs.
"Neuraminidase, partial [Influenza A virus (A/swine/France/WVL13/1995(H1N1))]", GenBank Accession# AC025028, (May 22, 2009), 2 pgs.
"New Zealand Application Serial No. 543446, Examination Report dated Feb. 29, 2008", 2 pgs.
"New Zealand Application Serial No. 543446, Examination Report dated May 12, 2008", 2 pgs.
"New Zealand Application Serial No. 543446, Response dated Mar. 20, 2008 to Examination Report dated Feb. 29, 2008", 2 pgs.
"Russian Federation Application No. 2005136233, Office Action dated Dec. 25, 2007", 2 pgs.
"Singaporean Application Serial No. 200507468-7, Examination Report dated Mar. 19, 2008", 5 pgs.
"Singaporean Application Serial No. 200507468-7, Invitation to Respond to Written Opinion dated Jun. 12, 2007", 6 pgs.
"Singaporean Application Serial No. 200507468-7, Response filed Nov. 7, 2007 to Invitation to Respond to Written Opinion dated Jun. 12, 2007", 9 pgs.
"Ukrainian Application Serial No. 200512619, Office Action dated Feb. 27, 2009", (w/ English Translation), 21 pgs.
"Ukrainian Application Serial No. 200512619, Office Action dated Jun. 17, 2009", (w/ English Translation), 4 pgs.
"Ukrainian Application Serial No. 200512619, Response filed Apr. 8, 2009 to Office Action dated Feb. 27, 2009", (w/ English Translation of Claims), 9 pgs.
Air, Gillian M., et al., "Antigenic, Sequence, and Crystal Variation in Influenza B Neuraminidase", Virology vol. 177,, (1990), 578-587.
Baez, M., et al., "Complete nucleotide sequence of the influenza A/PR/8/34 virus NS gene and comparison with the NS genes of the A/Udorn/72 and A/FPV/Rostock/34 strains", Nucleic Acids Research, 23(8), (1980), 5845-5858.
Bancroft, C. T, et al., "Evidence for segment-nonspecific packaging of the influenza a virus genome", J Virol., 76(14), (Jul. 2002), 7133-9.
Banerjee, A. K., et al., "Gene Expression of Vesicular Stomatitis Virus Genome RNA.", Virology, 188(2), (1992), 417-428.
Baron, M. D., et al., "Rescue of Rinderpest Virus From Cloned cDNA", Journal of Virology, 71(2), (1997), 1265-1271.
Beare, A. S., "Trials in Man With Live Recombinants Made From A/PR/8/34 (H0 N1) and Wild H3 N2 Influenza Viruses", The Lancet, 2(7938), (1975), 729-732.
Boyer, J. C., et al., "Infectious transcripts and cDNA clones of RNA viruses", Virology, 198(2), (Feb. 1994), 415-426.
Bridgen, A., "Rescue of a Segmented Negative-Strand RNA Virus Entirely From Cloned Complementary DNAs", Proc. Natl. Acad. Sci. USA, 93, (1996), 15400-15404.
Brown, E. G., et al., "Genetic analysis of mouse-adapted influenza A virus identifies roles for the NA, PB1, and PB2 genes in virulence", Virus Research, 61(1), (May 1999), 63-76.
Buchholz, U. J., et al., "Generation of Bovine Respiratory Syncytial Virus (BRSV) From cDNA: Brsv NS2 is Not Essentiial for Virus Replication in Tissue Culture, and the Human RSV Leader Region Acts as a Functional BRSV Genome Promoter", Journal of Virology, 73(1), (1999), 251-259.
Bukreyev, A., et al., "Recovery of infectious respiratory syncytial virus expressing an additional, foreign gene", Journal of Virology, 70(10), (Oct. 1996), 6634-6641.
Chen, H, et al., "Generation and evaluation of a high-growth reassortant H9N2 influenza A virus as a pandemic vaccine candidate", Vaccine, 21(17-18), (May 16, 2003), 1974-9.
Chen, Z., et al., "Influenza A Virus NS1 Protein Targets Poly(A)-Binding Protein II of the Cellular 3'-End Processing Machinery", The EMBO Journal, 18(8), (1999), 2273-2283.
Clarke, D. K., et al., "Rescue of Mumps Virus From cDNA", Journal of Virology, 74(10), (2000), 4831-4838.
Collins, P. L., et al., "Chapter 41—Parainfluenza Viruses", In: Fields Virology, edited by Fields, B. N., et al. (3rd Edition, 1996, Lippincott—Raven Publishers, Philadelphia, PA, 1205-1241.
Collins, P. L., et al., "Production of Infectious Human Respiratory Syncytial Virus From Cloned cDNA Confirms an Essential Role for the Transcription Elongation Factor From the 5' Proximal Open Reading Frame of the M2 mRNA in Gene Expression and Provides a Capability for Vaccine D", Proc. Natl. Acad. Sci. USA, 92, (1995), 11563-11567.
Collins, P. L., "Rescue of Synthetic Analogs of Respiratory Syncytial Virus Genomic RNA and Effect of Truncations and Mutations on the Expression of a Foreign Reporter Gene", Proc. Natl. Acad. Sci. USA, 88, (1991), 9663-9667.
Conzelmann, K.-K., "Genetic Engineering of Animal RNA Viruses", Trends in Microbiology, 4(10), (1996), 386-393.
Conzelmann, K.-K., "Genetic manipulation of non-segmented negative-strand RNA viruses", Journal of General Virology, 77(Pt. 3), (Mar. 1996), 381-389.
Conzelmann, K.-K., "Nonsegmented Negative-Strand RNA Viruses: Genetics and Manipulation of Viral Genomes", Annu. Rev. Genet., 32, (1998), 123-162.
Conzelmann, K.-K., "Rescue of Synthetic Genomic RNA Analogs of Rabies Virus by Plasmid-Encoded Proteins", Journal of Virology, 68(2), (1994), 713-719.
De, B. P., et al., "Requirements and Functions of Vesicular Stomatitis Virus L and NS Proteins in the Transcription Process in Vitro", Biochemical and Biophysical Research Communications, 126(1), (1985), 40-49.
De, B. P., et al., "Rescue of synthetic analogs of genome RNA of human parainfluenza virus type 3", Virology, 196(1), (Sep. 1993), 344-348.
De, B. P., et al., "Reverse Genetics of Negative Strand RNA Viruses", Indian Journal of Biochemistry & Biophysics, 31, (1994), 367-375.
De Filette, Marina, et al., "An influenza A vaccine based on tetrameric ectodomain of matrix protein 2", J Biol Chem. 2008 ; 283 (17):, (Feb. 5, 2008), 11382-7.
De La Luna, S., et al., "Influenza virus naked RNA can be expressed upon transfection into cells co-expressing the three subunits of the polymerase and the nucleoprotein from simian virus 40 recombinant viruses", Journal of General Virology, 74(pt. 3), (Mar. 1993), 535-539.
De La Luna, S., et al., "Influenza Virus NS1 Protein Enhances the Rate of Translation Initiation of Viral mRNAs", Journal of Virology, 69(4), (1995), 2427-2435.
Dimock, K., et al., "Rescue of Synthetic Analogs of Genomic RNA and Replicative-Intermediate RNA of Human Parainfluenza Virus Type 3", Journal of Virology, 67(5), (1993), 2772-2778.
Dreher, T. W., et al., "Mutational Analysis of the Sequence and Structural Requirements in Brome Mosaic Virus RNA for Minus Strand Promoter Activity", Journal of Molecular Biology, 201(1), (1988), 31-40.
Dunham, Eleca J., et al., "Different Evolutionary Trajectories of European Avian-Like and Classical Swine H1N1 Influenza A Viruses", Journal of Virology, 83(11), (Jun. 2009), 5485-5494.
Dunn, E. F., et al., "Transcription of a recombinant bunyavirus RNA template by transiently expressed bunyavirus proteins", Virology, 211(1), (1995), 133-143.
Durbin, A. P., et al., "Recovery of infectious human parainfluenza virus type 3 from cDNA", Virology, 235(2), (Sep. 1, 1997), 323-332.
Elliott, R. M., et al., "Rescue of Infectious Bunyavirus Entirely From Cloned cDNA", 10th International Conference on Negative Strand Virus, (Abstract No. 96), (1997), 1 pg.

(56) References Cited

OTHER PUBLICATIONS

Elliott, R. M., et al., "Some Highlights of Virus Research in 1990", Journal of General Virology, 72(Part 8), (1991), 1761-1779.
Emerson, S. U., et al., "Both NS and L Proteins Are Required for In Vitro RNA Synthesis by Vesicular Stomatitis Virus", Journal of Virology, 15(6), (1975), 1348-1356.
Enami, M., "An Influenza Virus Containing Nine Different RNA Segments", Virology, 185(1), (1991), 291-298.
Enami, M., et al., "High-Efficiency Formation of Influenza Virus Transfectants", Journal of Virology, 65(5), (1991), 2711-2713.
Enami, M., et al., "Introduction of Site-Specific Mutations Into the Genome of Influenza Virus", Proc. Natl. Acad. Sci. USA, 87, (1990), 3802-3805.
Fahey, J. L., "Status of Immune-Based Therapies in HIV Infection and Aids", Clinincal and Experimental Immunology, 88(1), (1992), 1-5.
Forbes, Nicole E, et al., "Multifunctional Adaptive NS1 Mutations Are Selected upon Human Influenza Virus Evolution in the Mouse", Plos One, vol. 7, No. 2, (Feb. 21, 2012).
Fortes, P., et al., "Influenza Virus NS1 Protein Inhibits Pre-mRNA Splicing and Blocks mRNA Nucleocytoplasmic Transport", The EMBO Journal, 13(3), (1994), 704-712.
Garcia-Sastre, A., et al., "Genetic Manipulation of Negative-Strand RNA Virus Genomes", Annu. Rev. Microbiol., 47, (1993), 765-790.
Garcin, D., et al., "A Highly Recombinogenic System for the Recovery of Infectious Sendai Paramyxovirus From cDNA: Generation of a Novel Copy-Back Nondefective Interfering Virus", The EMBO Journal, 14(24), (1995), 6087-6094.
Gotea, V, et al., "The functional relevance of somatic synonymous mutations in melanoma and other cancers", Pigment Cell & Melanoma Research, 28 issue 6, (Nov. 1, 2015), 673-686.
Goto, H., "Mutations Affecting the Sensitivity of the Influenza Virus Neuraminidase to 4-Guanidino-2, 4-dideoxy 2, 3-dehydro-N-acetylneuraminic Acid", Virology, 238, (1997), 265-272.
Grosfeld, H., et al., "RNA Replication by Respiratory Syncytial Virus (RSV) Is Directed by the N, P, and L Proteins; Transcription Also Occurs Under These Conditions but Require RSV Superinfection for Efficient Synthesis of Full-Length mRNA", Journal of Virology, 69(9), (1995), 5677-5686.
Hatada, E., et al., "Binding of Influenza A Virus NS1 Protein to dsRNA in vitro", Journal of General Virology, 73, (1992), 3325-3329.
Hatta, M., et al., "The NB protein of influenza B virus is not necessary for virus replication in vitro", Journal of Virology, 77(10), (May 2003), 6050-6054.
He, B., et al., "Recovery of infectious SV5 from cloned DNA and expression of a foreign gene", Virology, 237(2), (1997), 249-260.
Hoffman, M. A., et al., "An Infectious Clone of Human Parainfluenza Virus Type 3", Journal of Virology, 71(6), (1997), 4272-4277.
Hoffmann, E., et al., "A DNA transfection system for generation of influenza A virus from eight plasmids", Proc Natl Acad Sci U S A., 97(11), (May 23, 2000), 6108-13.
Hoffmann, E., et al., "Ambisense Approach for the Generation of Influenza A Virus: vRNA and mRNA Synthesis from One Template", Virology, 267, (2000), 310-317.
Hoffmann, E., et al., "Eight-plasmid System for Rapid Generation of Influenza Virus Vaccines", Vaccine, Butterworth Scientific Guildford, 20(25-56), (Aug. 19, 2002), 3165-3170.
Holmes, E. C, et al., "Whole-Genome Analysis of Human Influenza A Virus Reveals Multiple Persistent Lineages and Reassortment Among Recent H3N2 Viruses", PLoS Biology, 3(9), (2005), 1579-1589.
Horimoto, T., et al., "Enhanced growth of seed viruses for H5N1 influenza vaccines", Virology, 366(1), (Sep. 15, 2007), 23-27.
Horimoto, T., et al., "Generation of Influenza A Viruses with Chimeric (Type A/B) Hemagglutinins", Journal of Virology, 77(14), (2003), 8031-8038.
Horimoto, T., et al., "The Development and Characterization of H5 Influenza Virus Vaccines Derived from a 2003 Human Isolate", Vaccine, 24(17), (2006), 3669-3676.
Huang, T.-S., et al., "Determination of Influenza Virus Proteins Required for Genome Replication", Journal of Virology, 64(11), (1990), 5669-5673.
Jang, S.-W., et al., "Deoxygedunin, a Natural Product with Potent Neurotrophic Activity in Mice", PLoS ONE 5(7): e11528, (2010), 1-15.
Kaplan, G., et al., "In vitro Synthesis of Infectious Poliovirus RNA", Proc. Natl. Acad. Sci. USA, 82, (1985), 8824-8428.
Katinger, D., et al., "Attenuated Influenza Viruses as a Vector for Mucosal Immunization Against HIV-1", Vaccines, 97, Cold Spring Harbor, (1997), 315-319.
Kato, A., et al., "Initiation of Sendai Virus Multiplication From Transfected cDNA or RNA With Negative or Positive Sense", Genes to Cells, 1, (1996), 569-579.
Kawaoka, Y., "Mutant Cells With Altered Sialic Acid", U.S. Appl. No. 11/644,179, filed Dec. 22, 2006, 51 pgs.
Kimura, N., et al., "An In Vivo Study of the Replication Origin in the Influenza Virus Complementary RNA", The Journal of Biochemistry, 113(1), (1993), 88-92.
Kimura, N., et al., "Transcription of a Recombinant Influenza Virus RNA in Cells That Can Express the Influenza Virus RNA Polymerase and Nucleoprotein Genes", Journal of General Virology, 73, (1992), 1321-1328.
Kiseleva, I., et al., "Role of individual genes of the A-Leningrad/134/17/57 (H2N2) cold-adapted donor strain in manifestation of the temperature-sensitive phenotype of reassortant influenza A viruses", International Congress Series, vol. 1263, (2004), 547-550.
Kistner, Otfried, et al., "Cell culture (Vero) derived whole virus (H5N1) vaccine based on wild-type virus strain induces cross-protective immune responses", Vaccine, 25(32), (2007), 6028-6036.
Kobayashi, M., et al., "Reconstitution of Influenza Virus RNA Polymerase From Three Subunits Expressed Using Recombinant Baculovirus System", Virus Research, 22, (1992), 235-245.
Konarska, M. M., et al., "Structure of RNAs Replicated by the DNA-Dependent T7 RNA Polymerase", Cell, 63(2), (1990), 609-618.
Kovacova, A., et al., "Sequence similarities and evolutionary relationships of influenza virus A hemagglutinins.", Virus Genes, 24(1), (2002), 57-63.
Krystal, M., et al., "Expression of the Three Influenza Virus Polymerase Proteins in a Single Cell Allows Growth Complementation of Viral Mutants", Proc. Natl. Acad. Sci. USA, 83, (1986), 2709-2713.
Krystal, M., "Influenza B/Lee/40, hemagglutinin (seg 4), complete segment.", Database EM_VI E.B.I. Hinxton U.K., (Apr. 25, 1990).
Kunkel, T. A., "Rapid and Efficient Site-Specific Mutagenesis Without Phenotypic Selection", Proc. Natl. Acad. Sci. USA, 82, (1985), 488-492.
Lamb, Robert A., et al., "Chapter 20—Paramyxoviridae: The Viruses and Their Replication", In: Fundamental Virology, Fields, B. N., et al., editors, Lippincott-Raven (2nd Edition), (1996), 577-647.
Lawson, N. D., "Recombinant Vesicular Stomatitis Viruses From DNA", Proc. Natl. Acad. Sci. USA, 92(10), (1995), 4477-4481.
Lazarovits, Janette, et al., "Endocytosis of Chimeric Influenza Virus Hemaggulutinin Proteins That Lack a Cytoplasmic Recognition Feature for Coated Pits", The Journal of Cell Biology, vol. 134, No. 2, (1996), 339-348.
Lee, C. W, et al., "Generation of reassortant influenza vaccines by reverse genetics that allows utilization of a DIVA (Differentiating Infected from Vaccinated Animals) strategy for the control of avian influenza", Vaccine, vol. 22, (2004), 3175-3181.
Lee, Dong-Hun, et al., "Progress and hurdles in development of influenza virus-like particle vaccines for veterinary use", Korean Vaccine Society, (2014), 133-139.
Lee, M. S, et al., "Genetic and pathogenic characterization of H6NI avian influenza viruses isolated in Taiwan between 1972 and 2005", Avian Diseases, 50(4), (Dec. 2006), 561-571.
Levis, R., et al., "Deletion Mapping of Sindbis Virus DI RNAs Derived From cDNAs Defines the Sequences Essential for Replication and Packaging", Cell, 44, (1986), 137-145.
Li, K. S, et al., "Genesis of a highly pathogenic and potentially pandemic H5NI influenza virus in eastern Asia", Nature, 430(6996), (Jul. 8, 2004), 209-213.

(56) References Cited

OTHER PUBLICATIONS

Lin, Y P, et al., "Adaptation of egg-grown and transfectant influenza viruses for growth in mammalian cells: selection of hemagglutinin mutants with elevated pH of membrane fusion", Virology, vol. 233, No. 2, (1997), 402-410.
Luytjes, W., "Amplification, Expression, and Packaging of a Foreign Gene by Influenza Virus", Cell, 59(6), (1989), 1107-1113.
Matsuoka, et al., "Neuraminidase Stalk Length and Additional Glycosylation of the Hemagglutinin Influence the Virulence of Influenza H5N1 Viruses for Mice", Journal of Virology, vol. 83, No. 9 (2009), pp. 4704-4708.
Mena, I., et al., "Synthesis of Biologically Active Influenza Virus Core Proteins Using a Vaccinia Virus-T7 RNA Polymerase Expression System", Journal of General Virology, 75, (1994), 2109-2114.
Moyer, S. A., et al., "Assembly and Transcription of Synthetic Vesicular Stomatitis Virus Nucleocapsids", Journal of Virology, 65(5), (1991), 2170-2178.
Murakami, Shin, et al., "Growth Determinants for H5N1 Influenza Vaccine Seed Viruses in MDCK Cells", Journal of Virology, vol. 82, No. 21, (Nov. 2008), 10502-10509.
Naito, S., et al., "Function and Structure of RNA Polymerase From Vesicular Stomatitis Virus", The Journal of Biological Chemistry, 251(14), (1976), 4307-4314.
Nara, P. L., et al., "Simple, Rapid, Quantitative, Syncytium-Forming Microassay for the Detection of Human Immunodeficiency Virus Neutralizing Antibody", Aids Research and Human Retroviruses, 3(3), (1987), 283-302.
Nemeroff, M. E., et al., "Influenza Virus NS1 Protein Interacts With the Cellular 30 kDa Subunit of CPSF and Inhibits 3' End Formation of Cellular Pre-mRNAs", Molecular Cell, 1(7), (1998), 991-1000.
Neumann, G., et al., "An Improved Reverse Genetics System for Influenza A Virus Generation and Its Implications for Vaccine Production", Proc. Natl. Acad. Sci. USA, 102(46), (2005), 16825-16829.
Neumann, G., et al., "Emergence and pandemic potential of swine-origin HlN1 influenza virus", Nature (London), 459(7249), (Jun. 2009), 931-939.
Neumann, G., et al., "Generation of influenza A virus from cloned cDNAs—historical perspective and outlook for the new millenium.", Rev Med Virol., 12(1), XP002314285, (Jan.-Feb. 2002), 13-30.
Neumann, G., et al., "Reverse Genetics of Influenza Viruses—Applications in Research and Vaccine Design", Monographs in Virology, 27, (2008), 118-133.
Odagiri, T., et al., "Nucleotide Sequence of the PA Gene of Influenza A/WSN/33 (H1N1)", Nucleic Acids Research, 18 (3), Department of Virology, (Jan. 9, 1990).
Orkin, S. H, et al., "Report and Recommendations of the Panel to Assess the NIH Investment in Research on Gene Therapy", http://www.nih.gov/news/panelrep.html, (Dec. 7, 1995), 37 pgs.
Palese, P., "Negative-Strand RNA Viruses: Genetic Engineering and Applications", Proc. Natl. Acad. Sci. USA, 93(21), (1996), 11354-11358.
Park, K. H., et al., "Rescue of a Foreign Gene by Sendai Virus", Proc. Natl. Acad. Sci. USA, 88, (1991), 5537-5541.
Pattnaik, A. K., et al., "Cells That Express All Five Proteins of Vesicular Stomatitis Virus From Cloned cDNAs Support Replication, Assembly, and Budding of Defective Interfering Particles", Proc. Natl. Acad. Sci. USA, 88(4), (1991), 1379-1383.
Peeters, B. P. H., et al., "Rescue of Newcastle Disease Virus From Cloned cDNA: Evidence That Cleavability of the Fusion Protein Is a Major Determinant for Virulence", Journal of Virology, 73(6), (1999), 5001-5009.
Pekosz, A., "Commentary—Reverse Genetics of Negative-Strand RNA Viruses: Closing the Circle", Proc. Natl. Acad. Sci. USA, 96, (1999), 8804-8806.
Percy, N., et al., "Expression of a Foreign Protein by Influenza A Virus", Journal of Virology, 68(7), (1994), 4486-4492.
Qiu, Y., et al., "The Influenza Virus NS1 Protein Binds to a Specific Region in Human U6 snRNA and Inhibits U6-U2 and U6-U4 snRNA Interactions During Splicing", RNA, 1, (1995), 304-316.

Qiu, Y., et al., "The Influenza Virus NS1 Protein Is a Poly(A)-Binding Protein That Inhibits Nuclear Export of mRNAs Containing Poly(A)", Journal of Virology, 68(4), (1994), 2425-2432.
Racaniello, V. R., et al., "Cloned Poliovirus Complimentary DNA Is Infectious in Mammalian Cells", Science, 214, (1981).
Radecke, F., et al., "Rescue of Measles Viruses From Cloned DNA", The EMBO Journal, 14(23), (1995), 5773-5784.
Radecke, F., et al., "Reverse Genetics Meets the Nonsegmented Negative-Strand RNA Viruses", Reviews in Medical Virology, 7, (1997), 49-63.
Reed, M. L, et al., "Amino Acid Residues in the Fusion peptide Pocket Regulate the pH of Activation of the H5N1 Influenza Virus Hemagglutinin Protein", . J. Virol., 83(8), (2009), 3568-3580.
Roberts, A., et al., "Minireview—Recovery of Negative-Strand RNA Viruses From Plasmid DNAs: A Positive Approach Revitalizes a Negative Field", Virology, 247(1), (1998), 1-6.
Romanova, J., et al., "Live cold-adapted influenza A vaccine produced in Vero cell line", Virus Research, 103, (2004), 187-193.
Rose, J. K., "Positive Strands to the Rescue Again: A Segmented Negative-Strand RNA Virus Derived From Cloned cDNAs", Proc. Natl. Acad. Sci. USA, 94, (1996), 14998-15000.
Schickli, J. H, et al., "Plasmid-only Rescue of Influenza A Virus Vaccine Candidates", Philosophical Transactions of the Royal Society of London. Series B, Biological Sciences, 356(1416), (Dec. 29, 2001), 1965-1973.
Schlesinger, S., "RNA Viruses as Vectors for the Expression of Heterologous Proteins", Molecular Biotechnology, 3(2), (1995), 155-165.
Schnell, M. J., "Infectious Rabies Viruses From Cloned cDNA", The EMBO Journal, 13(18), (1994), 4195-4203.
Schotsaert, M, et al., "Universal M2 ectodomain-based influenza A vaccines: preclinical and clinical developments", Expert Rev V accines. Apr. 2009;8(4):, 499-508.
Seong, B. L., et al., "A New Method for Reconstituting Influenza Polymerase and RNA in Vitro: A Study of the Promoter Elements for cRNA and vRNA Synthesis in Vitro and Viral Rescue in Vivo", Virology, 186(1), (1992), 247-260.
Sidhu, M. S., et al., "Rescue of Synthetic Measles Virus Minireplicons: Measles Genomic Termini Direct Efficient Expression and Propagation of a Reporter Gene", Virology, 208, (1995), 800-807.
Smeenk, et al., "Mutations in the Hemagglutinin and Matrix Genes of a Virulent Influenza Virus Variant, A/FM/1/47-MA, Control Different Stages in Pathogenesis", Virus Research 44, (1996), 79-95.
Subbarao, E. K., et al., "Sequential Addition of Temperature-Sensitive Missense Mutations into the PB2 Gene of Influenza A Transfectant Viruses Can Effect an Increase in Temperature Sensitivity and Attenuation and Permits the Rational Design of a Genetically Engineered Live Influen", Journal of Virology, 69(10), (1995), 5969-5977.
Subbarao, K., et al., "Evaluation of a Genetically Modified Reassortant H5N1 Influenza A Virus Vaccine Candidate Generated by Plasmid-based Reverse Genetics", Virology, vol. 305(1), (Jan. 5, 2003), 192-200.
Szewczyk, B., "Purification, Thioredoxin Renaturation, and Reconstituted Activity of the Three Subunits of the Influenza A Virus RNA Polymerase", Proc. Natl. Acad. Sci. USA, 85, (1988), 7907-7911.
Taylor, J., et al., "Newcastle Disease Virus Fusion Protein Expressed in a Fowlpox Virus Recombinant Confers Protection in Chickens", Journal of Virology, 64(4), (1990), 1441-1450.
Verma, I. M, et al., "Gene Therapy—Promises, Problems and Prospects", Nature, 389, (1997), 239-242.
Voeten, J. T, et al., "Characterization of high-growth reassortant influenza A viruses generated in MDCK cells cultured in serum-free medium", Vaccine, vol. 17, (1999), 1942-1950.
Ward, C. D., et al., "Direct Measurement of the Poliovirus RNA Polymerase Error Frequency In Vitro", Journal of Virology, 62(2), (1988), 558-562.
Watanabe, et al., "Novel Approach to the Development of Effective H5N1 In?uenza A Virus Vaccines: Use of M2 Cytoplasmic Tail Mutants", Journal of Virology, 82(5), (2008), 2486-2492.

(56) References Cited

OTHER PUBLICATIONS

Whelan, S. P. J., et al., "Efficient Recovery of Infectious Vesicular Stomatitis Virus Entirely from cDNA Clones", Proc. Natl. Acad. Sci. USA, 92, (1995), 8388-8392.

Winter, G., et al., "The use of synthetic oligodeoxynucleotide primers in cloning and sequencing segment 8 of influenza virus (A/PR/8/34)", Nucleic Acids Res., 9(2), (1981), 237-245.

Wu, Rui, et al., "A live bivalent influenza vaccine based on a H9N2 virus strain", Vaccine, 28, (2010), 673-680.

Xu, X., et al., "Reassortment and evolution of current human influenza A and B viruses", Virus Research, 103, (2004), 55-60.

Yamanaka, K., et al., "In vivo Analysis of the Promoter Structure of the Influenza Virus RNA Genome Using a Transfection System With an Engineered RNA", Proc. Natl. Acad. Sci. USA, 88, (1991), 5369-5373.

Yannarell, Dean A., et al., "Factors affecting the yield of cold-adapted influenza virus vaccine", Journal of Virological Methods, vol. 64, 161-169, (1997), 1 pg.

Yi, Pu Lin, et al., "Adaptation of Egg-Grown and Transfectant Influenza Viruses for Growth in Mammalian Cells: Selection of Hemagglutinin Mutants with Elevated pH of Membrane Fusion", Virology, 233(2), (Jul. 7, 1997), 402-410.

Yu, Q., et al., "Functional cDNA Clones of the Human Respiratory Syncytial (RS) Virus N, P, and L Proteins Support Replication of RS Virus Genomic RNA Analogs and Define Minimal trans-Acting Requirements for RNA Replication", Journal of Virology, 69(4), (1995), 2412-2419.

Yusoff, K., et al., "Nucleotide Sequence Analysis of the L Gene of Newcastle Disease Virus: Homologies With Sendai and Vesicular Stomatitis Viruses", Nucleic Acids Research, 15(10), (1987), 3961-3976.

Zaghouani, H, et al., "Induction of Antibodies to the Envelope Protein of the Human Immunodeficiency Virus by Immunization With Monoclonal Anti-Idiotypes", Proc. Natl. Acad. Sci. USA, 88, (1991), 5645-5649.

Zaghouani, H., et al., "Cells Expressing an H Chain 1g Gene Carrying a Viral T Cell Epitope are Lysed by Specific Cytolytic T Cells", The Journal of Immunology, 148(11), (1992), 3604-3609.

Zhang, H., et al., "Expression of Functional Influenza Virus A Polymerase Proteins and Template From Cloned cDNAs in Recombinant Vaccinia Virus Infected Cells", Biochemical and Biophysical Research Communications, 200(1), (1994), 95-101.

Zobel, A., et al., "RNA Polymerase I Catalysed Transcription of Insert Viral cDNA", Nucleic Acids Research, 21(16), (1993), 3607-3614.

"U.S. Appl. No. 13/070,110, Examiner Interview Summary dated Jan. 16, 2018", 3 pgs.

"U.S. Appl. No. 13/070,110, Notice of Allowance dated Mar. 26, 2018", 6 pgs.

"U.S. Appl. No. 13/070,110, Response filed Jan. 22, 2018 to Non Final Office Action dated Jul. 21, 2017", 10 pgs.

"U.S. Appl. No. 15/593,039, Non Final Office Action dated Feb. 6, 2018", 8 pgs.

"U.S. Appl. No. 15/593,039, Response filed Apr. 30, 2018 to Non Final Office Action dated Feb. 4, 2018", 8 pgs.

Elhefnavvi, M, et al., "Identification of novel conserved functional motifs across most Influenza A viral strains", Virol J. Jan. 27, 2011;8:44. doi: 10.1186/1743-422X-8-44, (2011), 2 pgs.

Gorman, O T, "Evolution of influenza A virus PB2 genes: implications for evolution of the ribonucleoprotein complex and origin of human influenza A virus", Department of Virology and Molecular Biology, St. Jude Children's Research Hospital, Memphis Tennessee 38101-0318 J. Virol, Oct. 1990; 640(10):4893-902, (1990), 2 pgs.

PolI-5'WPB2 (SEQ ID NO: 14)
CAC ACA *CGT CTC* GTA TTA GTA GAA ACA AGG TCG TTT TTA AAC TAT TCG
ACA CTA ATT GAT GGC CAT CCG AAT TCT TTT GG
Length: 80 nt                    Overlap: 26 nt PolI-3'WPB2 (SEQ ID NO: 20)
CAC ACA *CGT CTC* CGG GAG CGA AAG CAG GTC AAT TAT ATT CAA TAT GGA
AAG AAT AAA AGA ACT AAG G
Length: 67 nt                    Overlap: 24 nt PolI-5'WPB1 (SEQ ID NO: 21)
CAC ACA *CGT CTC* GTA TTA GTA GAA ACA AGG CAT TTT TTC ATG AAG GAC
AAG CTA AAT TCA CTA TTT TTG CCG TCT GAG CTC TTC AAT GG
Length: 89                       Overlap: 26 nt PolI-3'WPB1 (SEQ ID NO: 22)
CAC ACA *CGT CTC* CGG GAG CGA AAG CAG GCA AAC CAT TTG AAT GGA TGT
CAA TCC GAC TTT ACT TTT C
Length: 67 nt                    Overlap: 27 nt PolI-5'WPA (SEQ ID NO: 23)
CCA ACC *CGT CTC* CTA TTA GTA GAA ACA AGG TAC TTT TTT GGA CAG TAT
GGA TAG CAA ATA GTA GCA TTG CCA CAA CTA TCT CAA TGC ATG TGT GAG
GAA GGA G
Length: 103                      Overlap: 25 nt PolI-3'WPA (SEQ ID NO: 24)
CCA ACC *CGT CTC* CGG GAG CGA AAG CAG GTA CTG ATT CAA AAT GGA AGA
TTT TGT GCG ACA ATG CTT C
Length: 67 nt                    Overlap: 27 nt PolI-5'WHA (SEQ ID NO: 25)
CAC ACA *CGT CTC* CTA TTA GTA GAA ACA AGG GTG TTT TTC C
Length: 40 nt                    Overlap: 22 nt PolI-3'WHA (SEQ ID NO: 26)
CAC ACA *CGT CTC* CGG GAG CAA AAG CAG GGG AAA AT  AAA AAC AAC C
Length: 46 nt                    Overlap: 29 nt

*FIG. 6A*

PolI-5'WNP (SEQ ID NO: 27)
CAC ACA *CGT CTC* CTA TTA GTA GAA ACA AGG GTA TTT TTC TTT AAT TG
Length: 47 nt          Overlap: 30 nt PolI-3'WNP (SEQ ID NO: 28)
CAC ACA *CGT CTC* CGG GAG CAA AAG CAG GGT AGA TAA TCA CTC
Length: 42 nt          Overlap: 26 nt PolI-5'WNA (SEQ ID NO: 29)
CAC ACA *CGT CTC* CTA TTA GTA GAA ACA AGG AGT TTT TTG AAC AAA C
Length: 46 nt          Overlap: 29 nt PolI-3'WNA (SEQ ID NO: 30)
CAC ACA *CGT CTC* CGG GAG CGA AAG CAG GAG TTT AAA TGA ATC CAA ACC
Length: 48 nt          Overlap: 32 nt PolI-5'WM (SEQ ID NO: 31)
CAC ACA *CGT CTC* CTA TTA GTA GAA ACA AGG TAG TTT TTT ACT CCA GC
Length: 47 nt          Overlap: 30 nt PolI-3'WM (SEQ ID NO: 32)
CAC ACA *CGT CTC* CGG GAG CAA AAG CAG GTA GAT ATT GAA AG
Length: 41 nt          Overlap: 26 nt PolI-5'WNS (SEQ ID NO: 33)
CAC ACA *CGT CTC* CTA TTA GTA GAA ACA AGG GTG TTT TTT ATT ATT AAA TAA GC
Length: 53 nt          Overlap: 36 nt PolI-3'WNS (SEQ ID NO: 34)
CAC ACA *CGT CTC* CGG GAG CAA AAG CAG GGT GAC AAA GAC ATA ATG G
Length: 46 nt          Overlap: 30 nt Italics:            BsmBI recognition sequence
Underlined:         Influenza virus sequence
Underlined + Bold:  Influenza virus coding region

*FIG. 6B*

|  | | NO. OF SURVIVORS/NO. OF TESTED [a] | |
| --- | --- | --- | --- |
| VACCINE | | CHALLENGE VIRUS | |
| | | VN1203 | INDONESIA 7 |
| M2del11-HAavir | 100 PFU | 8/8 | 8/8 |
| | 1000 PFU | 8/8 | 8/8 |
| PBS | | 0/8 | 0/8 |

FIG. 12

SEQUENCE LISTING

<160> NUMBER OF SEQ ID NOS: 53

<210> SEQ ID NO 1
<211> LENGTH: 19
<212> TYPE: DNA
<213> ORGANISM: Artificial Sequence
<220> FEATURE:
<223> OTHER INFORMATION: A synthetic primer

<400> SEQUENCE: 1
aagagggtca cttgaatcg                                                  19

<210> SEQ ID NO 2
<211> LENGTH: 18
<212> TYPE: DNA
<213> ORGANISM: Artificial Sequence
<220> FEATURE:
<223> OTHER INFORMATION: A synthetic primer

<400> SEQUENCE: 2
actgttgctg cgagtatc                                                   18

<210> SEQ ID NO 3
<211> LENGTH: 18
<212> TYPE: DNA
<213> ORGANISM: Artificial Sequence
<220> FEATURE:
<223> OTHER INFORMATION: A synthetic primer

<400> SEQUENCE: 3
gttgttgctc caactatc 18

<210> SEQ ID NO 4
<211> LENGTH: 18
<212> TYPE: DNA
<213> ORGANISM: Artificial Sequence
<220> FEATURE:
<223> OTHER INFORMATION: A synthetic primer

<400> SEQUENCE: 4
gttgttgctg cgaacatc 18

<210> SEQ ID NO 5
<211> LENGTH: 22
<212> TYPE: DNA
<213> ORGANISM: Artificial Sequence
<220> FEATURE:
<223> OTHER INFORMATION: A synthetic primer

<400> SEQUENCE: 5
gttgttatca ttgggatctt gc 22

<210> SEQ ID NO 6
<211> LENGTH: 18
<212> TYPE: DNA
<213> ORGANISM: Artificial Sequence
<220> FEATURE:
<223> OTHER INFORMATION: A synthetic primer

<400> SEQUENCE: 6
cccaatgata ctcgcagc 18

<210> SEQ ID NO 7
<211> LENGTH: 25
<212> TYPE: DNA
<213> ORGANISM: Artificial Sequence
<220> FEATURE:
<223> OTHER INFORMATION: A synthetic primer

<400> SEQUENCE: 7
atcttgcact tgatattggc aattc 25

<210> SEQ ID NO 8
<211> LENGTH: 62
<212> TYPE: DNA
<213> ORGANISM: Artificial Sequence
<220> FEATURE:
<223> OTHER INFORMATION: A synthetic primer

<400> SEQUENCE: 8
caccagtgaa ctggcgacag ttgagtagat cgccagaatg tcacttgaat cgttgcatct 60
gc 62

<210> SEQ ID NO 9
<211> LENGTH: 57
<212> TYPE: DNA
<213> ORGANISM: Artificial Sequence
<220> FEATURE:
<223> OTHER INFORMATION: A synthetic primer

<400> SEQUENCE: 9
cttttggtct ccctgggggc aatcagtttc tgatggatc gtcttttttt caaatgc 57

<210> SEQ ID NO 10
<211> LENGTH: 68

```
<212> TYPE: DNA
<213> ORGANISM: Artificial Sequence
<220> FEATURE:
<223> OTHER INFORMATION: A synthetic primer

<400> SEQUENCE: 10
gcttagtatc aattgtattc catttatgat tgatatccaa atgctgtcac ttgaatcgtt    60
gcatctgc                                                             68

<210> SEQ ID NO 11
<211> LENGTH: 63
<212> TYPE: DNA
<213> ORGANISM: Artificial Sequence
<220> FEATURE:
<223> OTHER INFORMATION: A synthetic primer

<400> SEQUENCE: 11
attataggag tcgtaatgtg tatctcaggg attaccataa tagatcgtct ttttttcaaa    60
tgc                                                                  63

<210> SEQ ID NO 12
<211> LENGTH: 33
<212> TYPE: DNA
<213> ORGANISM: Artificial Sequence
<220> FEATURE:
<223> OTHER INFORMATION: A synthetic oligonucleotide

<400> SEQUENCE: 12
gggttattgg agacggtacc gtctcctccc ccc                                 33

<210> SEQ ID NO 13
<211> LENGTH: 18
<212> TYPE: DNA
<213> ORGANISM: Artificial Sequence
<220> FEATURE:
<223> OTHER INFORMATION: A synthetic oligonucleotide
<220> FEATURE:
<221> NAME/KEY: misc_feature
<222> LOCATION: 7
<223> OTHER INFORMATION: n = A, T, G, or C

<400> SEQUENCE: 13
cgtctcntat tagtagaa                                                  18

<210> SEQ ID NO 14
<211> LENGTH: 16
<212> TYPE: DNA
<213> ORGANISM: Artificial Sequence
<220> FEATURE:
<223> OTHER INFORMATION: A synthetic oligonucleotide
<220> FEATURE:
<221> NAME/KEY: misc_feature
<222> LOCATION: 11
<223> OTHER INFORMATION: n = A, T, G, or C

<400> SEQUENCE: 14
ttttgctccc ngagac                                                    16

<210> SEQ ID NO 15
<211> LENGTH: 11
<212> TYPE: DNA
<213> ORGANISM: Artificial Sequence
<220> FEATURE:
<223> OTHER INFORMATION: A synthetic oligonucleotide

<400> SEQUENCE: 15
```

```
tattagtaga a                                                          11

<210> SEQ ID NO 16
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 16
gggagcaaaa                                                            10

<210> SEQ ID NO 17
<211> LENGTH: 15
<212> TYPE: DNA
<213> ORGANISM: Artificial Sequence
<220> FEATURE:
<223> OTHER INFORMATION: A synthetic oligonucleotide

<400> SEQUENCE: 17
gggttattag tagaa                                                      15

<210> SEQ ID NO 18
<211> LENGTH: 13
<212> TYPE: DNA
<213> ORGANISM: Artificial Sequence
<220> FEATURE:
<223> OTHER INFORMATION: A synthetic oligonucleotide

<400> SEQUENCE: 18
ttttgctccc ccc                                                        13

<210> SEQ ID NO 19
<211> LENGTH: 80
<212> TYPE: DNA
<213> ORGANISM: Artificial Sequence
<220> FEATURE:
<223> OTHER INFORMATION: A synthetic primer

<400> SEQUENCE: 19
cacacacgtc tcgtattagt agaaacaagg tcgtttttaa actattcgac actaattgat     60
ggccatccga attcttttgg                                                 80

<210> SEQ ID NO 20
<211> LENGTH: 67
<212> TYPE: DNA
<213> ORGANISM: Artificial Sequence
<220> FEATURE:
<223> OTHER INFORMATION: A synthetic primer

<400> SEQUENCE: 20
cacacacgtc tccgggagcg aaagcaggtc aattatattc aatatggaaa gaataaaaga     60
actaagg                                                               67

<210> SEQ ID NO 21
<211> LENGTH: 89
<212> TYPE: DNA
<213> ORGANISM: Artificial Sequence
<220> FEATURE:
<223> OTHER INFORMATION: A synthetic primer

<400> SEQUENCE: 21
cacacacgtc tcgtattagt agaaacaagg catttttca tgaaggacaa gctaaattca      60 ctattttgc cgtctgagct cttcaatgg                                        89
```

<210> SEQ ID NO 22
<211> LENGTH: 67
<212> TYPE: DNA
<213> ORGANISM: Artificial Sequence
<220> FEATURE:
<223> OTHER INFORMATION: A synthetic primer

<400> SEQUENCE: 22
cacacacgtc tccgggagcg aaagcaggca aaccatttga atggatgtca atccgacttt    60
acttttc                                                              67

<210> SEQ ID NO 23
<211> LENGTH: 103
<212> TYPE: DNA
<213> ORGANISM: Artificial Sequence
<220> FEATURE:
<223> OTHER INFORMATION: A synthetic primer

<400> SEQUENCE: 23
ccaacccgtc tcctattagt agaaacaagg tacttttttg gacagtatgg atagcaaata    60
gtagcattgc cacaactatc tcaatgcatg tgtgaggaag gag                      103

<210> SEQ ID NO 24
<211> LENGTH: 67
<212> TYPE: DNA
<213> ORGANISM: Artificial Sequence
<220> FEATURE:
<223> OTHER INFORMATION: A synthetic primer

<400> SEQUENCE: 24
ccaacccgtc tccgggagcg aaagcaggta ctgattcaaa atggaagatt ttgtgcgaca    60
atgcttc                                                              67

<210> SEQ ID NO 25
<211> LENGTH: 40
<212> TYPE: DNA
<213> ORGANISM: Artificial Sequence
<220> FEATURE:
<223> OTHER INFORMATION: A synthetic primer

<400> SEQUENCE: 25
cacacacgtc tcctattagt agaaacaagg gtgttttcc                            40

<210> SEQ ID NO 26
<211> LENGTH: 45
<212> TYPE: DNA
<213> ORGANISM: Artificial Sequence
<220> FEATURE:
<223> OTHER INFORMATION: A synthetic primer

<400> SEQUENCE: 26
cacacacgtc tccgggagca aaagcagggg aaaataaaaa caacc                     45

<210> SEQ ID NO 27
<211> LENGTH: 47
<212> TYPE: DNA
<213> ORGANISM: Artificial Sequence
<220> FEATURE:
<223> OTHER INFORMATION: A synthetic primer

<400> SEQUENCE: 27
cacacacgtc tcctattagt agaaacaagg gtattttttct ttaattg                  47

<210> SEQ ID NO 28
<211> LENGTH: 42
<212> TYPE: DNA
<213> ORGANISM: Artificial Sequence
<220> FEATURE:
<223> OTHER INFORMATION: A synthetic primer

<400> SEQUENCE: 28
cacacacgtc tccgggagca aaagcagggt agataatcac tc           42

<210> SEQ ID NO 29
<211> LENGTH: 46
<212> TYPE: DNA
<213> ORGANISM: Artificial Sequence
<220> FEATURE:
<223> OTHER INFORMATION: A synthetic primer

<400> SEQUENCE: 29
cacacacgtc tcctattagt agaaacaagg agttttttga acaaac       46

<210> SEQ ID NO 30
<211> LENGTH: 48
<212> TYPE: DNA
<213> ORGANISM: Artificial Sequence
<220> FEATURE:
<223> OTHER INFORMATION: A synthetic primer

<400> SEQUENCE: 30
cacacacgtc tccgggagcg aaagcaggag tttaaatgaa tccaaacc     48

<210> SEQ ID NO 31
<211> LENGTH: 47
<212> TYPE: DNA
<213> ORGANISM: Artificial Sequence
<220> FEATURE:
<223> OTHER INFORMATION: A synthetic primer

<400> SEQUENCE: 31
cacacacgtc tcctattagt agaaacaagg tagttttttta ctccagc     47

<210> SEQ ID NO 32
<211> LENGTH: 41
<212> TYPE: DNA
<213> ORGANISM: Artificial Sequence
<220> FEATURE:
<223> OTHER INFORMATION: A synthetic primer

<400> SEQUENCE: 32
cacacacgtc tccgggagca aaagcaggta gatattgaaa g            41

<210> SEQ ID NO 33
<211> LENGTH: 53
<212> TYPE: DNA
<213> ORGANISM: Artificial Sequence
<220> FEATURE:
<223> OTHER INFORMATION: A synthetic primer

<400> SEQUENCE: 33
cacacacgtc tcctattagt agaaacaagg gtgttttttta ttattaaata agc   53

<210> SEQ ID NO 34
<211> LENGTH: 46
<212> TYPE: DNA
<213> ORGANISM: Artificial Sequence
<220> FEATURE:
<223> OTHER INFORMATION: A synthetic primer

```
<400> SEQUENCE: 34
cacacacgtc tccgggagca aaagcagggt gacaaagaca taatgg            46

<210> SEQ ID NO 35
<211> LENGTH: 28
<212> TYPE: DNA
<213> ORGANISM: Artificial Sequence
<220> FEATURE:
<223> OTHER INFORMATION: A synthetic primer

<400> SEQUENCE: 35
gtgaatagaa ttggagtaaa aaactacc                                28

<210> SEQ ID NO 36
<211> LENGTH: 27
<212> TYPE: DNA
<213> ORGANISM: Artificial Sequence
<220> FEATURE:
<223> OTHER INFORMATION: A synthetic primer

<400> SEQUENCE: 36
tcaaaaatga ccatcgtcaa catccac                                 27

<210> SEQ ID NO 37
<211> LENGTH: 28
<212> TYPE: DNA
<213> ORGANISM: Artificial Sequence
<220> FEATURE:
<223> OTHER INFORMATION: A synthetic primer

<400> SEQUENCE: 37
gtgagatggt cattttgtca acatagaa                                28

<210> SEQ ID NO 38
<211> LENGTH: 27
<212> TYPE: DNA
<213> ORGANISM: Artificial Sequence
<220> FEATURE:
<223> OTHER INFORMATION: A synthetic primer

<400> SEQUENCE: 38
tcaatccaca gcactctgct gttcctg                                 27

<210> SEQ ID NO 39
<211> LENGTH: 26
<212> TYPE: DNA
<213> ORGANISM: Artificial Sequence
<220> FEATURE:
<223> OTHER INFORMATION: A synthetic primer

<400> SEQUENCE: 39
gtgacggcag gaacagcaga gtgctg                                  26

<210> SEQ ID NO 40
<211> LENGTH: 25
<212> TYPE: DNA
<213> ORGANISM: Artificial Sequence
<220> FEATURE:
<223> OTHER INFORMATION: A synthetic primer

<400> SEQUENCE: 40
tcattccctc atagactcag gtacc                                   25

<210> SEQ ID NO 41
```

```
<211> LENGTH: 25
<212> TYPE: DNA
<213> ORGANISM: Artificial Sequence
<220> FEATURE:
<223> OTHER INFORMATION: A synthetic primer

<400> SEQUENCE: 41
gtgagcaggg gtacctgagt ctatg                                          25

<210> SEQ ID NO 42
<211> LENGTH: 24
<212> TYPE: DNA
<213> ORGANISM: Artificial Sequence
<220> FEATURE:
<223> OTHER INFORMATION: A synthetic primer

<400> SEQUENCE: 42
tcaaggccct cttttcaaac cgta                                           24

<210> SEQ ID NO 43
<211> LENGTH: 29
<212> TYPE: DNA
<213> ORGANISM: Artificial Sequence
<220> FEATURE:
<223> OTHER INFORMATION: A synthetic primer

<400> SEQUENCE: 43
cttaaatacg gtttgaaaag agggcctgc                                      29

<210> SEQ ID NO 44
<211> LENGTH: 34
<212> TYPE: DNA
<213> ORGANISM: Artificial Sequence
<220> FEATURE:
<223> OTHER INFORMATION: A synthetic primer

<400> SEQUENCE: 44
tcactcaata aatgcatttg aagaaaagac gatc                                34

<210> SEQ ID NO 45
<211> LENGTH: 26
<212> TYPE: DNA
<213> ORGANISM: Artificial Sequence
<220> FEATURE:
<223> OTHER INFORMATION: A synthetic primer

<400> SEQUENCE: 45
ttgttgttgc cgcaaatatc attggg                                         26

<210> SEQ ID NO 46
<211> LENGTH: 28
<212> TYPE: DNA
<213> ORGANISM: Artificial Sequence
<220> FEATURE:
<223> OTHER INFORMATION: A synthetic primer

<400> SEQUENCE: 46
ttcactcaac ttgaatcgct gcatctgc                                       28

<210> SEQ ID NO 47
<211> LENGTH: 10
<212> TYPE: PRT
<213> ORGANISM: Artificial Sequence
<220> FEATURE:
<223> OTHER INFORMATION: A synthetic oligopeptide
<220> FEATURE:
<221> NAME/KEY: SITE
```

```
<222> LOCATION: 10
<223> OTHER INFORMATION: Xaa = R or G

<400> SEQUENCE: 47

Pro Gln Arg Glu Arg Arg Arg Lys Lys Xaa
1               5                   10

<210> SEQ ID NO 48
<211> LENGTH: 6
<212> TYPE: PRT
<213> ORGANISM: Artificial Sequence
<220> FEATURE:
<223> OTHER INFORMATION: A synthetic oligopeptide
<220> FEATURE:
<221> NAME/KEY: SITE
<222> LOCATION: 6
<223> OTHER INFORMATION: Xaa = R or G

<400> SEQUENCE: 48

Pro Gln Arg Glu Thr Xaa
1               5

<210> SEQ ID NO 49
<211> LENGTH: 16
<212> TYPE: DNA
<213> ORGANISM: Artificial Sequence
<220> FEATURE:
<223> OTHER INFORMATION: A synthetic oligopeptide
<220> FEATURE:
<221> NAME/KEY: misc_feature
<222> LOCATION: 6
<223> OTHER INFORMATION: n = A, T, G, or C

<400> SEQUENCE: 49
gtctcnggga gcaaaa                                                       16

<210> SEQ ID NO 50
<211> LENGTH: 15
<212> TYPE: DNA
<213> ORGANISM: Artificial Sequence
<220> FEATURE:
<223> OTHER INFORMATION: A synthetic oligopeptide

<400> SEQUENCE: 50
ttctactaat aaccc                                                        15

<210> SEQ ID NO 51
<211> LENGTH: 13
<212> TYPE: DNA
<213> ORGANISM: Artificial Sequence
<220> FEATURE:
<223> OTHER INFORMATION: A synthetic oligopeptide

<400> SEQUENCE: 51 gggggggagca aaa                                                         13

<210> SEQ ID NO 52
<211> LENGTH: 33
<212> TYPE: DNA
<213> ORGANISM: Artificial Sequence
<220> FEATURE:
<223> OTHER INFORMATION: A synthetic oligopeptide

<400> SEQUENCE: 52 gggggggagga gacggtaccg tctccaataa ccc                                   33

<210> SEQ ID NO 53
```

```
<211> LENGTH: 18
<212> TYPE: DNA
<213> ORGANISM: Artificial Sequence
<220> FEATURE:
<223> OTHER INFORMATION: A synthetic oligopeptide
<220> FEATURE:
<221> NAME/KEY: misc_feature
<222> LOCATION: 12
<223> OTHER INFORMATION: n = A, T, G, or C

<400> SEQUENCE: 53
ttctactaat angagacg                                                  18
```

INFLUENZA M2 PROTEIN MUTANT VIRUSES AS LIVE INFLUENZA ATTENUATED VACCINES

CROSS-REFERENCE TO RELATED APPLICATIONS

This application is a continuation of U.S. patent application Ser. No. 12/214,414, filed Jun. 18, 2008, which application claims the benefit of the filing date of U.S. application Ser. No. 60/944,680, filed on Jun. 18, 2007, the disclosures of which are incorporated by reference herein.

STATEMENT OF GOVERNMENT RIGHTS

This invention was made with government support under AI044386 awarded by the National Institutes of Health. The Government has certain rights in the invention.

BACKGROUND

Generally, influenza vaccines have been prepared from live, attenuated virus or killed virus which can grow to high titers. Live virus vaccines activate all phases of the immune system and stimulate an immune response to each of the protective antigens, which obviates difficulties in the selective destruction of protective antigens that may occur during preparation of inactivated vaccines. In addition, the immunity produced by live virus vaccines is generally more durable, more effective, and more cross-reactive than that induced by inactivated vaccines. Further, live virus vaccines are less costly to produce than inactivated virus vaccines. However, the mutations in attenuated virus are often ill-defined.

In 1997, a highly pathogenic avian influenza virus (H5N1 subtype) was transmitted from chickens to humans in Hong Kong, killing 6 of 18 people infected (Claas et al., 1998; Subbarao et al., 1998). The recent H5N1 outbreaks in poultry, which began in late 2003, affected more than 10 Asian countries, and viruses have now been isolated from wild birds and poultry in Asia. Europe, and Africa (Li et al., 2004; WHO, 2006). The continued circulation of H5N1 viruses in birds provides ample opportunity for them to infect humans. Indeed, human cases of H5N1 infections have been observed in several countries since late 2003, with a total of 321 confirmed cases and 194 fatalities as of 16 Aug. 2007, resulting in a fatality rate of approximately 60% (www.who.int/csr/diseasei/avian influenza/country/cases table 2007 08 16/en/index.html). Concern over the pandemic potential of H5N1 viruses is thus clearly warranted. Although antiviral drugs, such as matrix protein 2 (M2) (adamantanes) and neuraminidase (NA) (oseltamivir and zanamivir) inhibitors, are currently available for prophylaxis and treatment of influenza virus infection, some of the H5N1 viruses isolated from humans are resistant to the adamantanes (Cheung et al., 2006; Hxushina et al., 2005; Puthavathana et al., 2005). In addition, some H5N1 viruses are resistant to oseltamivir (de Jung et al., 2005; Le et al., 2005).

For the existing seasonal human influenza, both inactivated virus vaccine and live attenuated virus vaccine are available. In April 2007, the U.S. Food and Drug Administration (FDA) announced the first approval of an inactivated vaccine for humans against the H5N1 virus. However, the available data indicate that inactivated H5 influenza vaccines are suboptimal in their immunogenicity, and a large amount of hemagglutinin (HA) glycoprotein or coadministration of an adjuvant is required to achieve an adequate immune response (Bressen et al., 2006; Lin et al., 2006; Nicholson et al.; 2005; Stephenson et al., 2003; Treanor et al.; 2006).

SUMMARY OF THE INVENTION

The wild-type influenza A virus M2 protein consists of three structural domains: a 24-amino-acid extracellular domain, a 19-amino-acid transmembrane domain, and a 54-amino-acid cytoplasmic tail domain (Lamb et al., 1985; Zebedee et al., 1985). The M2 transmembrane domain has ion channel activity, which functions at an early stage of the viral life cycle between the steps of virus penetration and uncoating (Helenius, 1992; Pinto et al., 1992). Recently, it was reported that the M2 cytoplasmic tail domain also has an important role in viral assembly and morphogenesis (lwatsuki-Horimoto et al., 2006; McCown et al., 2006; McCown et al., 2005).

The invention provides an isolated recombinant influenza virus comprising a mutant M2 protein having a deletion of one or more residues of the cytoplasmic tail of M2, which virus replicates in vitro. e.g., producing titers that are substantially the same or at most 10, 100 or 1,000 fold less than a corresponding wild-type influenza virus, but is attenuated in vivo. In one embodiment, the deletion includes 2 or more residues and up to 21 residues of the cytoplasmic tail of M2.

In one embodiment, the deletion of M2 includes 21 or more residues and up to 54 residues, i.e., the entire cytoplasmic tail, of the cytoplasmic tail of M2. In one embodiment of the invention, the mutant M2 protein may also comprise at least one amino acid substitution relative to a corresponding wild-type M2 protein. The substitution(s) in the M2 protein may be in the extracellular domain, the transmembrane (TM) domain, or the cytoplasmic domain, or any combination thereof. For example, substitutions in the TM domain may be at residues 25 to 43 of M2, e.g., positions 27, 30, 31, 34, 38, and/or 41 of the TM domain of M2. In another embodiment of the invention, the mutant M2 protein may also comprise a deletion in at least a portion of the extracellular domain and/or the TM domain, e.g., a deletion of residues 29 to 31, relative to a corresponding wild-type M2 protein. In yet another embodiment of the invention, the mutant M2 protein further comprises a heterologous protein, e.g., the cytoplasmic domain of a heterologous protein (a non-influenza viral protein), which may have a detectable phenotype, fused to the cytoplasmic tail or extracellular domain of M2, forming a chimeric protein. In one embodiment, a cytoplasmic domain of a heterologous protein is fused to the remaining residues of the cytoplasmic tail of the deleted M2 protein. In one embodiment, the presence of one or more substitutions, deletions, or insertions of heterologous sequences, or any combination thereof, does not substantially alter the properties of the recombinant influenza virus of the invention. e.g., the presence of one or more substitutions, deletions, or insertions of heterologous sequences does not result in virus titers in vitro that are more than about 1.5 to 2 logs lower, and/or does not result in virus that is substantially less attenuated in vivo, than the recombinant influenza virus of the invention comprising a mutant M2 protein having a deletion of one or more residues of the cytoplasmic tail of M2.

As described hereinbelow, the feasibility of using M2 tail mutants as live attenuated vaccines against H5N1 virus was tested. First, a series of highly pathogenic H5N1 (A/Vietnam/1203/04 [VN1203]) M2 cytoplasmic tail deletion mutants, e.g., having a deletion of 5 or more residues of the cytoplasmic tail of M2, was generated and their growth properties in vitro and in vivo examined. Unexpectedly, two of the mutant M2 viruses replicated as efficiently as the wild-type virus in vitro, although their growth was attenuated in mice. For instance, one mutant, which contains an 11-amino-acid deletion from the C terminus (M2del11 virus), grew as well as the wild-type virus but replicated in mice less efficiently. The attenuated growth of these mutant M2 viruses in vivo, but not in vitro, indicates that these mutant viruses may be useful in the development of live influenza vaccines.

As also described herein, a recombinant VN1203M2del11 virus was generated whose hemagglutinin (HA) gene was modified by replacing sequences at the cleavage site with those of an avirulent type of HA (M2del11-HAavir virus). M2del11-HAavir virus was highly attenuated as compared with M2del11 virus in mice. Moreover, M2del11-HAavir virus was able to induce strong serum and mucosal antibody response in the immunized mice, indicating that M2del11-HAavir virus is a potential candidate for a vaccine for H5N1 virus infection. Further, M2del11-HAavir virus protected mice against challenge with lethal doses of homologous (VN1203; clade 1) and antigenically distinct heterologous (A/Indonesia/7/2005; clade 2) H5N1 viruses. Surprisingly, a low dose of the virus, e.g., a dose of 100 to 1,000 PFU, resulted in strong immunity relative to a mutant M2 virus with a deletion in the TM domain (the dose of the recombinant influenza virus of the invention was 100 to 1,000 fold lower). That suggests that M2 cytoplasmic tail mutants have potential as live attenuated vaccines against H5N1 influenza virus, as well as other influenza virus strains. In one embodiment, the live attenuated influenza virus of the invention elicits both systemic and mucosal immunity at the primary portal of infection. Thus, the invention provides a live, attenuated vaccine or immunogenic composition comprising the recombinant virus of the invention, and a method of using the vaccine or immunogenic composition to immunize a vertebrate, e.g., an avian or a mammal, or induce an immune response in a vertebrate, respectively.

Also provided is a method of preparing a recombinant influenza virus comprising a mutant M2 protein having a deletion of one or more residues of the cytoplasmic tail of M2. The method comprises contacting a host cell with a plurality of influenza vectors, including a vector comprising the mutant M2 sequence, so as to yield recombinant virus. For example, the host cell is contacted with vectors for vRNA production including a vector comprising a promoter operably linked to an influenza virus PA DNA linked to a transcription termination sequence, a vector comprising a promoter operably linked to an influenza virus PB1 DNA linked to a transcription termination sequence, a vector comprising a promoter operably linked to an influenza virus PB2 DNA linked to a transcription termination sequence, a vector comprising a promoter operably linked to an influenza virus HA DNA linked to a transcription termination sequence, a vector comprising promoter operably linked to an influenza virus NP DNA linked to a transcription termination sequence, a vector comprising a promoter operably linked to an influenza virus NA DNA linked to a transcription termination sequence, a vector comprising a promoter operably linked to an influenza virus M DNA linked to a transcription termination sequence, and a vector comprising a promoter operably linked to an influenza virus NS DNA linked to a transcription termination sequence, wherein the M DNA comprises mutant M2 DNA for a M2 protein having at least one mutation that results in a deletion of one or more residues of the cytoplasmic tail of M2; and vectors for mRNA (protein) production including a vector comprising a promoter operably linked to a DNA segment encoding influenza virus PA, a vector comprising a promoter operably linked to a DNA segment encoding influenza virus PB1, a vector comprising a promoter operably linked to a DNA segment encoding influenza virus PB2, a vector comprising a promoter operably linked to a DNA segment encoding influenza virus NP, and optionally a vector comprising a promoter operably linked to a DNA segment encoding influenza virus HA, a vector comprising a promoter operably linked to a DNA segment encoding influenza virus NA, a vector comprising a promoter operably linked to a DNA segment encoding influenza virus M1, a vector comprising a promoter operably linked to a DNA segment encoding a M2 protein. e.g., a mutant M2 protein, and a vector comprising a promoter operably linked to a DNA segment encoding influenza virus NS. In one embodiment, separate vectors for M1 and M2 vRNA, and/or for NS1 and NS2 vRNA, in place of vectors for M vRNA and/or NS vRNA, are provided and employed. In one embodiment, the promoter in a vRNA vector includes but is not limited to a RNA polymerase I (PolI) promoter, e.g., a human RNA PolI promoter, a RNA polymerase II (PolII) promoter, a RNA polymerase Ill promoter, a SP6 promoter, a T7 promoter, or a T3 promoter. In one embodiment, one or more vRNA vectors include a PolII promoter and ribozyme sequences 5' to influenza virus sequences and the same or different ribozyme sequences 3' to the influenza virus sequences. In one embodiment, the mutant M2 gene is in a vector and is operably linked to a promoter including, but not limited to, a RNA PolI promoter, e.g., a human RNA PolI promoter, a RNA PolII promoter, a RNA polymerase Ill promoter, a SP6 promoter, a T7 promoter, or a T3 promoter. In one embodiment, the vRNA vectors include a transcription termination sequence including, but not limited to, a PolI transcription termination sequence, a PolII transcription termination sequence, or a PolIII transcription termination sequence, or one or more ribozymes. In one embodiment, the host cell is not contacted with the NA vector, and the resulting virus is further attenuated. In one embodiment, the M vector has further attenuating mutations in the M2 sequence, e.g., one or more substitutions or deletions in the TM domain. In one embodiment, one or more vectors for vRNA production are on the same plasmid (see, e.g., U.S. published application No. 20060166321, the disclosure of which is incorporated by reference herein). In one embodiment, one or more vectors for mRNA production are on the same plasmid (see. e.g., U.S. published application No. 2006/0166321).

In another embodiment, the method includes contacting a host cell with a vector having a PolI promoter linked to a PolI transcription termination sequence linked to an influenza virus PA DNA linked to a PolI promoter linked to a PolII transcription termination sequence (a bidirectional cassette), a vector having a PolII promoter linked to a PolI transcription termination sequence linked to an influenza virus PB1 DNA linked to a PolI promoter linked to a PolI transcription termination sequence, a vector having a PolII promoter linked to a PolI transcription termination sequence linked to an influenza virus PB2 DNA linked to a PolI promoter linked to a PolII transcription termination sequence, a vector having a PolII promoter linked to a PolI transcription termination sequence linked to an influenza virus HA DNA linked to a PolI promoter linked to a PolII transcription termination sequence, a vector having a PolII promoter linked to a PolI transcription termination sequence linked to an influenza virus NP DNA linked to a PolI promoter linked to a PolII transcription termination sequence, a vector having a PolI promoter linked to a PolI transcription termination sequence linked to an influenza virus NA DNA linked to a PolI promoter linked to a PolII transcription termination sequence, a vector having a PolIII promoter linked to a PolI transcription termination sequence linked to an influenza virus M DNA linked to a PolI promoter linked to PolI transcription termination sequence, and a vector having a PolII promoter linked to a PolI transcription termination sequence linked to an influenza virus NS DNA linked to a PolI promoter linked to PolI transcription termination sequence, wherein the M DNA comprises mutant M2 DNA for a M2 protein having at least one mutation that results in a deletion of one or more residues of the cytoplasmic tail of M2.

Also provided is a method of preparing a recombinant influenza virus comprising a mutant M2 gene for a M2 protein having a deletion of one or more residues of the cytoplasmic tail. The method comprises contacting a host cell with a plurality of influenza vectors, including a vector comprising a PolI promoter operably linked to an influenza virus PA DNA linked to a PolI transcription termination sequence, a vector comprising a PolI promoter operably linked to an influenza virus PB1 DNA linked to a PolI transcription termination sequence, a vector comprising a PolI promoter operably linked to an influenza virus PB2 DNA linked to a PolI transcription termination sequence, a vector comprising a PolI promoter operably linked to an influenza virus HA DNA linked to a PolI transcription termination sequence, a vector comprising PolI promoter operably linked to an influenza virus NP DNA linked to a PolI transcription termination sequence, a vector comprising a PolI promoter operably linked to an influenza virus DNA NA linked to a PolI transcription termination sequence, a vector comprising a PolI promoter operably linked to an influenza virus M DNA linked to a PolI transcription termination sequence, and a vector comprising a PolI promoter operably linked to an influenza virus NS DNA linked to a PolI transcription termination sequence, wherein the sequence of the DNA for M comprises a M2 sequence for a mutant M2 having at least one mutation that results in a deletion of one or more residues in the cytoplasmic domain; and a vector comprising a PolII promoter operably linked to a DNA segment encoding influenza virus PA, a vector comprising a PolII promoter operably linked to a DNA segment encoding influenza virus PB1, a vector comprising a PolII promoter operably linked to a DNA segment encoding influenza virus PB2, a vector comprising a PolII promoter operably linked to a DNA segment encoding influenza virus NP, and optionally a vector comprising a PolII promoter operably linked to a DNA segment encoding influenza virus HA, a vector comprising a PolII promoter operably linked to a DNA segment encoding influenza virus NA, a vector comprising a PolII promoter operably linked to a DNA segment encoding influenza virus M and a vector comprising a PolII promoter operably linked to a DNA segment encoding influenza virus NS. In one embodiment, separate vectors for M1 and M2 vRNA, and/or for NS1 and NS2 vRNA, in place of vectors for M vRNA and/or NS vRNA, are provided and employed. In one embodiment, the PolI promoter is a human PolI promoter. In one embodiment, the PolI promoter for each PolI containing vector is the same. In one embodiment, the PolI promoter for each PolII containing vector is the same. In one embodiment, the PolI promoter for two or more, but not all, of the PolII containing vectors, is the same. In one embodiment, the PolII promoter for each PolII containing vector is different.

In one embodiment, the deletion in the cytoplasmic domain of M2 includes 2, 3, 4, 5 or more, e.g., 11, 12, 13, 14, or 15 residues, but less than 22 residues, of the C-terminus of the cytoplasmic tail of M2. In one embodiment, the deletion is 2 up to 10 residues, including any integer in between. In one embodiment, the deletion is from 1 up to less than 8 residues, including any integer in between. In one embodiment, the deletion is from 5 up to 21 residues, including any integer in between. In one embodiment, the deletion is from 5 up to less than 28 residues, including any integer in between. In one embodiment, the deletion is from 9 up to 15 residues, including any integer in between. In one embodiment, the deletion is from 9 up to 23 residues, including any integer in between.

In one embodiment, the deletion in the cytoplasmic domain of M2 includes 22, 23, 24, 25 or more, e.g., 41, 42, 43, 44, or 45 residues, but less than 54 residues, of the C-terminus of the cytoplasmic tail of M2. In one embodiment, the deletion is from 22 up to 35 residues, including any integer in between. In one embodiment, the deletion is from 29 up to 35 residues, including any integer in between. In one embodiment, the deletion is from 35 up to 45 residues, including any integer in between. In one embodiment, the deletion is from 9 to less than 28 residues, including any integer in between.

The invention further provides a composition having one or more of the vectors described above, and a host cell contacted with such a composition, e.g., so as to yield infectious virus. The host cell may be contacted with each vector, or a subset of vectors, sequentially. One or more of the vectors may be on plasmids. The compositions and host cells of the invention may also include another vector for vRNA production or protein production that includes heterologous sequences, e.g., for a marker gene, or a therapeutic or prophylactic gene, e.g., an immunogen for a cancer associated antigen or for a pathogen such as a bacteria, a noninfluenza virus, fungus, or other pathogen.

In one embodiment of the invention, the mutant M2 gene also encodes at least one amino acid substitution relative to the corresponding wild-type M2 protein. In one embodiment, fewer than 10%, e.g., 5% or fewer, of the residues are substituted. In one embodiment, at least one substitution is in the TM domain. In another embodiment, the mutant M2 has one or more substitutions in the extracellular domain. In yet another embodiment, the mutant M2 gene comprises a deletion of one or more residues in the TM domain. In one embodiment, the mutant M2 comprises a deletion of one or more residues, or an insertion of one or more residues, in the extracellular domain.

In one embodiment, the recombinant virus of the invention includes one or more genes from influenza A virus. In another embodiment, the recombinant virus of the invention may include one or more genes from influenza B virus, e.g., an influenza B HA gene. In yet another embodiment, the recombinant virus of the invention may include one or more genes from influenza C virus.

In one embodiment, the influenza DNA in a vector is a DNA with a native (naturally occurring) influenza virus sequence. In one embodiment, the influenza DNA is a DNA that has been manipulated in vitro, e.g., by inserting, deleting or substituting, or a combination thereof, one or more nucleotides in, for example, the coding region.

The HA sequences in a recombinant virus of the invention may be any one of the sixteen influenza A HA sequences, a chimeric HA sequence or any non-native HA sequence. The NA sequences in a recombinant virus of the invention may be any one of the nine influenza A NA sequences, a chimeric NA sequence or any non-native NA sequence.

In one embodiment, other attenuating mutations may be introduced to the vectors, e.g., a mutation in a HA cleavage site that results in a site that is not cleaved.

BRIEF DESCRIPTION OF THE FIGURES

FIG. 6A-6B. Primers employed to amplify influenza sequences (SEQ ID NOs: 19-34).

FIG. 12. Protection against challenge with lethal doses of H5 viruses of mice immunized with M2del11-HAavir virus. One month after immunization of mice with M2del11-HA, the immunized mice virus survived a lethal challenge with 100 MLD$_{50}$ of highly pathogenic H5N1 viruses (VN1203 or Indonesia 7 virus) and did not show any symptom (i.e., weight loss) after challenge, whereas all of the control mice died or had to be euthanized due to their disease by day 8 post-challenge.

DETAILED DESCRIPTION OF THE INVENTION

Definitions

Figure 1:
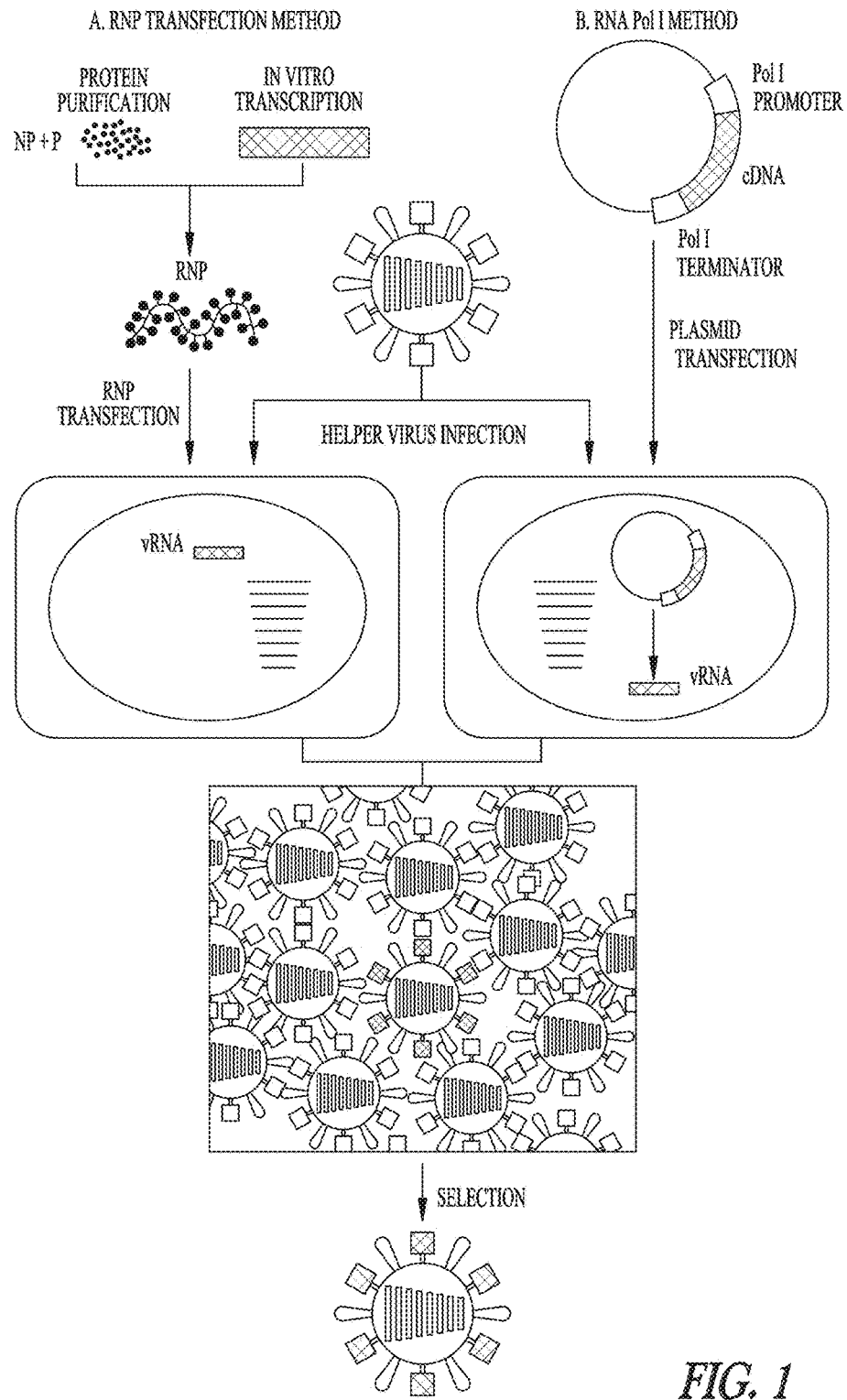
FIG. 1. Schematic diagram of established reverse genetics systems. In the RNP transfection method (A), purified NP and polymerase proteins are assembled into RNPs with use of in vitro-synthesized vRNA. Cells are transfected with RNPs, followed by helper virus infection. In the RNA polymerase I method (B), a plasmid containing the RNA polymerase I promoter, a cDNA encoding the vRNA to be rescued, and the RNA polymerase I terminator is transfected into cells. Intracellular transcription by RNA polymerase I yields synthetic vRNA, which is packaged into progeny virus particles upon infection with helper virus. With both methods, transfectant viruses (i.e., those containing RNA derived from cloned cDNA), are selected from the helper virus population.

As used herein, the terms "isolated and/or purified" refer to in vitro preparation, isolation and/or purification of a nucleic acid molecule such as a vector, plasmid of the invention or a virus of the invention, so that it is not associated with in vivo substances, or is substantially purified from in vitro substances. An isolated virus preparation is generally obtained by in vitro culture and propagation and is substantially free from other infectious agents. As used herein, "substantially free" means below the level of detection for a particular infectious agent using standard detection methods for that agent. A "recombinant" virus is one which has been manipulated in vitro, e.g., using recombinant DNA techniques, to introduce changes to the viral genome, or otherwise artificially generated.

As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Influenza Virus

The life cycle of viruses generally involves attachment to cell surface receptors, entry into the cell and uncoating of the viral nucleic acid, followed by replication of the viral genes inside the cell. After the synthesis of new copies of viral proteins and genes, these components assemble into progeny virus particles, which then exit the cell (reviewed by Roizman and Palese, 1996). Different viral proteins play a role in each of these steps.

The influenza A virus is an enveloped negative-strand virus with eight RNA segments encapsidated with nucleoprotein (NP) (reviewed by Lamb and Krug, 1996). The eight single-stranded negative-sense viral RNAs (vRNAs) encode a total of ten to eleven proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cDNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, the M segment of influenza B virus encodes two proteins, M1 and BM2, through a termination-reinitiation scheme of tandem cistrons, and the NA segment encodes the NA and NB proteins from a bicistronic mRNA. Influenza C virus, which has 7 vRNA segments, relies on spliced transcripts to produce M protein; the product of the unspliced mRNA is proteolytically cleaved to yield the CM2 protein. In addition, influenza C virus encodes a HA-esterase (HEF) rather than individual HA and NA proteins.

Spanning the viral membrane for influenza A virus are three proteins: hemagglutinin (HA), neuraminidase (NA), and M2. The extracellular domains (ectodomains) of HA and NA are quite variable, while the ectodomain domain of M2 is essentially invariant among influenza A viruses. The M2 protein which possesses ion channel activity (Pinto et al., 1992), is thought to function at an early state in the viral life cycle between host cell penetration and uncoating of viral RNA (Martin and Helenius, 1991; reviewed by Helenius, 1992; Sugrue et al., 1990). Once virions have undergone endocytosis, the virion-associated M2 ion channel, a homotetrameric helix bundle, is believed to permit protons to flow from the endosome into the virion interior to disrupt acid-labile M1 protein-ribonucleoprotein complex (RNP) interactions, thereby promoting RNP release into the cytoplasm (reviewed by Helenius, 1992). In addition, among some influenza strains whose HAs are cleaved intracellularly (e.g., A/fowl plagues/Rostock/34), the M2 ion channel is thought to raise the pH of the trans-Golgi network, preventing conformational changes in the HA due to conditions of low pH in this compartment (Hay et al., 1985; Ohuchi et al., 1994; Takeuchi and Lamb, 1994).

Evidence that the M2 protein of influenza virus has ion channel activity was obtained by expressing the protein in oocytes of *Xenopus laevis* and measuring membrane currents (Pinto et al., 1992; Wang et al., 1993; Holsinger et al., 1994). Specific changes in the M2 protein transmembrane (TM) domain altered the kinetics and ion selectivity of the channel, providing strong evidence that the M2 TM domain constitutes the pore of the ion channel (Holsinger et al., 1994). In fact, the M2 TM domain itself can function as an ion channel (Duff and Ashley, 1992). M2 protein ion channel activity is thought to be essential in the life cycle of influenza viruses, because amantadine hydrochloride, which blocks M2 ion channel activity (Hay et al., 1993), inhibits viral replication (Kato and Eggers. 1969; Skehel et al., 1978).

Exemplary Viruses and Methods

The invention provides recombinant influenza viruses useful in vivo. In one embodiment, the invention provides an isolated recombinant influenza virus comprising a mutant M2 protein which has a deletion of at least one residue, e.g., 2 or more residues, of the C-terminus of the cytoplasmic tail, wherein the replication of the virus in vitro is not substantially altered but the recombinant virus is attenuated in vivo relative to a corresponding virus without the deletion.

In one embodiment, the deletion is at least 3 but no more than 20 residues of the C-terminus of the cytoplasmic tail. In one embodiment, the deletion is at least 5 but no more than 20 residues of the C-terminus of the cytoplasmic tail. In another embodiment, the deletion is at least 2 but less than 8 residues of the C-terminus of the cytoplasmic tail. In yet another embodiment, the deletion is at least 10 but no more than 25 residues of the C-terminus of the cytoplasmic tail. In another embodiment, the deletion is at least 10 but no more than 20 residues of the C-terminus of the cytoplasmic tail. In a further embodiment, the deletion is at least 9 but less than 25 residues of the C-terminus of the cytoplasmic tail.

The isolated virus may further include another attenuating mutation in addition to the deleted M2 protein.

In one embodiment, the mutant M2 protein further comprises a heterologous protein at the C-terminus. In one embodiment, the mutant M2 protein further comprises at least one amino acid substitution, e.g., in the transmembrane domain of the M2 protein. In one embodiment, the mutant M2 protein further comprises a deletion in the transmembrane domain, e.g., a deletion that includes residues 29 to 31. In one embodiment, the recombinant virus comprises influenza A HA, for instance, H5 HA. In one embodiment, the HA is not H3 HA.

Also provided is a method of preparing a recombinant influenza virus comprising a mutant M2 protein. The method includes contacting a host cell with a plurality of influenza vectors so as to yield recombinant influenza virus. The plurality of vectors includes: vectors for vRNA production including a vector comprising a promoter operably linked to an influenza virus PA DNA linked to a transcription termination sequence, a vector comprising a promoter operably linked to an influenza virus PB1 DNA linked to a transcription termination sequence, a vector comprising a promoter operably linked to an influenza virus PB2 DNA linked to a transcription termination sequence, a vector comprising a promoter operably linked to an influenza virus HA DNA linked to a transcription termination sequence, a vector comprising promoter operably linked to an influenza virus NP DNA linked to a transcription termination sequence, a vector comprising a promoter operably linked to an influenza virus NA DNA linked to a transcription termination sequence, a vector comprising a promoter operably linked to an influenza virus M DNA linked to a transcription termination sequence, and a vector comprising a promoter operably linked to an influenza virus NS DNA linked to a transcription termination sequence, wherein the M DNA comprises mutant M2 DNA having at least one mutation that results in a deletion of one or more residues of the cytoplasmic domain; and b) vectors for protein production including a vector comprising a promoter operably linked to a DNA segment encoding influenza virus PA, a vector comprising a promoter operably linked to a DNA segment encoding influenza virus PB1, a vector comprising a promoter operably linked to a DNA segment encoding influenza virus PB2, a vector comprising a promoter operably linked to a DNA segment encoding influenza virus NP, and optionally a vector comprising a promoter operably linked to a DNA segment encoding influenza virus HA, a vector comprising a promoter operably linked to a DNA segment encoding influenza virus NA, a vector comprising a promoter operably linked to a DNA segment encoding influenza virus M1, a vector comprising a promoter operably linked to a DNA segment encoding an ion channel protein, and a vector comprising a promoter operably linked to a DNA segment encoding influenza virus NS. Virus which replicates in vitro but is attenuated in vivo is isolated from the host cells. In one embodiment, the vector for vRNA production of HA comprises H5 DNA, e.g., one with a mutant cleavage site associated with reduced virulence. In one embodiment, the promoter in the vectors for vRNA production is a PolI promoter. In one embodiment, the vector for vRNA production of HA comprises influenza A HA DNA.

Further provided are compositions with one or more vectors of the invention. In one embodiment, a composition includes a plurality of influenza vectors, for instance, vectors for vRNA production including a vector comprising a promoter operably linked to an influenza virus PA DNA linked to a transcription termination sequence, a vector comprising a promoter operably linked to an influenza virus PB1 DNA linked to a transcription termination sequence, a vector comprising a promoter operably linked to an influenza virus PB2 DNA linked to a transcription termination sequence, a vector comprising a promoter operably linked to an influenza virus HA DNA linked to a transcription termination sequence, a vector comprising promoter operably linked to an influenza virus NP DNA linked to a transcription termination sequence, a vector comprising a promoter operably linked to an influenza virus NA DNA linked to a transcription termination sequence, a vector comprising a promoter operably linked to an influenza virus M DNA linked to a transcription termination sequence, and a vector comprising a promoter operably linked to an influenza virus NS DNA linked to a transcription termination sequence, wherein the M DNA comprises mutant M2 DNA having at least one mutation the results in a deletion of one or more residues of the cytoplasmic tail of M2: and vectors for mRNA production including a vector comprising a promoter operably linked to a DNA segment encoding influenza virus PA, a vector comprising a promoter operably linked to a DNA segment encoding influenza virus PB1, a vector comprising a promoter operably linked to a DNA segment encoding influenza virus PB2, a vector comprising a promoter operably linked to a DNA segment encoding influenza virus NP, and optionally a vector comprising a promoter operably linked to a DNA segment encoding influenza virus HA, a vector comprising a promoter operably linked to a DNA segment encoding influenza virus NA, a vector comprising a promoter operably linked to a DNA segment encoding influenza virus M1, a vector comprising a promoter operably linked to a DNA segment encoding an ion channel protein, and a vector comprising a promoter operably linked to a DNA segment encoding influenza virus NS. In one embodiment, the composition further includes a vector comprising a promoter operably linked to a heterologous DNA sequence of interest, e.g., wherein the vector comprises a DNA sequence for an immunogenic polypeptide or peptide of a pathogen or wherein the vector comprises a DNA sequence for a therapeutic protein. In one embodiment, two or more of the vectors for vRNA production are on the same plasmid. In one embodiment, two or more of the vectors for mRNA production are on the same plasmid.

Vaccines

A vaccine of the invention may comprise immunogenic proteins including glycoproteins of any pathogen, e.g., an immunogenic protein from one or more bacteria, viruses, yeast or fungi. Thus, in one embodiment, the influenza viruses of the invention may be vaccine vectors for influenza virus or other viral pathogens including but not limited to lentiviruses such as HIV, hepatitis B virus, hepatitis C virus, herpes viruses such as CMV or HSV or foot and mouth disease virus.

A complete virion vaccine is concentrated by ultrafiltration and then purified by zonal centrifugation or by chromatography. It is inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmever, 1975), an anionic detergent such as ammonium deoxycholate (Laver & Webster, 1976; Webster et al., 1977); or a nonionic detergent such as that commercialized under the name TRITON X100. The hemagglutinin may also be isolated after treatment of the virions with a protease such as bromelin, then purified by a method such as that described by Grand and Skehel (1972).

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done.

Inactivated Vaccines. Inactivated influenza virus vaccines of the invention are provided by inactivating replicated virus of the invention using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines. In general, the responses to SV and surface antigen (i.e., purified HA or NA) vaccines are similar. An experimental inactivated WV vaccine containing an NA antigen immunologically related to the epidemic virus and an unrelated HA appears to be less effective than conventional vaccines (Ogra et al., 1977). Inactivated vaccines containing both relevant surface antigens are preferred.

Live Attenuated Virus Vaccines. Live, attenuated influenza virus vaccines, can also be used for preventing or treating influenza virus infection, according to known method steps. Attenuation is preferably achieved in a single step by transfer of attenuated genes from an attenuated donor virus to a replicated isolate or reassorted virus according to known methods (see, e.g., Murphy, 1993). Since resistance to influenza A virus is mediated by the development of an immune response to the HA and NA glycoproteins, the genes coding for these surface antigens must come from the circulating wild-type strains. The attenuated genes are derived from the attenuated parent. In this approach, genes that confer attenuation preferably do not code for the HA and NA glycoproteins. Otherwise, these genes could not be transferred to reassortants bearing the surface antigens of the clinical virus isolate.

Many donor viruses have been evaluated for their ability to reproducibly attenuate influenza viruses. As a non-limiting example, the A/Ann Arbor(AA)/6/60 (H2N2) cold adapted (ca) donor virus can be used for attenuated vaccine production (see, e.g., Edwards, 1994; Murphy, 1993). Reassortant progeny are then selected at 25° C. (restrictive for replication of virulent virus), in the presence of an H2N2 antiserum, which inhibits replication of the viruses bearing the surface antigens of the attenuated A/AA/6/60 (H2N2) ca donor virus.

A large series of H1N1 and H3N2 reassortants have been evaluated in humans and found to be satisfactorily: (a) infectious, (b) attenuated for seronegative children and immunologically primed adults, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible adults and children.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced, for example, into the PB2 polymerase gene (Subbarao et al., 1993) or the NS gene. Thus, new donor viruses can also be generated bearing attenuating mutations introduced by site-directed mutagenesis, and such new donor viruses can be used in the production of live attenuated reassortant H1N1 and H3N2 vaccine candidates in a manner analogous to that described above for the A/AA/6/60 ca donor virus.

It is preferred that such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking infectivity to the degree that the vaccine causes minimal change of inducing a serious pathogenic condition in the vaccinated mammal.

The virus can thus be attenuated or inactivated, formulated and administered, according to known methods, as a vaccine to induce an immune response in an animal. e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and DNA screening (such as probe hybridization or PCR) to confirm that donor genes encoding the antigenic determinants (e.g., HA or NA genes) are not present in the attenuated viruses. See, e.g., Robertson et al., 1988; Kilboume, 1969; Aymard-Henry et al., 1985; Robertson et al., 1992.

Pharmaceutical Compositions

Pharmaceutical compositions of the present invention, suitable for inoculation or for parenteral or oral administration, comprise attenuated or inactivated influenza viruses, optionally further comprising sterile aqueous or non-aqueous solutions, suspensions, and emulsions. The compositions can further comprise auxiliary agents or excipients, as known in the art. See, e.g., Berkow et al., 1987; *Avery's Drug Treatment*. 1987; Osol, 1980. The composition of the invention is generally presented in the form of individual doses (unit doses).

Conventional vaccines generally contain about 0.1 to 200 µg, preferably 10 to 15 µg, of hemagglutinin from each of the strains entering into their composition. The vaccine forming the main constituent of the vaccine composition of the invention may comprise a virus of type A, B or C, or any combination thereof, for example, at least two of the three types, at least two of different subtypes, at least two of the same type, at least two of the same subtype, or a different isolate(s) or reassortant(s). Human influenza virus type A includes H1N1, H2N2 and H3N2 subtypes.

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents. See, e.g., Berkow et al., 1992; Avery's, 1987; and Osol, 1980.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized. Examples of materials suitable for use in vaccine compositions are provided in Osol (1980).

Heterogeneity in a vaccine may be provided by mixing replicated influenza viruses for at least two influenza virus strains, such as 2-50 strains or any range or value therein. Influenza A or B virus strains having a modern antigenic composition are preferred. According to the present invention, vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-α, interferon-β, interferon-γ, tumor necrosis factor-alpha, thiosemicarbarzones, methisazone, rifampin, ribavirin, a pyrimidine analog, a purine analog, foscamet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines, are provided before any symptom of a pathogen infection becomes manifest. The prophylactic administration of the composition serves to prevent or attenuate any subsequent infection. When provided prophylactically, the gene therapy compositions of the invention, are provided before any symptom of a disease becomes manifest. The prophylactic administration of the composition serves to prevent or attenuate one or more symptoms associated with the disease.

When provided therapeutically, an attenuated or inactivated viral vaccine is provided upon the detection of a symptom of actual infection. The therapeutic administration of the compound(s) serves to attenuate any actual infection. See. e.g., Berkow et al., 1992; and Avery, 1987. When provided therapeutically, a gene therapy composition is provided upon the detection of a symptom or indication of the disease. The therapeutic administration of the compound (s) serves to attenuate a symptom or indication of that disease.

Thus, an attenuated or inactivated vaccine composition of the present invention may thus be provided either before the onset of infection (so as to prevent or attenuate an anticipated infection) or after the initiation of an actual infection. Similarly, for gene therapy, the composition may be provided before any symptom of a disorder or disease is manifested or after one or more symptoms are detected.

A composition is said to be "pharmacologically acceptable" if its administration can be tolerated by a recipient patient. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of patients. Protection may be limited to mitigating the severity or rapidity of onset of symptoms of the influenza virus infection.

Pharmaceutical Administration

A composition of the present invention may confer resistance to one or more pathogens, e.g., one or more influenza virus strains, by either passive immunization or active immunization. In active immunization, an inactivated or attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a symptom or condition of the disease, or in the total or partial immunity of the individual to the disease. As used herein, a gene therapy composition is said to prevent or attenuate a disease if its administration results either in the total or partial attenuation (i.e., suppression) of a symptom or condition of the disease, or in the total or partial immunity of the individual to the disease.

At least one inactivated or attenuated influenza virus, or composition thereof, of the present invention may be administered by any means that achieve the intended purposes, using a pharmaceutical composition as previously described.

For example, administration of such a composition may be by various parenteral routes such as subcutaneous, intravenous, intradermal, intramuscular, intraperitoneal, intranasal, oral or transdermal routes. Parenteral administration can be by bolus injection or by gradual perfusion over time. A preferred mode of using a pharmaceutical composition of the present invention is by intramuscular or subcutaneous application. See, e.g., Berkow et al., 1992; and Avery, 1987.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired biological effect. It is understood that the effective dosage will be dependent upon the age, sex, health, and weight of the recipient, kind of concurrent treatment, if any, frequency of treatment, and the nature of the effect wanted. The ranges of effective doses provided below are not intended to limit the invention and represent preferred dose ranges. However, the most preferred dosage will be tailored to the individual subject, as is understood and determinable by one of skill in the art. See, e.g., Berkow et al., 1992; Avery's, 1987; and Ebadi, 1985.

The dosage of an attenuated virus vaccine for a mammalian (e.g., human) or avian adult organism can be from about $10^3$-$10^7$ plaque forming units (PFU)/kg, or any range or value therein. The dose of inactivated vaccine can range from about 0.1 to 200, e.g., 50 µg of hemagglutinin protein. However, the dosage should be a safe and effective amount as determined by conventional methods, using existing vaccines as a starting point.

The dosage of immunoreactive HA in each dose of replicated virus vaccine can be standardized to contain a suitable amount, e.g., 1-50 µg or any range or value therein, or the amount recommended by the U.S. Public Heath Service (PHS), which is usually 15 µg, per component for older children □3 years of age, and 7.5 µg per component for older children <3 years of age. The quantity of NA can also be standardized, however, this glycoprotein can be labile during the processor purification and storage. Each 0.5-ml dose of vaccine preferably contains approximately 1-50 billion virus particles, and preferably 10 billion particles.

The invention will be further described by the following non-limiting examples.

EXAMPLE 1

Materials and Methods

Cells and viruses. 293T human embryonic kidney cells and Madin-Darby canine kidney cells (MDCK) were maintained in Dulbecco=s modified Eagle medium (DMEM) supplemented with 10% fetal calf serum and in modified Eagle=s medium (MEM) containing 5% newborn calf serum, respectively. All cells were maintained at 37° C. in 5% $CO_2$. Influenza viruses A/WSN/33 (H1N1) and A/PR/8/34 (H1N1) were propagated in 10-day-old eggs.

Figure 2:
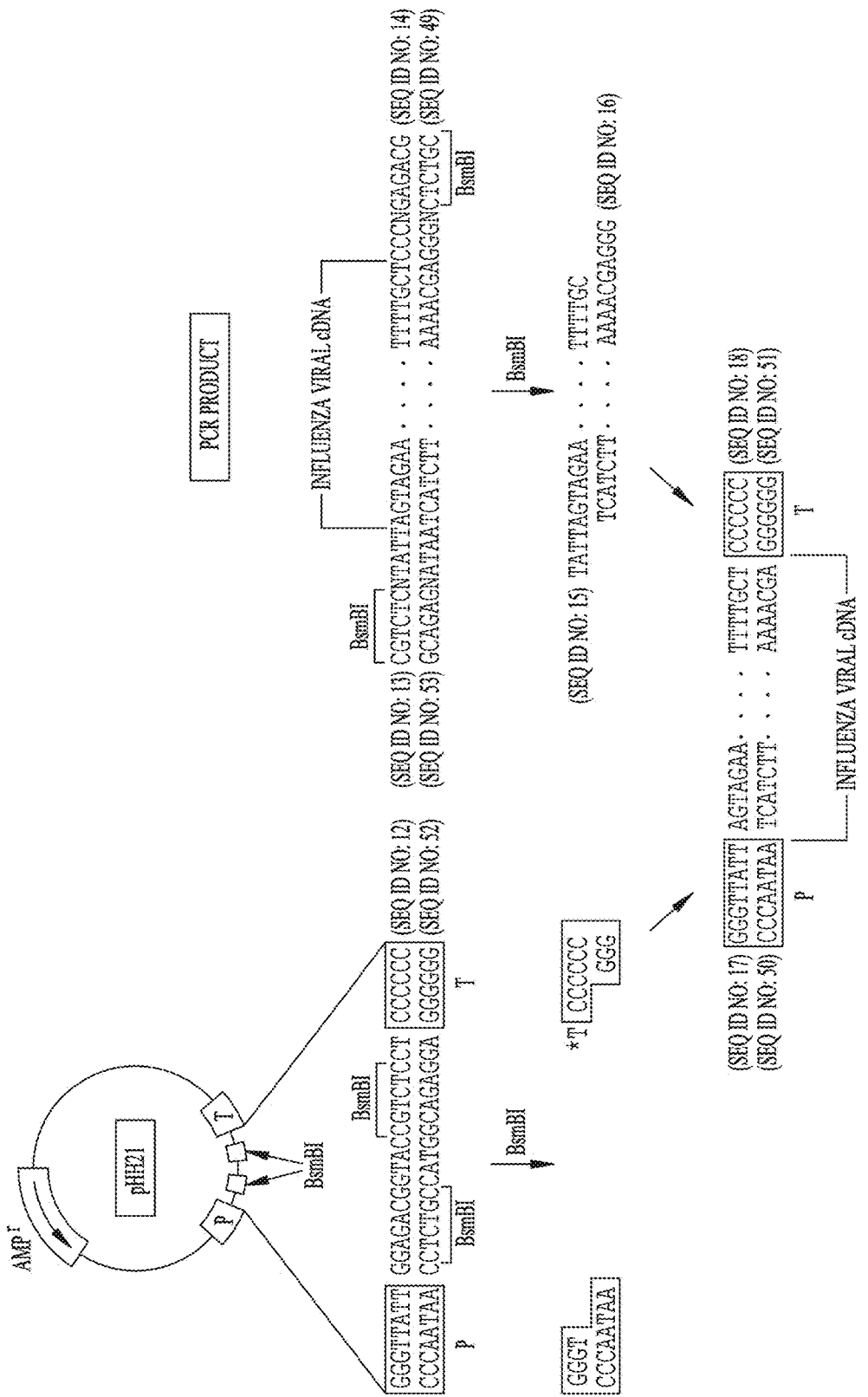
FIG. 2. Schematic diagram of the generation of RNA polymerase I constructs (SEQ ID NOs: 12-18 and 49-53). cDNAs derived from influenza virus were amplified by PCR, digested with BsmBI and cloned into the BsmBI sites of the pHH21 vector (E. Hoffmann, Ph.D. thesis, Justus, Liebig-University, Giessen, Germany). which contains the human RNA polymerase I promoter (P) and the mouse RNA polymerase I terminator (T). The thymidine nucleotide upstream of the terminator sequence (*T) represents the 3N end of the influenza viral RNA. Influenza A virus sequences are shown in bold face letters.

Construction of plasmids. To generate RNA polymerase I constructs, cloned cDNAs derived from A/WSN/33 or APR/8/34 viral RNA were introduced between the promoter and terminator sequences of RNA polymerase I. Briefly, the cloned cDNAs were amplified by PCR with primers containing BsmBI sites, digested with BsmBI, and cloned into the BsmBI sites of the pHH21 vector which contains the human RNA polymerase I promoter and the mouse RNA polymerase I terminator, separated by BsmBI sites (FIG. 2). The PB2, PB1, PA, HA, NP, NA, M, and NS genes of the A/WSN/33 strain were PCR-amplified by use of the following plasmids: pSCWPB2, pGW-PB1, and pSCWPA (all obtained from Dr. Debi Nayak at the University of California Los Angeles), and pWH17, pWNP152, pT3WNA15 (Castrucci et al., 1992), pGT3WM, and pWNS1, respectively. The PB1 gene of influenza A/PR/8/34 virus was amplified by using pcDNA774 (PB1) (Perez et al., 1998) as a template. See FIG. 6 for the sequences of the primers. To ensure that the genes were free of unwanted mutations, PCR-derived fragments were sequences with an autosequencer (Applied Biosystem Inc., CA, USA) according to the protocol recommended by the manufacturer. The cDNAs encoding the HA, NP, NA, and M1 genes of A/WSN/33 virus were cloned as described (Huddleston et al., 1982) and subcloned into the eukaryotic expression vector pCAGGS/MCS (controlled by the chicken β-actin promoter) (Niwa et al., 1991), resulting in pEWSN-HA, pCAGGS-WSN-NP0-14, pCAGGS-WNA15, and pCAGGS-WSN-M1-2/1, respectively. The M2 and NS2 genes from the A/PR/8/34 virus were amplified by PCR and cloned into pCAGGS/MCS, yielding pEP24c and pCA-NS2. Finally, pcDNA774 (PB1), pcDNA762(PB2), and pcDNA787(PA) were used to express the PB2, PB1, and PA proteins under control of the cytomegalovirus promoter (Perez et al., 1998).

Generation of infectious influenza particles. 293T cells (1 H 10$^6$) were transfected with a maximum of 17 plasmids in different amounts with use of Trans IT LT-1 (Panvera. Madison, Wis.) according to the manufacturers instructions. Briefly, DNA and transfection reagent were mixed (2 µl Trans IT-LT-1 per µg of DNA), incubated at room temperature for 45 minutes and added to the cells. Six hours later, the DNA-transfection reagent mixture was replaced by Opti-MEM (Gibco/BRL, Gaithersburg, Md.) containing 0.3% bovine serum albumin and 0.01% fetal calf serum. At different times after transfection, viruses were harvested from the supernatant and titrated on MDCK cells. Since helper virus was not required by this procedure, the recovered transfectant viruses were analyzed without plaque purification.

Determination of the percentage of plasmid-transfected cells producing viruses. Twenty-four hours after transfection, 293T cells were dispersed with 0.02% EDTA into single cells. The cell suspension was then diluted 10-fold and transferred to confluent monolayers of MDCK cells in 24-well plates. Viruses were detected by the hemagglutination assay.

Immunostaining assay. Nine hours after infection with influenza virus, cells were washed twice with phosphate-buffered saline (PBS) and fixed with 3.7% paraformaldehyde (in PBS) for 20 minutes at room temperature. Next, they were treated with 0.1% Triton X-100 and processed as described by Neumann et al. (1997).

Results

Figure 3:
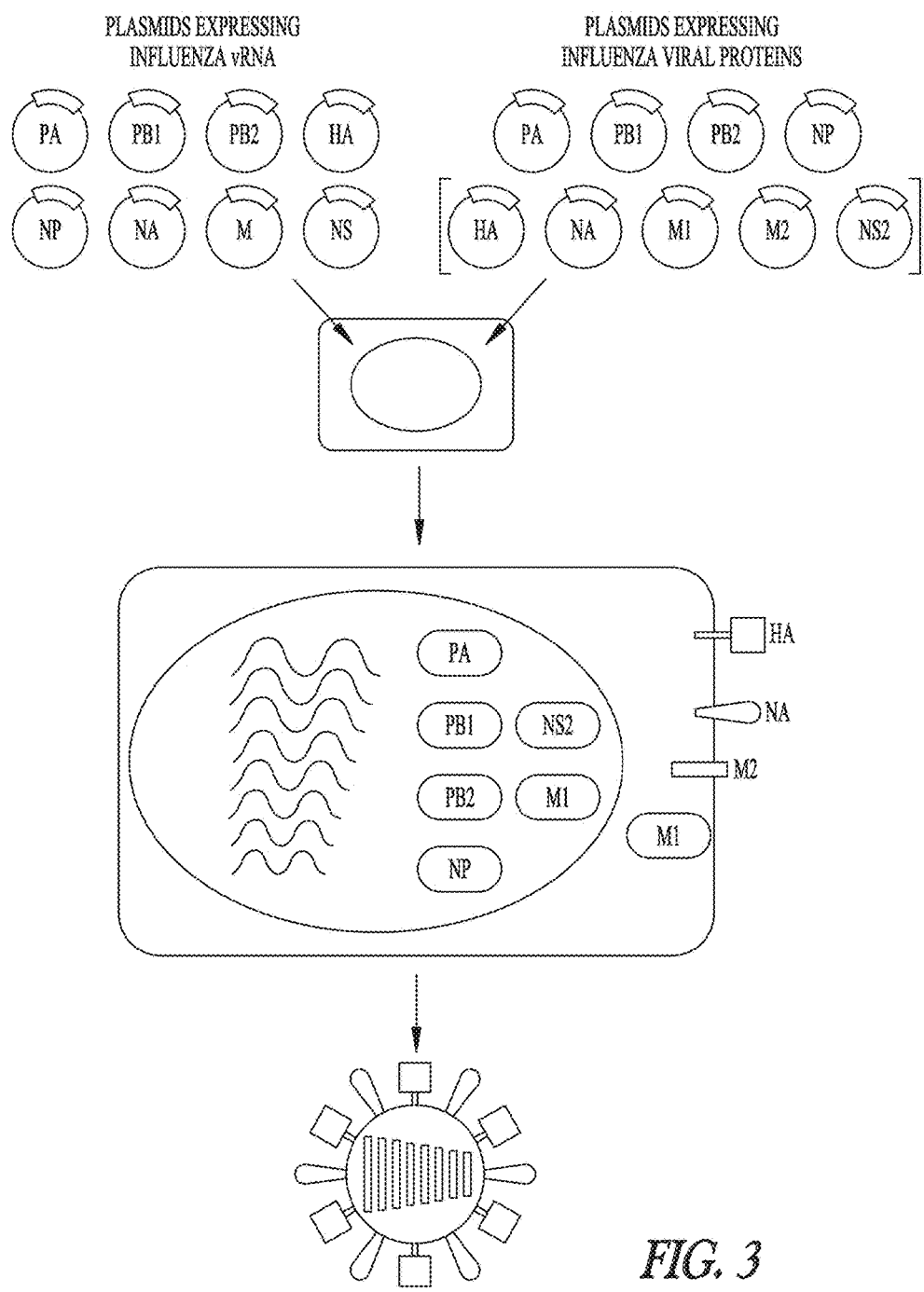
FIG. 3. Reverse genetics method for generating segmented negative-sense RNA viruses. Plasmids containing the RNA polymerase I promoter a cDNA for each of the eight viral RNA segments, and the RNA polymerase I terminator are transfected into cells together with protein expression plasmids. Although infectious viruses can be generated with plasmids expressing PA, PB1, PB2, and NP, expression of all remaining structural proteins (shown in brackets) increases the efficiency of virus production depending on the virus generated.
Figure 4A:
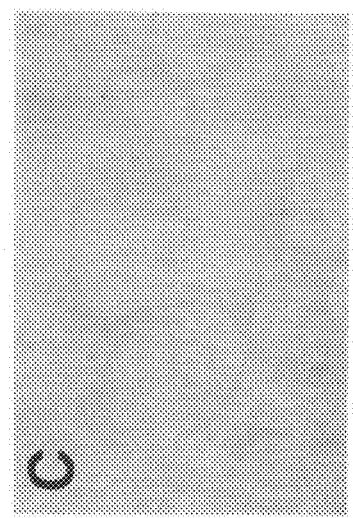
FIG. 4A-4F. Detection of the FLAG epitope in cells infected with a transfectant virus. Antibody staining was used to identify the NA in MDCK cells infected with either PR8-WSN-FL79 (A, D) or AWSN/33 wild-type virus (B, E), or on mock-infected MDCK cells (C, F). Nine hours after infection, cells were fixed with paraformaldehyde, treated with Triton X-100 and incubated with either anti-FLAG (A-C) or anti-WSN NA (D-F) monoclonal antibodies. Intensive Golgi staining (red) is apparent in positive samples (A, D, and E).
Figure 4B:
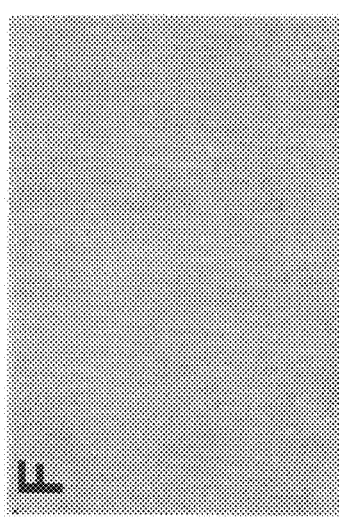
Figure 4C:
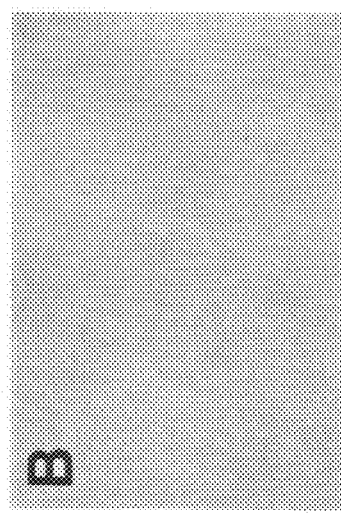
Figure 4D:
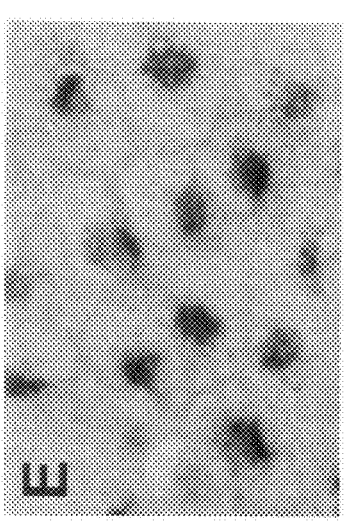
Figure 4E:
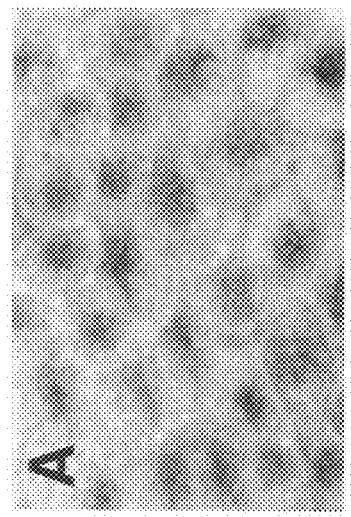
Figure 4F:
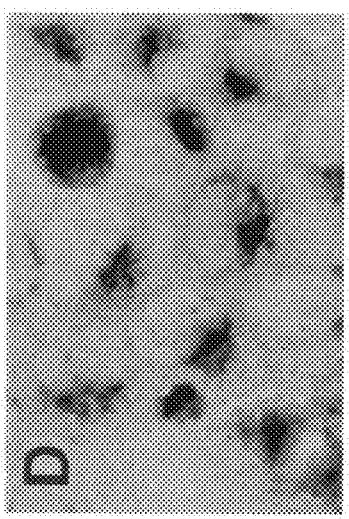

Generation of infectious virus by plasmid-driven expression of viral RNA segments, three polymerase subunits and NP protein. Although transfection of cells with a mixture of RNPs extracted from purified virions results in infectious influenza particles, this strategy is not likely to be efficient when used with eight different in vitro generated RNPs. To produce infectious influenza viruses entirely from cDNAs, eight viral RNPs were generated in vivo. Thus, plasmids were prepared that contain cDNAs for the full-length viral RNAs of the A/WSN/33 virus, flanked by the human RNA polymerase I promoter and the mouse RNA polymerase I terminator. In principle, transfection of these eight plasmids into eukaryotic cells should result in the synthesis of all eight influenza vRNAs. The PB2, PB1, PA and NP proteins, generated by cotransfection of protein expression plasmids, should then assemble the vRNAs into functional vRNPs that are replicated and transcribed, ultimately forming infectious influenza viruses (FIG. 3). 1 H $10^6$ 293T cells were transfected with protein expression plasmids (1 μg of pcDNA762 (PB2), 1 μg of pcDNA774(PB1), 0.1 μg of pcDNA787(PA), and 1 μg of pCAGGS-WSN-NP0/14) and 1 μg of each of the following RNA polymerase I plasmids (pPolI-WSN-PB2, pPolI-WSN-PB1, pPolI-WSN-PA, pPolI-WSN-HA, pPolI-WSN-NP, pPolI-WSN-NA, pPolI-WSN-M, and pPolI-WSN-NS). The decision to use a reduced amount of pcDNA787(PA) was based on previous observations (Mena et al., 1996), and data on the optimal conditions for generation of virus-like particles (VLPs) (data not shown). Twenty-four hours after transfection of 293T cells, 7 H $10^3$ pfu of virus per ml was found in the supernatant (Experiment 1, Table 1), demonstrating for the first time the capacity of reverse genetics to produce influenza A virus entirely from plasmids.

TABLE 1

Plasmid sets used to produce influenza virus from cloned cDNA*

| | Experiment | | | | | | | |
|---|---|---|---|---|---|---|---|---|
| | 1 | 2 | 3 | 4 | 5 | 6 | 7 | 8 |
| RNA polymerase I plasmids for:[H] | | | | | | | | |
| PB1 | + | + | ! | ! | ! | ! | ! | ! |
| PR8-PB1 | ! | ! | + | + | + | + | + | + |
| PB2 | + | + | + | + | + | + | + | + |
| PA | + | + | + | + | + | + | + | + |
| HA | + | + | + | + | + | + | + | + |
| NP | + | + | + | + | + | + | + | + |
| NA | + | + | + | + | + | + | + | + |
| M | + | + | + | + | + | + | + | + |
| NS | + | + | + | + | + | + | + | + |
| Protein expression plasmids for: | | | | | | | | |
| PB1 | + | + | + | + | ! | + | + | + |
| PB2 | + | + | + | + | + | ! | + | + |
| PA | + | + | + | + | + | + | ! | + |
| NP | + | + | + | + | + | + | + | ! |
| HA | ! | + | ! | + | + | + | + | + |
| NA | ! | + | ! | + | + | + | + | + |
| M1 | ! | + | ! | + | + | + | + | + |
| M2 | ! | + | ! | + | + | + | + | + |
| NS2 | ! | + | ! | + | + | + | + | + |
| Virus titer (pfu/ml) | 7 H $10^3$ | 7 H $10^3$ | 1 H $10^3$ | 3 H $10^4$ | 0 | 0 | 0 | 0 |

*293T cells were transfected with the indicated plasmids. Twenty-four (Experiments 1 and 2) or forty-eight hours (Experiments 3-8) later, the virus titer in the supernatant was determined in MDCK cells.
[H]Unless otherwise indicated, plasmids were constructed with cDNAs representing the RNAs of A/WSN/33 virus.

Efficiency of influenza virus production with coexpression of all viral structural proteins. Although expression of the viral NP and polymerase proteins is sufficient for the plasmid-driven generation of influenza viruses, it was possible that the efficiency could be improved. In previous studies, the expression of all influenza virus structural proteins (PB2, PB1, PA, HA, NP, NA, M1, M2, and NS2) resulted in VLPs that contained an artificial vRNA encoding a reporter chloramphenicol-acetyltransferase gene (Mena et al., 1996). Thus, the availability of the entire complement of structural proteins, instead of only those required for viral RNA replication and transcription, might improve the efficiency of virus production. To this end, 293T cells were transfected with optimal amounts of viral protein expression plasmids (as judged by VLP production; unpublished data): 1 μg of pcDNA762(PB2) and pcDNA774(PB1); 0.1 μg of pcDNA787(PA); 1 μg of pEWSN-HA, pCAGGS-WSN-NP0/14, and pCAGGS-WNA15; 2 μg of pCAGGS-WSN-M1-2/1; 0.3 μg of pCA-NS2; and 0.03 μg of pEP24c (for M2), together with 1 μg of each RNA polymerase I plasmid (Experiment 2, Table 1). A second set of cells was transfected with the same set of RNA polymerase I plasmids, with the exception of the PB1 gene, for which pPolI-PR8/34-PB1 was substituted in an effort to generate a reassortant virus, together with plasmids expressing only PA, PB1, PB2, and NP (Experiment 3, Table 1) or those expressing all the influenza structural proteins (Experiment 4, Table 1). Yields of WSN virus did not appreciably differ at 24 hours (Experiments 1 and 2, Table 1) or at 36 hours (data not shown) post-transfection. However, more than a 10-fold increase in yields of the virus with PR/8/34-PB1 was found when all the influenza viral structural proteins were provided (Experiments 3 and 4, Table 1). Negative controls, which lacked one of the plasmids for the expression of PA, PB1, PB2, of NP proteins, did not yield any virus (Experiments 5-8, Table 1). Thus, depending on the virus generated, expression of all influenza A virus structural proteins appreciably improved the efficiency of the reverse genetics method.

Next, the kinetics of virus production after transfection of cells was determined using the set of plasmids used to generate a virus with the A/PR/8/34-PB1 gene. In two of three experiments, virus was first detected at 24 hours after transfection. The titer measured at that time, >$10^3$ pfu/ml, had increased to >$10^6$ pfu/ml by 48 hours after transfection (Table 2). To estimate the percentage of plasmid-transfected cells that were producing viruses, 293T cells were treated with EDTA (0.02%) at 24 hours after transfection to disperse the cells, and then performed limiting dilution studies. In this experiment, no free virus was found in the culture supernatant at this time point. The results indicated that 1 in $10^{3.3}$ cells was generating infectious virus particles.

TABLE 2

Kinetics of virus production after plasmid transfection into 293T cells*

| Hours after plasmid transfection | Virus titers in culture supernatant (pfu/ml) Experiment | | |
|---|---|---|---|
| | 1 | 2 | 3 |
| 6 | 0 | ND | ND |
| 12 | 0 | ND | 0 |
| 18 | 0 | ND | 0 |
| 24 | 0 | 2 H $10^3$ | 6 H $10^3$ |
| 30 | ND | 5 H $10^4$ | 9 H $10^4$ |
| 36 | 6 H $10^2$ | >1 H $10^5$ | 7 H $10^5$ |
| 42 | ND | >1 H $10^6$ | 5 H $10^6$ |
| 48 | 8 H $10^4$ | >1 H $10^6$ | 1 H $10^7$ |

*293T cells were transfected with eight RNA polymerase I plasmids encoding A/WSN/33 virus genes with the exception of PB1 gene, which is derived from A/PR/8/34 virus, and nine protein expression plasmids as described in the text. At different time points, we titrated virus in the culture supernatant in MDCK cells.
ND = not done.

Recovery of influenza virus containing the FLAG epitope in the NA protein. To verify that the new reverse genetics system allowed the introduction of mutations into the genome of influenza A viruses, a virus containing a FLAG epitope (Castrucci et al., 1992) in the NA protein was generated. 293T cells were transfected with an RNA polymerase I plasmid (pPolI-WSN-NA/FL79) that contained a cDNA encoding both the NA protein and a FLAG epitope at the bottom of the protein=s head, together with the required RNA polymerase I and protein expression plasmids. To confirm that the recovered virus (PR8-WSN-FL79) did in fact express the NA-FLAG protein, immunostaining assays of cells infected with PR8-WSN-FL79 or A/WSN/33 wild-type virus was performed. A monoclonal antibody to the FLAG epitope detected cells infected with PR8-WSN-FL79, but not those infected with wild-type virus (FIG. 4). Recovery of the PR8-WSN-FL79 virus was as efficient as that for the untagged wild-type virus (data not shown). These results indicate that the new reverse genetics system allows one to introduce mutations into the influenza A virus genome.

Figure 5:
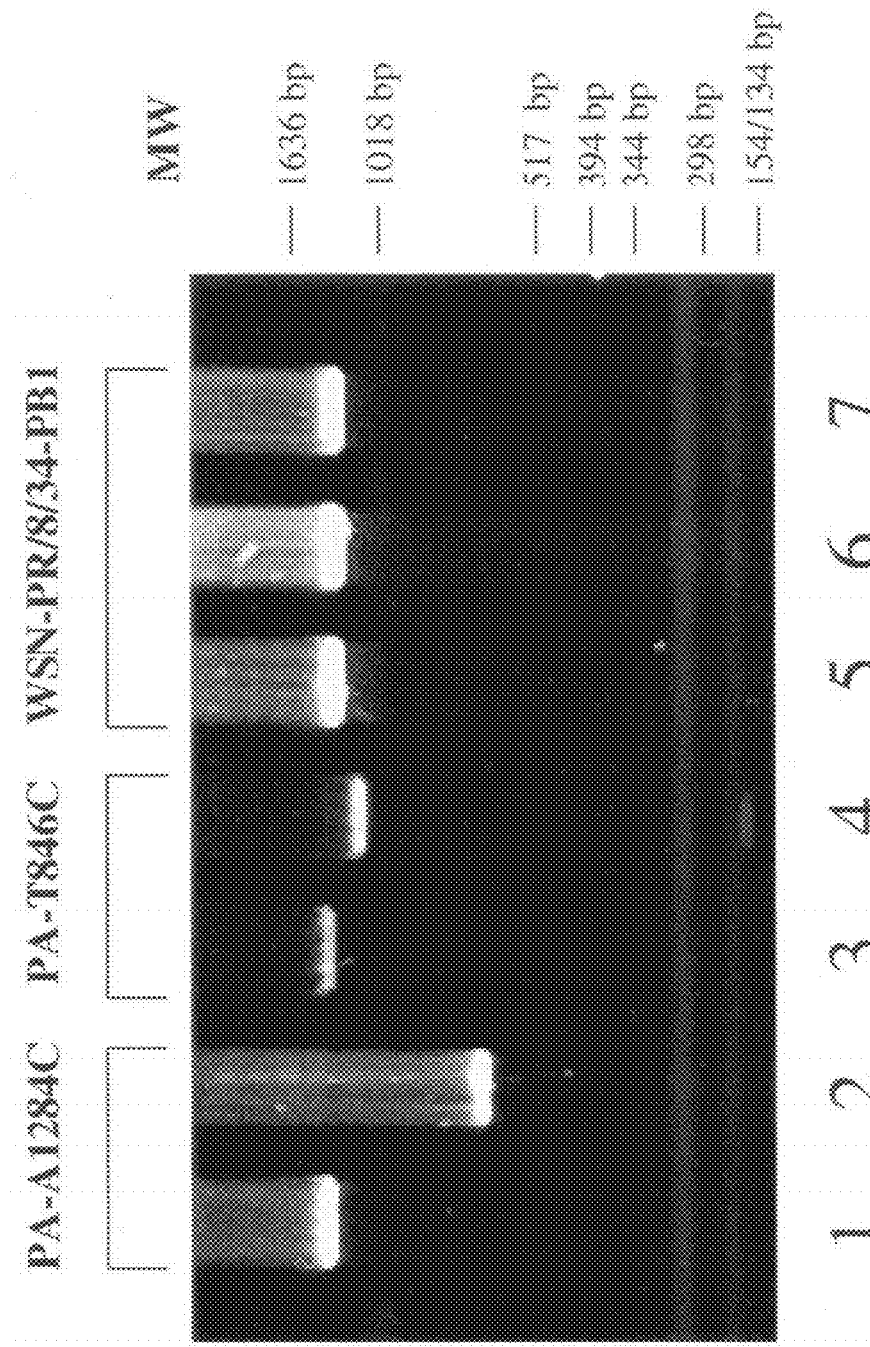
FIG. 5. Recovery of PA mutants. The PA gene of each virus was amplified by RT-PCR with primers that yield a 1226 bp fragment (position 677 to 1903 of the mRNA, lanes 1, 3, 5), which was then digested with the restriction enzyme Bsp120I (at position 846 of the mRNA, lanes 4, 7) or PvuII (at position 1284 of the mRNA, lanes 2, 6). The presence of Bsp120I or PvuII sites in the PCR products yielded either 169 bp and 1057 bp or 607 bp and 619 bp fragments, respectively. MW=molecular weight markers.

Generation of infectious influenza virus containing mutations in the PA gene. To produce viruses possessing mutations in the PA gene, two silent mutations were introduced creating new recognition sequences for restriction endonucleases (Bsp120I at position 846 and PvuII at position 1284 of the mRNA). Previously, it was not possible to modify this gene by reverse genetics, because of the lack of a reliable selection system. Transfectant viruses, PA-T846C and PA-A1284 were recovered. The recovered transfectant viruses were biologically cloned by two consecutive limiting dilutions. To verify that the recovered viruses were indeed transfectants with mutations in the PA gene, cDNA for the PA gene was obtained by reverse transcriptase-PCR. As shown in FIG. 5, PA-T846C and PA-A1284C viruses had the expected mutations within the PA gene, as demonstrated by the presence of the newly introduced restriction sites. PCR of the same viral samples and primers without the reverse transcription step failed to produce any products (data not shown), indicating that the PA cDNA was indeed originated from vRNA instead of the plasmid used to generate the viruses. These results illustrate how viruses with mutated genes can be produced and recovered without the use of helper viruses.

Discussion

The reverse genetics systems described herein allows one to efficiently produce influenza A viruses entirely from cloned cDNAs. Bridgen and Elliott (1996) also used reverse genetics to generate a Bunyamwera virus (Bunvaviridae family), but it contains only three segments of negative-sense RNA, and the efficiency of its production was low, $10^2$ pfu/$10^7$ cells. Although the virus yields differed among the experiments, consistently >$10^3$ pfu/$10^6$ cells was observed for influenza virus, which contains eight segments. There are several explanations for the high efficiency of the reverse genetics system described hereinabove. Instead of producing RNPs in vitro (Luytjes et al., 1989), RNPs were generated in vivo through intracellular synthesis of vRNAs using RNA polymerase I and through plasmid-driven expression of the viral polymerase proteins and NP. Also, the use of 293T cells, which are readily transfected with plasmids (Goto et al., 1997), ensured that a large population of cells received all of the plasmids needed for virus production. In addition, the large number of transcripts produced by RNA polymerase I, which is among the most abundantly expressed enzymes in growing cells, likely contributed to the overall efficiency of the system. These features led to a correspondingly abundant number of vRNA transcripts and adequate amounts of viral protein for encapsidation of vRNA, formation of RNPs in the nucleus, and export of these complexes to the cell membrane, where new viruses are assembled and released.

Previously established reverse genetics systems (Enami et al., 1990; Neumann et al., 1994; Luytjes et al., 1989; Pleschka et al., 1996) require helper-virus infection and therefore selection methods that permit a small number of transfectants to be retrieved from a vast number of helper viruses. Such strategies have been employed to generate influenza viruses that possess one of the following cDNA-derived genes: PB2 (Subbarao et al., 1993), HA (Enami et al., 1991; Horimoto et al., 1994). NP (Li et al., 1995), NA (Enami et al., 1990), M (Castrucci et al., 1995; Yasuda et al., 1994), and NS (Enami et al., 1991). Most of the selection methods, except for those applicable to the HA and NA genes, rely on growth temperature, host range restriction, or drug sensitivity, thus limiting the utility of reverse genetics for functional analysis of the gene products. Even with the HA and NA genes, for which reliable antibody-driven selection systems are available, it is difficult to produce viruses with prominent growth defects. In contrast, the reverse genetics system described herein does not require helper virus and permits one to generate transfectants with mutations in any gene segment or with severe growth defects. This advantage is demonstrated in FIG. 5, which the recovery of transfectant viruses with a mutated PA gene. Having the technology to introduce any viable mutation into the influenza A virus genome will enable investigators to address a number of long-standing issues, such as the nature of regulatory sequences in nontranslated regions of the viral genome, structure-function relationships of viral proteins, and the molecular basis of host-range restriction and viral pathogenicity.

Although inactivated influenza vaccines are available, their efficacy is suboptimal due partly to their limited ability to elicit local IgA and cytotoxic T cell responses. Clinical trials of cold-adapted live influenza vaccines now underway suggest that such vaccines are optimally attenuated, so that they will not cause influenza symptoms, but will still induce protective immunity (reviewed in Keitel & Piedra, 1998). However, preliminary results indicate that these live virus vaccines will not be significantly more effective than the best inactivated vaccine (reviewed in Keitel. & Piedra, 1998), leaving room for further improvement. One possibility would be to modify a cold-adapted vaccine with the reverse genetics system described above. Alternatively, one could start from scratch by using reverse genetics to produce a Amaster@ influenza A strain with multiple attenuating mutations in the genes that encode internal proteins. The most intriguing application of the reverse genetics system described herein may lie in the rapid production of attenuated live-virus vaccines in cases of suspected pandemics involving new HA or NA subtypes of influenza virus.

This new reverse genetics system will likely enhance the use of influenza viruses as vaccine vectors. The viruses can be engineered to express foreign proteins or immunogenic epitopes in addition to the influenza viral proteins. One could, for example, generate viruses with foreign proteins as a ninth segment (Enami et al., 1991) and use them as live vaccines. Not only do influenza viruses stimulate strong cell-mediated and humoral immune responses, but they also afford a wide array of virion surface HA and NA proteins (e.g., 15 HA and 9 NA subtypes and their epidemic variants), allowing repeated immunization of the same target population.

Influenza VLPs possessing an artificial vRNA encoding a reporter gene have been produced by expressing viral structural proteins and vRNA with the vaccinia-T7 polymerase system (Mena et al., 1996). Using reverse genetics, one can now generate VLPs containing vRNAs that encode proteins required for vRNA transcription and replication (i.e., PA, PB1, PB2, and NP), as well as vRNAs encoding proteins of interest. Such VLPs could be useful gene delivery vehicles. Importantly, their lack of genes encoding viral structural proteins would ensure that infectious viruses will not be produced after VLP-gene therapy. Since the influenza virus genome is not integrated into host chromosome, the VLP system would be suitable for gene therapy in situations requiring only short-term transduction of cells (e.g., for cancer treatment). In contrast to adenovirus vectors (Kovesdi et al., 1997), influenza VLPs could contain both HA and NA variants, allowing repeated treatment of target populations.

The family Orthomyxoviridae comprises influenza A, B, and C viruses, as well as the recently classified Thogotovirus. The strategy for generating infectious influenza A viruses entirely from cloned cDNAs described herein would apply to any orthomyxovirus, and perhaps to other segmented negative-sense RNA viruses as well (e.g., Bunyaviridae, Arenaviridae). The ability to manipulate the viral genome without technical limitations has profound implications for the study of viral life cycles and their regulation, the function of viral proteins and the molecular mechanisms of viral pathogenicity.

EXAMPLE 2

Materials and Methods

Cells and viruses. 293T human embryonic kidney cells and Madin-Darby canine kidney cells (MDCK) were maintained in DMEM supplemented with 10% FCS and in MEM containing 5% newborn calf serum, respectively. The 293T cell line is a derivative of the 293 line, into which the gene for the simian virus 40 T antigen was inserted (DuBridge et al., 1987). All cells were maintained at 37° C. in 5% $CO_2$. Influenza virus A/Udorn/307/72 (H3N2) (Udorn) was propagated in 10-day-old eggs.

Construction of plasmids. The cDNA of Udorn virus was synthesized by reverse transcription of viral RNA with an oligonucleotide complementary to the conserved 3' end of viral RNA, as described by Katz et al. (1990). The cDNA was amplified by PCR with M gene-specific oligonucleotide primers containing BsmBI sites, and PCR products were cloned into the pT7Blueblunt vector (Novagen, Madison, Wis.). The resulting construct was designated pTPolIUdM. After digestion with BsmBI, the fragment was cloned into the BsmBI sites of the pHH21 vector, which contains the human RNA polymerase I promoter and the mouse RNA polymerase I terminator, separated by BsmBI sites (Neumann et al., 1999), resulting in pPolIUdM. Plasmids derived from pHH21 for the expression of vRNA are referred to as APoII@ constructs in this report.

The M mutants were constructed as follows. pTPolIIUdM was first amplified by inverse PCR (Ochman et al., 1988) using the back-to-back primers M2104R (5'-AAGAGG GTCACITGAATCG-3'; SEQ ID NO: 1) and M2V27T (5'-ACTGTTGCTGCGAGTATC-3'; SEQ ID NO:2) and M2A30P (5'-GTTGITGCTCCAACTATC-3'; SEQ ID NO:3) and M2S31N (5'-GTIGTTGCTGCGAACATC-3'; SEQ ID NO:4) and M2del29-31 (5'-GTGTATCATTGGGATCTTGC-3'; SEQ ID NO:5), and the back-to-back primers M2128R (5'-CCCAATGATACTCGCAGC-3'; SEQ ID NO:6) and M2W41A (5'-ATCTIGCACTTGATATIGGCAATTC-3'; SEQ ID NO:7), and the back-to-back primers M2HATMR(5'-CACCAGTGAACTGGCGACAGTTGAGTAGATCGCCAGAATGTCACTTG AATCGTTGCATCTGC-3'; SEQ ID NO:8) and M2HATM (5'-CTTTTGGTCTCCCTGGGGGCAATCAGTTTCTGGATGGATCGT CTTTT TCAAATGC-3'; SEQ ID NO:9), and M2NATMR (5'-GCTIAGTATCAATGTATTCCA1TTATGATTGATATCC AAATGCTGTC ACTTGAATCGTTGCATCTGC-3'SEQ ID NO: 10) and M2NATM (5'-ATTATAGGAGTCGTAATGTGTATCTCAGGGATTACCATAATAGATCGT CTTTTTTTCAAATGC-3'; SEQ ID NO: 11).

The PCR products were phosphorylated, self-ligated, and propagated in E. coli strain DH5α, and then digested with BsmBI and cloned into the BsmBI sites of the pHH21 vector. The resulting constructs were designated pPolIM2V27T, pPolIM2A30P, pPolIM2S31N, pPolIM2del29-31, pPolIM2W41A, pPolIM2HATM, and pPolIM2NATM. All of the constructs were sequenced to ensure that unwanted mutations were not present. The plasmids for the expression of the HA (pEWSN-HA), NP (pCAGGS-WSN-NP0/14), NA (pCAGGS-WNA15), M1 (pCAGGS-WSN-M1-2/1) proteins of AWSN/33 (H1N1) virus, and the M2 (pEP24c), NS2 (pCANS2), PB1 (pcDNA774), PB2 (pcDNA762), and PA (pcDNA787) of A/Puerto Rico/8/34 (H1N1) virus are described in Neumann et al. (1999).

Plasmid-driven Reverse Genetics. Transfectant viruses were generated as reported in Neumann et al. (1999). Briefly, 17 plasmids (8 PolI constructs for 8 RNA segments and 9 protein-expression constructs for 9 structural proteins) were mixed with transfection reagent (2 μl of Trans IT LT-1 (Panvera, Madison, Wis.) per μg of DNA), incubated at room temperature for 15 minutes, and added to $1 \times 10^6$ 293T cells. Six hours later, the DNA-transfection reagent mixture was replaced by Opti-MEM (GIBCO/BRL) containing 0.3% BSA and 0.01% FCS. Forty-eight hours later, viruses in the supernatant were plaque-purified in MDCK cells once and then inoculated into MDCK cells for the production of stock virus. The M genes of transfectant viruses were sequenced to confirm the origin of the gene and the presence of the intended mutations and to ensure that no unwanted mutations were present. In all experiments, the transfection viruses contained only the M gene from Udorn virus and the remaining genes from A/WSN/33.

Replicative properties of the transfectant viruses. MDCK cells in duplicate wells of 24-wells plates were infected with wild-type and mutant viruses at a multiplicity of infection (MOI) of 0.001 plaque-forming units (PFU) per cell, overlaid with MEM medium containing 0.5 μg of trypsin per ml, and incubated at 37° C. At different times, supernatants were assayed for infectious virus in plaque assays on MDCK cells.

To investigate the amantadine sensitivity of mutant viruses, the viruses were titrated in MDCK cells in the presence of different concentrations of the drug.

M2 incorporation into viruses. Transfectant viruses were grown in MDCK cells containing 0.5 μg of trypsin per ml. Viruses were purified through six-step sucrose gradients (20, 30, 35, 40, 45, and 50%) for 2.5 hours at 50,000 g at 4° C. Virus was resuspended in PBS and stored in aliquots at −80° C. Purified virus was resuspended in the lysis buffer (0.6 M KCl, 50 mM Tris-CI [pH 7.5]. 0.5% Triton X-100). The viral lysates were placed on 15% SDS-polyacrylamide gels, which then were electrotransferred to polyvinylidene difluoride (PVDF) membrane. The membrane was blocked overnight at 4° C. with 5% skimmed milk in PBS, and then incubated with the 14C2 anti-M2 monoclonal antibody (kindly provided by Dr. R. Lamb) and anti-WSN-NP monoclonal antibody for 1 hour at room temperature. The membrane was washed three times with PBS containing 0.05% Tween-20. Bound antibodies were detected with a VECTASTAIN ABC kit (Vector) and the Western immunoblot ECL system (Amersham). Signal intensities were quantified with an Alpha Imager 2000 (Alpha Innotech Corporation).

Experimental Infection. Five-week-old female BALB/c mice, anesthetized with isoflurane, were infected intranasally with 50 μl (5.0×10³ PFU) of virus. Virus titers in organs were determined 3 days after infection with MDCK cells, as described (Bilsel et al., 1993).

Results

Figure 7:
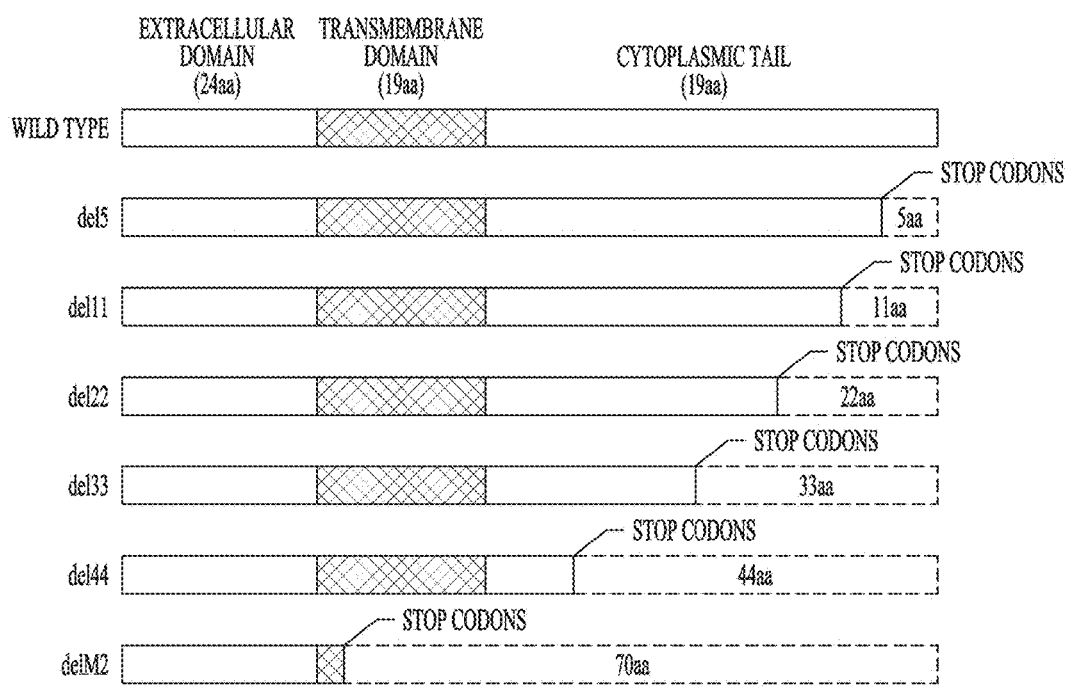
FIG. 7. Schematic representation of the M2 mutants. The M gene was derived from a highly pathogenic H5N1 (VN1203) virus. The mutants del5, del11, del22, del33, and del44 contain a 5-, 11-, 22-, 33-, or 44-amino-acid (aa) deletion from the C terminus, respectively. The mutant delM2 was constructed by deletion of 70 C-terminal residues, including the entire transmembrane and cytoplasmic domains.

Generation of influenza A viruses containing mutations in the M2 Protein. The TM domain of the M2 protein is modeled to have an α helical structure (Duff et al., 1992; Sugrue and Hay, 1991; Sansom and Kerr, 1993). Mutations at residues V-27, A-30, S-31, G-34, and L-38, all of which are located on the same face of the αhelix, alter the properties of the M2 ion channel (Grambas et al., 1992; Pinto et al., 1992; Wang et al., 1993). To determine whether the ion channel activity of M2 is essential for viral replication, five plasmids were constructed and used to generate mutant viruses possessing changes in the M2 TM domain (FIG. 7). The whole-cell currents of the mutant proteins expressed in oocytes of *Xenopus laevis*, were measured by Holsinger et al. (1994), using a two-electrode voltage-clamp procedure. None of three mutants, i.e., M2A30P. M2W41A, and M2del29-31, had functional ion channel activity at either neutral or low pH. M2V27T and M2S31N, which showed ion channel activity at low pH (Holsinger et al., 1994), were used as positive controls.

To generate mutant viruses by plasmid-driven reverse genetics (Neumann et al., 1999), 293T cells were transfected with nine protein-expression plasmids and eight others for the production of viral RNA segments that encoded all A/WSN/33 (H1N1) viral genes except the M gene, which was derived from the A/UJdor/307/72 (H3N2) (Udorn) virus (wild-type). The corresponding transfectant viruses were designated M2V27T, M2A30P, M2S31N, M2W41A, M2del29-31, and WSN-UdM, for the virus containing the parental Udorn M gene.

To determine the efficiency of virus generation, viruses were titrated in the culture supernatant of 293T cells at 48 hours post-transfection using MDCK cells. As shown in Table 3, more than 10⁵ transfectant viruses with the wild-type or mutant M gene were present. Thus, all viruses bearing M2 mutations and the virus possessing the wild-type Udorn M gene were generated with similar efficiency. The transfectant viruses were plaque-purified once in MDCK cells and then inoculated into MDCK cells to make virus stocks. The stability of the introduced mutations was analyzed by sequencing the M gene segments of the transfectant viruses after ten passages in MDCK cells. No revertants were found.

TABLE 3

Virus titers in the supernatant of 293T cells after plasmid transfection[a]

| Virus | Titers (PFU/ml) |
|---|---|
| Wild type | $1.9 \times 10^5$ |
| M2V27T | $6.0 \times 10^5$ |
| M2A30P | $1.1 \times 10^5$ |
| M2S31N | $1.2 \times 10^6$ |
| M2W41A | $1.2 \times 10^6$ |
| M2del29-31 | $1.7 \times 10^6$ |

TABLE 3-continued

Virus titers in the supernatant of 293T cells after plasmid transfection[a]

| Virus | Titers (PFU/ml) |
|---|---|
| M2HATM | $2.2 \times 10^4$ |
| M2NATM | $2.2 \times 10^3$ |

[a]293T cells were transfected with eight plasmids for the production of A/WSN/33 vRNA (excluding the M gene, which was derived form A/Udorn/72 virus) and nine protein expression plasmids, as described in Materials and Methods. At 48 hours posttransfection, virus in the supernatant of 293T cell cultures was titrated using MDCK cells.

Figure 8:
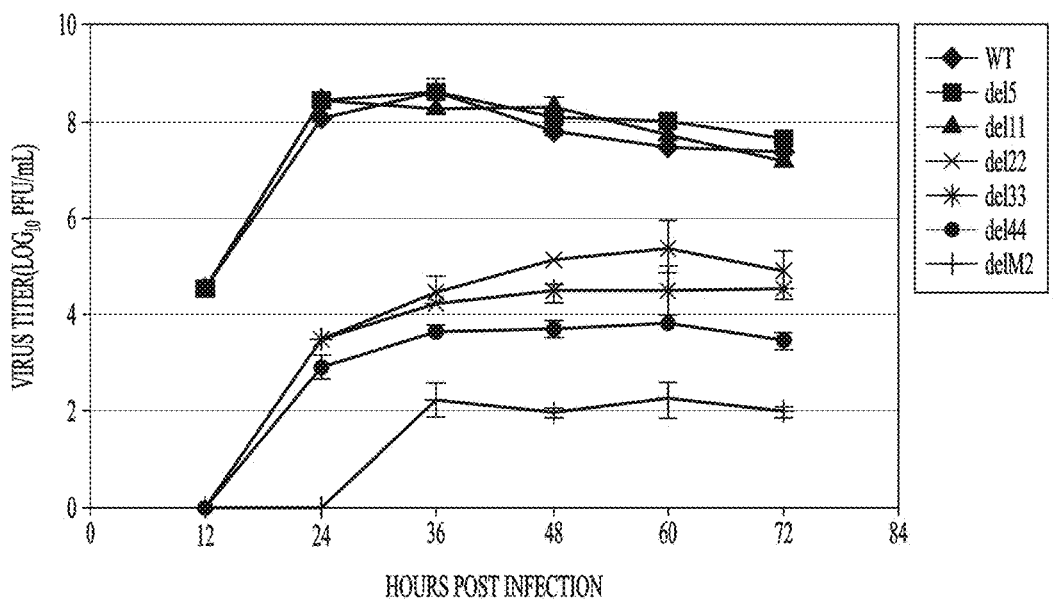
FIG. 8. Growth kinetics of the M2 tail deletion mutant viruses in MDCK cells. MDCK cells were infected with the M2 tail deletion mutant viruses at an MOI of 0.001. At the indicated times after infection, the virus titer in the supernatant was determined with M2CK cells. The values presented are means from duplicate experiments. WT, wild-type. The del5 and del11 mutants grew as well as the wild-type virus, whereas the del22, del33, del44, and delM2 replicated less efficiently than did the wild-type virus in MDCK cells (about 1,000 to about 10,000-fold lower).

Growth properties of M2 mutant viruses in tissue culture. Next, the growth properties of M2 ion channel mutants and wild-type WSN-UdM virus in MDCK cells were compared (FIG. 8). Cells were infected at an MOI of 0.001, and yields of virus in the culture supernatant were determined at different times postinfection. The mutant viruses did not differ appreciably from the wild-type WSN-UdM virus in either growth rate or the size of plaques formed at 48 hours (1.5 mm in diameter in 3 days).

Figure 9:
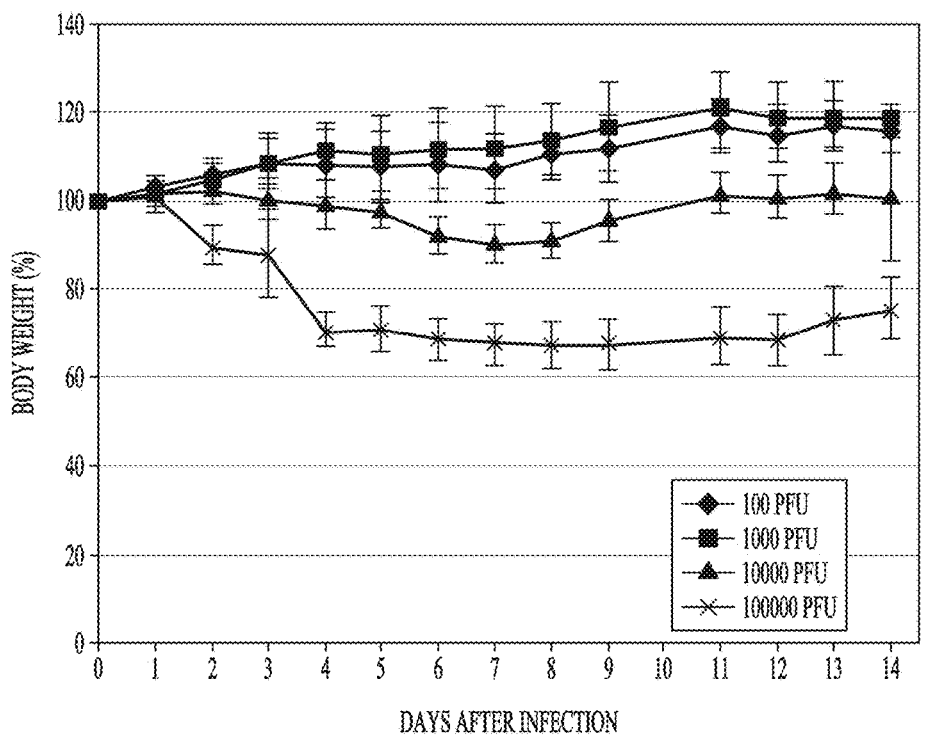
FIG. 9. Pathogenicity of a recombinant M2del11-HAavir virus. Mice were infected with 100, 1,000, 10,000, or 100,000 PFU of the M2del11-HAavir virus, and their body weights were monitored for 14 days. Data are reported as the mean changes in body weight±standard deviation (n=3).

To assess the amantadine sensitivity of these viruses, the M2 mutants and wild-type WSN-UdM viruses were plaqued in MDCK cells in the presence of different concentrations of amantadine. In cell culture, amantadine produces two discrete concentration-dependent inhibitory actions against viral replication. A nonspecific action at concentrations >50 μM, resulting from an increase in the pH of endosomes, inhibits activation of HA membrane fusion activity involved in endocytosis (Daniels et al., 1985); whereas at lower concentrations, 0.1-5 μM, the drug selectivity inhibits viral replication (Appleyard, 1977). As shown in FIG. 9, amantadine markedly reduced the yield of wild-type WSN-UdM virus, as well as the size of plaques, at each of the three test concentrations. By contrast, at 5 μM of amantadine, the replication of M2 mutant viruses was either not affected or inhibited only slightly. Substantial inhibition, due to the drugs nonspecific activity, was seen at 50 μM. Thus, all of the M2 mutants were more resistant to amantadine than the wild-type virus.

Generation of transfectant viruses in which the M2 TM domain was replaced with that from the HA or NA. Although the M2A30P, M2W41A, and M2del29-31 mutants do not have functional ion channel activity, as assayed by a two-electrode voltage-clamp procedure (Holsinger et al., 1994), they all replicated as well as the wild-type virus in MDCK cells (FIG. 8). Thus. M2 ion channel activity may not be essential for virus replication, although it could not be ruled out that low-level ion channel activity was below the sensitivity of the assay.

Figure 10A:
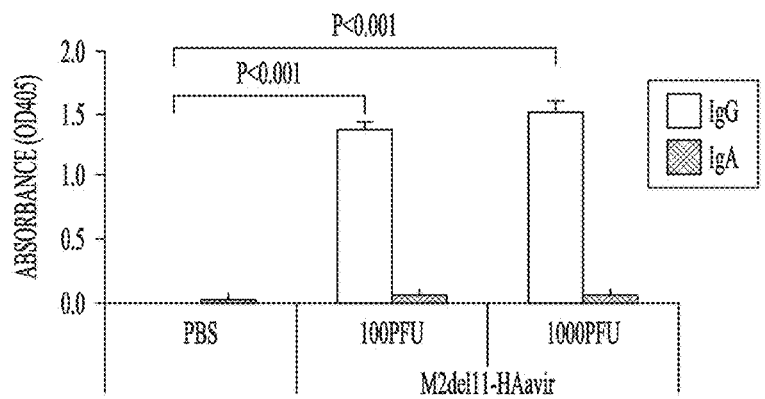
FIG. 10A-10C. Virus-specific serum and mucosal antibody responses in mice immunized with the M2del11-HAavir virus. Mice were immunized with 100 or 1.000 PFU of M2del11-HAavir virus intranasally. Samples from each group were obtained 3 weeks postimmunization. IgG and IgA levels in sera (A), lung washes (B), and nasal washes (C) from individual mice were detected by ELISA. Values are expressed as the mean absorbance±standard deviation (n=4) of undiluted samples (trachea-lung and nasal washes) or of samples diluted 1:10 (sera). Differences between responses to PBS and the M2del11-HA virus were tested for statistical significance by the use of Student's t test. M2del11-HAavir showed substantial levels of virus-specific IgG titers in serum and lung wash as well as IgA titers in lung wash, which increased with the immunization dose. These data indicate that M2del11-HAavir was able to induce strong antibody responses in mice.
Figure 10B:
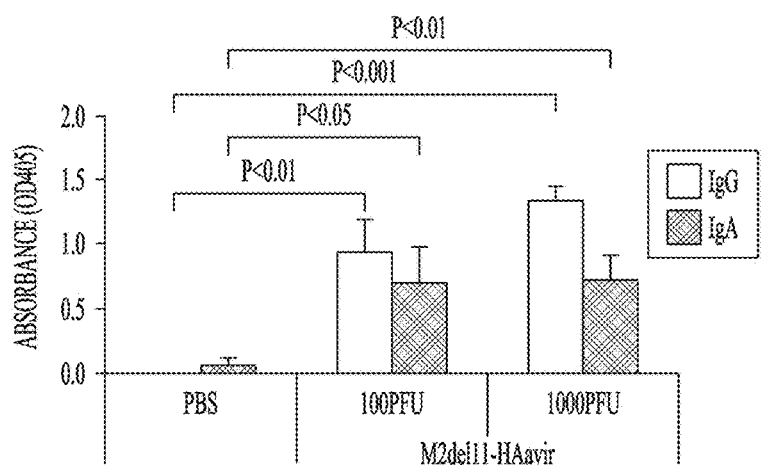
Figure 10C:
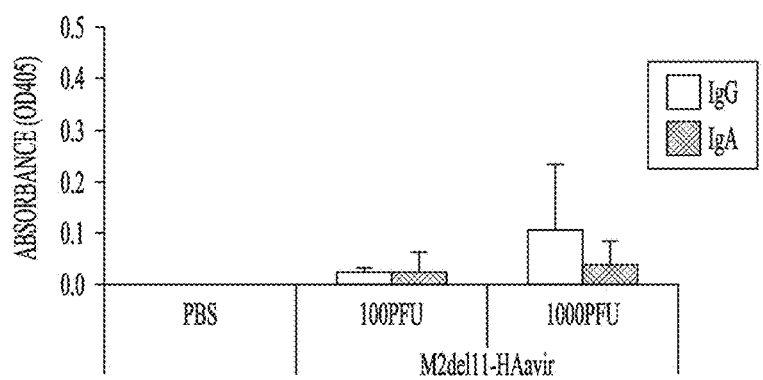

To determine whether M2 channel ion activity is not essential for viral replication, chimeric mutant viruses were generated in which the M2 TM domain was replaced with that from the HA or NA of the A/WSN/33 virus (FIG. 10). When the supernatant of 293T cells which had been transfected with plasmids was assayed for virus production, the chimeric mutants (M2HATM and M2NATM) were each viable, but their titers were more than one log lower than the wild-type WSN-UdM titer (Table 3). The mutants also produced pinpoint plaques after 48 hours of growth. Thus, the M2 TM domain is dispensable for viral replication in vitro.

Growth properties of the M2HATM mutant in tissue culture. Because the titers of the M2NATM virus stock did not exceed 10⁴ PFU/ml, the M2HATM virus was employed for further analysis, first by examining the time course of progeny virus production by M2HATM versus wild-type WSN-UdM viruses in MDCK cells (FIG. 8). Although M2HATM produced a lower titer than did the wild-type WSN-UdM virus at 12 and 24 hours postinfection, its maximum titer at 36 hours was almost the same as that of the wild-type virus. This result indicates that the absence of the M2 TM domain does not drastically impair the replicative ability of the virus in tissue culture.

Figure 11:
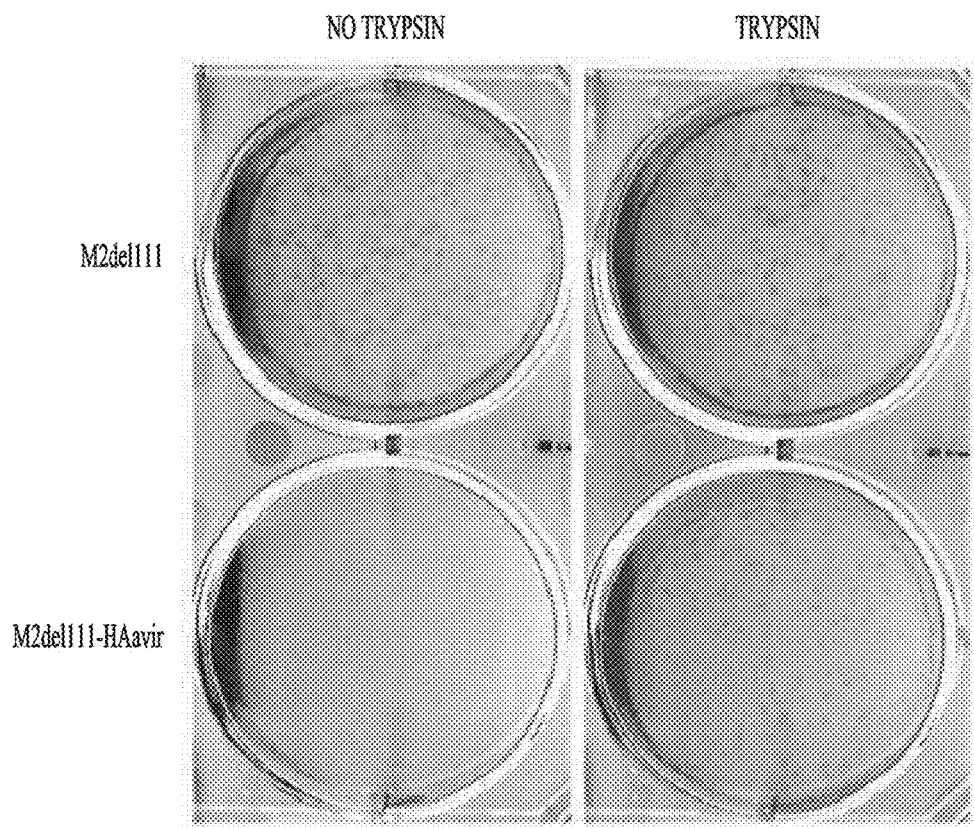
FIG. 11. Trypsin dependence of plaque formation of M2del11-HAavir virus in M2CK cells. Plaque assays were performed on M2CK cells in the presence or absence of trypsin. M2del11 virus was able to form plaques in both the presence and absence of trypsin. In contrast, with M2del11-HAavir mutant virus, clear plaques were visible only in the presence of trypsin.

Incorporation of mutant M2 molecules into virions. Conceivably, the M2 point and chimeric mutants possessed some residual ion channel activity, so that increased incorporation of the M2 protein into virions could compensate for any defect in this function. Therefore, the efficiency of incorporation of the wild-type and mutant M2s into influenza virions was compared using Western blot analysis after standardization based on the intensity of NP (FIG. 11). Virion incorporations of two mutant M2 proteins (M2del29-31 and M2HATM) was slightly less than that of the wild-type protein, although the W41A mutant was incorporated more efficiency. The band detected slightly below the M2 protein in the wild-type is probably a proteolytically cleaved form of M2, as reported by others (Zebedee and Lamb, 1988). An additional band below the NP protein that was reactive with anti-NP, but not anti-M2 antibody, is a cleavage product of NP (Zhimov and Bukrinskaya, 1984). Together, these results demonstrate that increased incorporation of M2 protein into virions does not seem to compensate for defective M2 ion channel activity.

Replication of M2 mutant viruses in mice. To determine the role of M2 ion channel activity in vivo, mice were infected with each of the six mutant viruses (Table 4), which replicated in the lungs as well as or more efficiently than the wild-type WSN-UdM virus, although the titer of the M2del29-31 virus was a log lower than that of the wild-type virus. By contrast, the mutants showed different replicative potentials in nasal, turbinates, with neither the M2A30P nor M2del29-31 virus recovered from such samples in any of the infected mice. M2HATM virus was not recovered from either the lungs or the nasal turbinates. These results indicate that M2 ion channel activity is necessary for efficient viral replication in vivo. Further, the serum of the infected mice have antibodies which bind to the immunizing virus (see Example 3).

TABLE 4

Replication of M2 mutants in mice[a]
Mean titers ($\log_{10}$PFU/g) ∀ SD

| Virus | Nasal turbinate | Lung |
|---|---|---|
| Wild-type | 3.9 ± 0.5 | 6.8 ± 0.3 |
| M2V27T | 4.3 ± 0.7 | 7.3 ± 0.3 |
| M2A30P | NR[b] | 6.8 ± 0.1 |
| M2S31N | 4.3 ± 0.4 | 7.0 ± 0.2 |
| M2W41A | 3.1 ± 2.2[c] | 6.7 ± 0.2 |
| M2del29-31 | NR | 5.6 ± 0.1 |
| M2HATM | NR | NR |

[a]Five-week-old female BALB/c mice (n = 4), anesthetized with isoflurane, were infected intranasallly with 50 μl of virus (5 × 10³ PFU). Virus titers in organs were determined 3 days after infection with MDCK cells.
[b]NR, virus was not recovered from any of the infected mice (less than 10² PFU/g).
[c]Virus was recovered from only three of the four mice infected.

Discussion

A reverse-genetics system (Neumann et al., 1999) was used to generate transfectant influenza A viruses with changes in the M2 protein TM domain that are known to block ion channel activity. Despite this functional defect, all of the mutant viruses replicated as efficiently as the wild-type WSN-UdM virus in vitro. The dispensability of M2 ion channel activity in viral replication was reinforced by experiments in which the TM domain of the M2 protein was replaced with that from the HA or NA. Thus, in in vitro studies, influenza A viruses did not require M2 ion channel activity for efficient replication.

M2 ion channel activity is believed to function at an early stage in the viral life cycle, between the steps of host cell penetration and uncoating of viral RNA. Zhimov et al. (1990) reported that low pH induces the dissociation of M protein from viral RNPs in vitro. This observation lead others to suggest that the introduction of protons into the interior of virions through M2 ion channel activity in the endosomes is responsible for M dissociation from RNP (reviewed by Helenius. 1992). If so, how could this process occur in the absence of M2 ion channel activity or the M2 TM domain? Immunoelectron microscopy of the HA protein in virosomes exposed to low pH demonstrated that, in the absence of target membranes, the N-terminal fusion peptide of the HA2 subunit was inserted into the same membrane site where HA was anchored (Wharton et al., 1995). Therefore, one possibility is that the fusion peptide of the HA maybe inserted into the viral envelope, forming pores in the viral membrane that permit the flow of protons from the endosome into virus interior, resulting in disruption of RNP-M1 interaction. Alternatively, M1 may be able to dissociate from RNP by an entirely different mechanism, including ion channel activity by the TM regions of other viral membrane proteins, such as the HA, the NA or both.

What is the origin of the M2 ion channel? The M2 ion channel activity was originally discovered with A/fowl plague/Rostocki/34 (FPV Rostock) strain, which has intracellularly cleavable HA (Sugreu et al., 1990; Ohuchi et al., 1994; Takeuchi and Lamb, 1994). In this strain, the HA undergoes a low pH-induced conformational change in the trans-Golgi network in the absence of M2 ion channel activity, which raises the pH in this compartment. Hence, in the past, influenza A viruses may have been equipped with an M2 protein that promoted an increase in the pH of the trans-Golgi network, to a level above which conformational changes occur in the intracellularly cleavable HA. As influenza A viruses without intracellularly cleavable HAs began to appear, there was less selective pressure to maintain high ion channel activity associated with the M2 protein. Consequent decreases in this activity may have been sufficient to allow dissociation of M1 from RNP. Indeed, ion channel activity differs markedly among the M2 proteins of currently recognized viruses: for example, fivefold more M2 protein from human Udorn virus (containing intracellularly uncleavable HA) is needed to produce the same ion channel activity displayed by an equivalent amount of M2 from FPV Rostock virus (containing intracellularly cleavable HA) (Takeuchi and Lamb, 1994). Conversely, the HAs of some influenza A viruses have changed from intracellularly uncleavable to cleavable during replication in chickens (Kawaoka et al., 1984; Horimoto and Kawaoka, 1995; Horimoto et al., 1995), suggesting that M2 protein with limited ion channel activity could acquire greater activity once a switch to intracellularly cleavable HA has occurred.

The M2 ion channel knock-out and M2HATM viruses replicated reasonably well in tissue culture, but were highly attenuated in mice, raising the possibility for their use as live vaccines. Cold-adapted live vaccines, now in clinical trials (reviewed by Maasab and Bryant, 1999), hold considerable promise for use in the general population (Sears et al., 1988; Steinhoff et al., 1991; Steinhoff et al., 1990). The major concern is that the limited number of attenuating mutations in such vaccines (Cox et al., 1988; Herlocher et al., 1993)

could permit the generation of revertant viruses. Abolishing the M2 ion channel activity, for example, by replacing the M2 TM domain with that from the HA, would greatly reduce the likelihood of the emergence of revertant viruses. Thus, using our new reverse-genetics system, the generation of influenza viruses with modified viral genes could lead to the production of safe live influenza vaccines.

To date, four viral proteins have been reported to act as ion channels: M2 of influenza A virus, NB or influenza B virus, and Vpu and Vpr of human immunodeficiency virus type 1 (HIV-1) (Ewart et al., 1996; Piller et al., 1996; Pinto et al., 1992; Schubert et al., 1996; Sunstrom et al., 1996). Since the replication strategies of influenza type A and B viruses are very similar, the NB ion channel activity is also thought to play a role at an early stage of the viral life cycle, although NB still lacks a demonstrated function in viral replication. Although the Vpu protein of HIV-1 enhances the release of virus particles from cells (Schubert et al., 1995; Strebel et al., 1988; Terwilliger et al., 1989), its gene can be deleted without completely abrogating HIV-1 replication in vitro (Cohen et al., 1988; Klimkait et al., 1990; Strebel et al., 1988, 1989). Vpr, another HIV-1 auxiliary protein, is likewise not essential for replication in tissue culture (Dedera et al., 1989). Finally, here, it was shown that M2 ion channel activity is not essential for the life cycle of influenza A viruses. Therefore, ion channel activities of viral proteins may be an auxiliary function in general, although they can promote more efficient viral replication under certain conditions such as in vivo, as shown hereinabove.

EXAMPLE 3

Materials and Methods

Cells and viruses. 293T human embryonic kidney cells and Madin-Darby canine kidney (MDCK) cells were maintained in DMEM supplemented with 10% FCS and in MEM containing 5% newborn calf serum, respectively. The 293T cell line is a derivative of the 293 line, into which the gene for the simian virus 40 T antigen was inserted (Dubridge et al., 1987). All cells were maintained at 37EC in 5% $CO_2$. M2del29-31 and WSN-UdM (wild-type) viruses were propagated in MDCK cells. A/WSN/33 (H1N1) virus was propagated in 10-day-old embryonated chicken eggs.

Immunization and protection tests. BALB/c mice (4-week-old female) were intranasally immunized with 50 μl of $1.1 \times 10^5$ PFU per ml of M2del29-31 or wild-type WSN-UdM viruses. On the second week, four mice were sacrificed to obtain sera, trachea-lung washes, and nasal washes. Two weeks and one or three months after the vaccination, immunized mice were challenged intranasally, under anesthesia, with 100 $LD_{50}$ doses of the wild-type WSN virus. For determination of virus titers, lungs were harvested at day 3 and were homogenized and titrated on MDCK cells. The remaining animals were observed for clinical signs and symptoms of infection for 14 days after challenge.

Detection of virus-specific antibody. Serum samples were examined for antibody by ELISA. In this assay, the wells were coated with purified WSN virus after treatment with 0.05 M Tris-HCl (pH 7.8) containing 0.5% Triton X-100 and 0.6 M KCl at room temperature and diluted in PBS. After incubation of virus-coated plates with test serum samples, bound antibody was detected with rabbit anti-mouse IgA (Kirkegaard & Penrry Laboratories Inc., Gaithersburg, Md.) and goat anti-mouse IgG (Boehringer Mannheim, Germany) conjugated to horseradish peroxidase.

Results

In the second week after immunization, virus-specific IgG and IgA was found in nasal washes, lung washes and sera of immunized mouse. Notably, virus specific IgG was found in greater levels in mice immunized with M2del29-31 virus in all three sample types, and virus-specific IgA was found in lung washes from M2del29-31-immunized mice but was undetectable in lung washes from WSN-UdM-immunized mice.

The mice were challenged with wild-type virus two weeks, one month or two months after immunization and body weights determined for up to 2 weeks (FIG. 13). The body weights of mice immunized with M2del29-31 virus and challenged with wild-type virus remained relatively constant regardless of the timing between immunization and challenge while the body weights of mice immunized with wild-type virus and later challenged with wild-type virus dropped precipitously after challenge regardless of the timing between immunization and challenge.

The lungs from some of the mice were harvested at day 3 after challenge to determine virus titers (Table 5). Only mice that were immunized with wild-type virus and challenged with wild-type virus had detectable virus in the lungs. The lack of the presence of virus in lung of immunized mice which were challenged correlated with survival after challenge.

TABLE 5

Protection against virus challenge in immunized mice[a]

| Immunogen | No. survivors/no. tested | Virus titer in lungs [$\log_{10}$(PFU/g)] |
|---|---|---|
| 2 weeks | | |
| control | 0/4 | 7.5 ± 0.1 |
| del29-31 | 4/4 | 0 |
| 1 month | | |
| control | 0/4 | 7.4 ± 0.1 |
| del29-31 | 4/4 | 0 |
| 3 months | | |
| control | 0/4 | 7.2 ± 0.1 |
| del29-31 | 4/4 | 0 |

[a]BALB/c mice (4-week-old female) were intranasally immunized with 50 μL of $1.1 \times 10^5$ PFU per ml of M2del29-31 or wild-type WSN-UdM virus. Two weeks, or one or three months after the vaccination, immunized mice were challenged intranasally with 100 $LD_{50}$ doses of the wild-type WSN virus. For determination of virus titers, lungs were harvested at day 3 and were homogenized and titrated on MDCK cells. The remaining animals were observed for clinical signs and symptoms of infection for 14 days after challenge.

EXAMPLE 4

Materials and Methods

Cells. 293T human embryonic kidney cells and Madin-Darby canine kidney (MDCK) cells were maintained in Dulbecco's modified Eagle's medium supplemented with 10% fetal calf serum and in minimal essential medium (MEM) containing 5% newborn calf serum, respectively. All cells were maintained at 37° C. in 5% $CO_2$. Hygromycin-resistant MDCK cells stably expressing M2 protein from A/Puerto Rico/8/34 (H1N1) were established by cotransfection with plasmid pRHyg, containing the hygromycin resistance gene, and plasmid pCAGGS/M2, expressing the full-length M2 protein, at a ratio of 1:1. The stable MDCK cell clone (M2CK) expressing M2 was selected in medium containing 0.15 mg/mL of hygromycin (Roche, Mannheim, Germany) by screening with indirect immunostaining using an anti-M2 (14C2) monoclonal antibody. The M2CK cells were cultured in MEM supplemented with 10%/o fetal calf serum and 0.15 mg/mL of hygromycin. In M2CK cells, the expression levels and localization of M2 were similar to those in virus-infected cells (data not shown).

Plasmid construction. The cDNA of A/Vietnam/1203/04 (VN1203) virus was synthesized by reverse transcription of viral RNA with an oligonucleotide complementary to the conserved 3' end of the viral RNA, as described by Katz et al. (1990). The cDNA was amplified by PCR with M gene-specific oligonucleotide primers containing BsmBI sites, and PCR products were cloned into the pGEM vector. The resulting construct was designated pGEM-VN 1203M. After digestion with BsmBI the fragment was cloned into the BsmBI sites of the pHH21 vector, which contains the human RNA polymerase I promoter and the mouse RNA polymerase I terminator, separated by BsmBI sites, resulting in pPolIUdM. Plasmids derived from pHH21 for the expression of viral RNA are referred to as "PolI" constructs herein.

The M mutants were constructed as follows. pGEM-VN1203M was first amplified by inverse PCR (Ochmann et al., 1988) using the back-to-back primers M987stopF (5'-gtgaATAGAATTGGAGTAAAAAACTACC-3'; SEQ ID NO:35) and M987stopR (5'-tcaAAAATGACCATCGT-CAACATCCAC-3'; SEQ ID NO:36), M969stopF (5'-gt-gaGATGGTCATITTGTCAACATAGAA-3'; SEQ ID NO:37) and M969stopR (5'-tcaATCCACAGCACTCTGCT-GTTCCTG-3'; SEQ ID NO:38), M936stopF (5'-gtgaCG-GCAGGAACAGCAGAGTGCTG-3'; SEQ ID NO:39) and M936stopR (5'-tcaTrCCCTCATAGACTCAGGTACC-3'; SEQ ID NO:40), M903stopF (5'-gtgaGCAGGGGTACCT-GAGTCTATG-3'; SEQ ID NO:41) and M903stopR (5'-tcaAGGCCCTCTUTTCAAACCGTA-3'; SEQ ID NO:42), M870stopF (5'-CTTAAATACGGTTTGAAAAGAGGGC-CTGC-3'; SEQ ID NO:43) and M870stopR (5'-tcact-caATAAATGCATTTGAAGAAAAGACGATC-3'; SEQ ID NO:44), and M783stopF (5'-TTGTTGTTGCCGCAAATAT-CATTGGG-3'; SEQ ID NO:45) and M783stopR (5'-Ttcact-caACTTGAATCGCTGCATCTGC-3'; SEQ ID NO:46). Nucleotide changes to introduce stop codons are indicated by lowercase letters.

The PCR products were then phosphorylated, self-ligated, propagated in *Escherichia coli* strain DH5α, and then digested with BsmBI and cloned into the BsmBI sites of the pHH21 vector. The resulting constructs were designated pPolI-VN1203M2del5, pPolI-VN1203M2del11, pPolI-VN1203M2del22, pPolI-VN1203M2del33, pPolI-VN1203M2del44, and pPolI-VN1203delM2, each of which contained two stop codons at nucleotide positions 972 to 974, 939 to 941, 906 to 908, 873 to 875, and 786 to 788 of the M segment, which resulted in the deletion of 5, 11, 22, 33, 44, and 70 residues from the C terminus of the M2 protein, respectively (FIG. 7). All of the constructs were sequenced to ensure that unwanted mutations were not present.

Plasmid-driven reverse genetics. All of the viruses were generated by the introduction of plasmids expressing eight viral RNA segments and three polymerase proteins plus NP, as described by Neumann et al. (1999). At 48 hours post-transfection, viruses were harvested and used to inoculate M2CK cells for the production of stock viruses. The M genes of transfectant viruses were sequenced to confirm the origin of the gene and the presence of the intended mutations and to ensure that no unwanted mutations were present. All experiments with live viruses and with transfectants generated by reverse genetics were performed in a biosafety level 3 containment laboratory approved for such use by the CDC and the U.S. Department of Agriculture.

Replicative properties of the transfectant viruses in cell culture. MDCK cells were infected in duplicate wells of 24-well plates with the wild-type or mutant viruses at a multiplicity of infection (MOI) of 0.001, overlaid with MEM containing 0.5 μg of trypsin per mL, and incubated at 37° C. At select time points, supernatants were assayed for infectious virus in plaque assays on M2CK cells (Iwatsuki-Horimoto et al., 2006).

Experimental infection. Five-week-old female BALB/c mice, anesthetized with isoflurane, were infected intranasally with 50 μL (100 PFU) of virus. Virus titers in organs were determined 3 days after infection by use of MDCK cells, as described in Bilsel et al. (1993).

Immunization and protection. BALB/c mice (4-week-old females) were intranasally immunized with 100 or 1,000 PFU/50 μL of the M2del11-HAavir virus. Three weeks later, four mice were sacrificed to obtain sera, trachea-lung washes, and nasal washes. One month after vaccination, immunized mice were challenged intranasally, under anesthesia, with $3.8\times10^2$ PFU or $5\times10^4$ PFU of the wild-type VN1203 or A/Indonesia/7/05 virus, which was equivalent to 100 50% minimal lethal doses ($MLD_{50}$) (dose required to kill 50% of infected mice), respectively. To determine virus titers in mice, organ samples were harvested at day 3 postchallenge and were homogenized and titrated on MDCK cells. The remaining animals were observed for clinical signs and symptoms of infection for 14 days postchallenge.

Virus-specific antibody detection. Immunoglobulin G (IgG) and IgA antibody titers were measured in sera, trachea-lung washes, and nasal washes of the immunized mice by use of an enzyme-linked immunosorbent assay (ELISA) (Kida et al., 1982). In this assay, the wells were coated with purified A/Vietnam/1194/05 virus after treatment with 0.05 M Tris-HCl (pH 7.8) containing 0.5% Triton X-100 and 0.6 M KCl at room temperature for 1 hour and then diluted in phosphate-buffered saline (PBS). After incubation of virus-coated plates with test serum samples for 1 hour, bound antibody was detected with a rabbit anti-mouse IgA (Kirkegaard & Perry Laboratories Inc., Gaithersburg. Md.) and a goat anti-mouse IgG (Boehringer, Mannheim, Germany) conjugated to horseradish peroxidase. Neutralizing antibody titers in serum samples of the immunized mice were also evaluated. The sera were treated with receptor-destroying enzyme (Accurate Chemical and Scientific Corp.) to destroy inhibitors of influenza virus replication. After inactivation of the receptor-destroying enzyme by treatment at 56° C. for 30 minutes, VN1203 and A/Indonesia/7/05 viruses were each incubated with twofold serial dilutions of serum (starting at a 1:10 dilution) at 37° C. for 1 hour. Viral infectivity was determined by titration of the samples in a plaque assay on MDCK cells. The neutralizing titer was defined as the reciprocal titer of serum required to neutralize at least 50% of each virus.

Results

In vitro 2growth properties of VN1203 viruses possessing M2 cytoplasmic tail deletion mutations. A series of M2 cytoplasmic tail deletion mutants of a highly pathogenic H5N1 (VN1203) virus was generated by reverse genetics as described in Neumann et al. (1999). Transfectant viruses were harvested at 48 hours posttransfection and used to inoculate M2CK cells to propagate stock viruses. The stock virus titers were comparable to that of the wild-type virus: $6.2\times10^8$ PFU/mL for VN1203M2del44, $6.8\times10^8$ PFU/mL for VN1203M2del33, $6.3\times10^8$ PFU/mL for VN1203M2del22, $5.4\times10^8$ PFU/mL for VN1203M2dl11, $6.1\times10^8$ PFU/mL for VN1203M2del5, and $2.4\times10^8$ PFU/mL for the wild-type virus. The only exception was VN1203delM2 (6.0×10⁶ PFU/mL).

Next, the growth properties of the VN1203M2 tail mutant viruses were compared with those of wild-type VN1203 virus in MDCK cells (FIG. 8). MDCK cells were infected with viruses at an MOI of 0.001, and their growth kinetics were monitored for 72 hours. The VN1203M2del5 and -M2del11 viruses grew as well as the wild-type virus. By contrast, the VN1203M2del22, -M2del33, and -M2del44 viruses replicated less efficiently than the wild-type virus (1,000 to 10,000-fold-lower growth). In particular, the VN1203delM2 virus, which lacks both the transmembrane and cytoplasmic tail domains, was significantly growth restricted on MDCK cells (100,000-fold-lower growth than the wild-type virus). These results are consistent with previous findings that mutant viruses with deletions at the C terminus of the M2 tail grew less well in cell culture (Itwasuki-Horimoto et al., 2006; McCown et al., 2006; McCown et al., 2005).

In vivo growth properties of VN1203 M2 tail deletion mutants. To determine the virulence of the M2 tail mutants, their growth properties in mice were examined. Mice were infected with 100 PFU of M2 mutant or wild-type viruses. On day 3 postinfection, organs were taken from the infected mice for virus titration. As shown in Table 6, the wild-type VN1203 virus replicated well in all organs examined. Mutants possessing deletions of more than 22 amino acids were not recovered from any of the infected mice. Of interest, replication of the VN1203M2del5 and -M2del11 viruses was more than 1 log lower in the lungs, 2 logs lower in nasal turbinates, and 2 logs lower in the kidneys of infected mice than that of wild-type virus. Moreover, no virus was detected from the brain samples of mice infected with the VN1203M2del11 virus. These results indicate that the VN1203M2del11 virus was attenuated in mice, despite replicating as well as the wild-type virus in MDCK cells.

and viral replication to a limited number of organs (i.e., these viruses cause localized infections). By contrast, the HAs of highly pathogenic H5N1 avian influenza viruses contain a series of basic amino acids at this site (Bosch et al., 1981; Garten et al., 1981; Senne et al., 1996; Suarez et al., 1995), which allow HA to be cleaved not only by trypsin but also by ubiquitous cellular proteases (Horimoto et al., 1994; Stieneke-Grober et al., 1992), thereby allowing viral replication in a variety of organs, including brain (i.e., these viruses cause systemic infections). To ensure the safety of the vaccine strains, a mutant HA was constructed in which the amino acid sequence at the HA cleavage site, PQR-ERRRKKR/G (SEQ ID NO:47), was converted to the sequence in a typical avirulent avian virus, PQ-RETR/G (dashes indicate deletions; SEQ ID NO:48). A recombinant virus possessing this avirulent HA and M2del11 mutations (designated M2del11-HAavir) was generated. Stock virus was amplified on M2CK cells, and the virus titer was 2.0×10⁶ PFU/mL.

Characterization of the recombinant M2del11-HAavir virus in vitro and in vivo. To characterize the M2del11-HAavir virus, its trypsin dependency in vitro was examined. Plaque assays were performed on M2CK cells in the presence or absence of trypsin. With the M2del11-HAavir virus, clear plaques were visible only in the presence of trypsin, whereas the M2del11 virus formed plaques in both the presence and absence of trypsin (data not shown).

Next, to investigate the virulence of the M2del11-HAavir virus in vivo, mice were infected with various doses of the virus and monitored for 14 days (FIG. 9). Even at a high dose (1×10⁵ PFU), the virus did not kill any mice (the $MLD_{50}$ was >10⁵ PFU, compared to 2.1 PFU for the wild-type VN1203 virus [data not shown]), although slight weight

TABLE 6

Replication of M2 mutant viruses in mice

| Virus | Virus titer (mean $\log_{10}$ PFU/g ± SD) in[a]: | | | | |
|---|---|---|---|---|---|
| | Lungs | Nasal turbinates | Brains | Spleens | Kidneys |
| Wild-type | 8.41 ± 0.09 | 6.66 ± 0.85 | 5.02 ± 1.56 | 7.48 ± 0.48 | 6.23 ± 0.82 |
| VN1203M2del5 | 7.47 ± 0.29 | 4.70 ± 1.21 | 3.60, 3.51 | 5.54 ± 0.85 | 3.90, 4.03 |
| VN1203M2del11 | 7.30 ± 0.45 | 4.06, 4.74 | ND[b] | 3.97 ± 0.81 | 4.24 |
| VN1203M2del22 | ND | ND | ND | ND | ND |
| VN1203M2del33 | ND | ND | ND | ND | ND |
| VN1203M2del44 | ND | ND | ND | ND | ND |
| VN1203delM2 | ND | ND | ND | ND | ND |

[a]Mice were infected with 100 PFU of M2 mutant or wild-type virus. Organ samples were taken from mice at day 3 postinfection. Virus titers were determined with M2CK cells. When virus was not recovered from all three mice, individual titers were recorded.
[b]ND, not detected.

Generation of a recombinant VN1203 virus that possesses M2del11 and an avirulent HA. Since the VN1203M2del11 virus was attenuated in mice, the feasibility of using it for an H5N1 vaccine was tested. To improve the safety of an H5N1 virus vaccine, vaccine candidates should have multiple attenuating mutations in the viral genes. Therefore mutations were introduced into the cleavage site of the VN1203M2del11 virus HA, a virulence determinant of influenza viruses in birds and mammals (Halta et al., 2001; Klenk et al., 1994; Steinhauer et al., 1999). In general, low-pathogenicity viruses do not contain a series of basic amino acids at the HA cleavage site (Klenk et al., 1994; Senne et al., 1996; Steinhauer, 1999), restricting cleavage loss was observed (FIG. 9). Mice infected with 100 or 1,000 PFU of the M2del11-HAavir virus did not show any weight loss. Organ tropisms for the M2del11-HAavir virus in mice were also examined. As shown in Table 7, the virus titers were 1 log lower in the lungs of mice infected with 100 PFU of the M2del11-HAavir virus than in those of mice infected with the wild-type virus. No virus was detected in the other organs of M2del11-HAavir-infected mice. Even in the mice infected with a high dose (1,000 PFU) of M2del11-HAavir, the virus was recovered only from the lungs and nasal turbinates, indicating that virus replication was restricted to the respiratory tracts. These results suggest that the M2del11-HAavir virus was highly attenuated in mice.

TABLE 7

Replication of M2delII-HAavir virus in mice

| Dose (PFU/mouse) | Virus titer (mean log$_{10}$ PFU/g ± SD) in[a]: | | | | |
|---|---|---|---|---|---|
| | Lungs | Nasal turbinates | Brains | Spleens | Kidneys |
| 100 | 6.38 ± 1.28 | ND[b] | ND | ND | ND |
| 1,000 | 6.77 ± 0.17 | 3.67 ± 1.25 | ND | ND | ND |

[a]Mice were infected with 100 or 1,000 PFU of M2 del11-HAair virus. Organ samples were taken from mice at day 3 postinfection. Virus titers were determined with M2CK cells.
[b]ND, not detected.

Antibody responses of mice immunized with the M2del11-HAavir virus. To test the efficacy of the M2del11-HAavir virus as a vaccine, mice were intranasally administered with 100 or 1,000 PFU of the M2del11-HAavir virus. Three weeks later, IgG and IgA levels in sera, trachea-lung washes, and nasal washes of immunized mice were measured by means of an ELISA (FIG. 10). Both IgG and IgA levels in trachea-lung washes were significantly higher in mice immunized with the M2del11-HAavir virus than in those treated with a PBS control, although there was no significant difference between the antibody titers in nasal washes from the vaccine group and the control group. The IgA response was negligible in serum, regardless of the dose of the mutant virus used for immunization, but IgG production was clearly higher in mice inoculated with the M2del11-HAavir virus. These data suggest that the M2del11-HAavir virus elicited a significant antibody response in the immunized mice.

To examine whether or not the antibodies detected by ELISA contribute to neutralization of the H5N1 virus infectivity, the infectivity-neutralizing activity of the samples against VN1203 (homologous virus; clade 1) and A/Indonesia/7/2005 (Indonesia 7) (heterologous virus; clade 2), whose HA homology is 96.5% at the amino acid level was tested. Immunization with 1,000 PFU of M2del11-HAavir virus did not elicit neutralizing antibody efficiently, and the reciprocal titers of serum required to neutralize 50% of VN1203 and Indonesia 7 were only 31 and 23, respectively (data not shown). Moreover, no neutralizing antibody was detectable in sera from mice immunized with 100 PFU of M2del11-HAavir virus (data not shown), indicating that only a limited level of neutralizing antibody was elicited upon immunization of mice with the M2del11-HAavir virus despite high levels of protection upon lethal challenge and high levels of IgG detected by ELISA.

Protective efficacy of the M2del11-HAavir virus in mice. Mice immunized with the M2del11-HAavir virus were challenged 1 month after immunization with 100 MLD$_{50}$ of the wild-type VN1203 virus (clade 1) or Indonesia 7 (clade 2). Unlike control mice, all M2del11-HAavir-immunized mice survived a lethal challenge with either of the highly pathogenic H5N1 viruses (data not shown) and did not show any symptoms, including weight loss, after the challenge. By contrast, all of the control mice died or had to be euthanized due to their symptoms by day 8 postchallenge (data not shown). The virus titers in several organs of the mice challenged with the VN1203 or Indonesia 7 virus (Table 8) was also determined. High titers of viruses were recovered from all organs of the control group. No virus was detected from any of the organs in the M2del11-HA virus vaccine group challenged with VN1203, though a limited amount of virus was detected in the nasal turbinates of one of the immunized mice challenged with the Indonesia 7 virus (Table 7). Taking the results together, it was concluded that the M2del11-HAavir virus can confer protective immunity to mice against lethal challenge with highly pathogenic H5N1 virus.

TABLE 8

Replication of M2 mutant viruses in mice

| Challenge Virus | Group | Virus titer (mean log$_{50}$ PFU/g ± SD) in[a]: | | | | |
|---|---|---|---|---|---|---|
| | | Lungs | Nasal turbinates | Brains | Spleens | Kidneys |
| VN1203 | PBS | 7.83 ± 0.46 | 6.11, 4.19 | 3.04 | 4.96 ± 0.66 | 2.78, 4.27 |
| | M2del11-HAavir | | | | | |
| | 100 PFU | ND[b] | ND | ND[b] | ND | ND |
| | 1,000 PFU | ND | ND | ND | ND | ND |
| Indonesia 7 | PBS | 9.06 ± 0.10 | 7.01 ± 0.21 | 3.32 ± 1.37 | 5.64 ± 0.12 | 4.27 ± 0.38 |
| | M2del11-HAavir | | | | | |
| | 100 PFU | ND | ND | ND | ND | ND |
| | 1,000 PFU | ND | 1.96 | ND | ND | ND |

[a]Three mice from each group were sacrificed on day 3 postchallenge for virus titration. When virus was not recovered from all three mice, individual titers were recorded.
[b]ND, not detected.

Discussion

The influenza A virus M2 is a multifunctional protein. It has ion channel activity in its transmembrane domain (Pinto et al., 1982), which is thought to function at an early stage of replication (acidification of the virion interior) (Helenius, 1992; Martin et al., 1991; Sugrue et al., 1991) and at a late stage (protection of an acid-mediated conformational change of cleaved HA) (Hay et al., 1985; Ohuchi et al., 1994; Takeuchi et al., 1991). In addition, its cytoplasmic tail is important for viral assembly (Itwasuki-Horimoto et al., 2006; McCown et al., 2006; McCown et al., 2005). In this study, a series of M2 tail deletion mutants was generated and their growth properties in vitro and in vivo examined. Deletions of 5 or 11 amino acids from the C terminus of M2 were found to not affect virus replication in cell culture but inhibited virus growth in mice. Previously it was shown that even one amino acid deletion from the M2 C terminus attenuated influenza virus in ferrets (Castrucci et al., 1995). Those findings indicate that the M2 cytoplasmic tail has a vital role(s) in virus replication in animals and that M2 tail mutants could be good vaccine candidates for influenza virus infection. Here, it was demonstrated that H5N1 M2del11-HAavir virus, which has an 11-amino-acid deletion from the C terminus of its M2 protein and an avirulent HA, protected mice from a lethal challenge with H5N1 viruses, indicating its considerable potential as a live virus vaccine against highly pathogenic H5N1 viruses.

Recently, Suguitan et al. (2006) tested the vaccine efficacy in mice and ferrets of live attenuated, cold-adapted virus vaccine candidates that possess the modified avirulent type of HA and the NA from H5N1 strains, together with the internal genes from cold-adapted A/Ann Arbor/6/60 (H2N2). They demonstrated that a single dose of the vaccine protected animals from lethality but did not fully protected them from replication of the challenge H5N1 viruses, indicating limited efficacy for single-dose vaccination of these cold-adapted viruses. This incomplete protection may stem from unmatched antigenicity between the internal proteins of the cold-adapted virus (i.e., derived from H2N2 virus) and the challenge virus. Here, it was shown that the M2del11-HAavir virus, whose eight genes are derived from an H5N1 virus, protects mice almost completely from replication of heterologous H5N1 virus as well as homologous virus (Table 7). Despite its complete protection, the M2del11-HAavir virus did not elicit neutralizing antibody against either homologous or heterologous viruses efficiently, whereas it elicited high levels of antibodies detected by ELISA (FIG. 10). Therefore, cytotoxic T-lymphocyte responses specific to viral internal proteins that contain common cytotoxic T-lymphocyte epitopes among influenza A viruses (i.e., NP and M proteins) and mucosal immune responses may be responsible for the cross-protection observed in this study, as suggested in Takeda et al. (2003). If a vaccine against pandemic influenza is introduced only once a pandemic is imminent, all of the eight genes of the vaccine candidates could be derived from the pandemic strain to offer optimal protection to humans from virus infection. To reduce the risk of the emergence of the revertants, live attenuated virus vaccines should have multiple attenuating mutations in the genes that encode their internal proteins. NS1 mutant viruses are highly attenuated in mice because they lack interferon antagonist activity while retaining the ability to induce protective immunity against influenza virus challenge (Talon et al., 2000). Hence, by combining a mutant NS1 protein with the M2 tail deletion mutants identified in this study, an improved "master" influenza virus could be produced as a first step in the production of safe live influenza vaccines. Continued progress in understanding the functions of these influenza virus proteins should allow the introduction of multiple mutations in live vaccine strains, in addition to those in the HA, NS, and M genes, thereby reducing the likelihood of the emergence of pathogenic revertant viruses.

For live attenuated H5N1 virus vaccines to be clinically useful, the binding specificity of H5 HA for α-2,3-linked sialic acid (SA) receptors, which are preferentially recognized by avian influenza virus and rarely present in the upper respiratory tract of humans (Conner et al., 1994; Rogers et al., 1989; Rogers et al., 1983), must be considered. To address this problem, one could modify the H5 HA to alter its specificity for SA receptors. Recently, Auewarakul et al., 2007. Yamada et al., 2006; Yang et al., 2007 have determined specific amino acids in the avian H5 HA that alter its receptor-binding specificity toward α-2,6-SA (human-type receptor) recognition. This strategy may allow the generation of a recombinant H5N1-based vaccine that recognizes human-type α-2,6-SA receptors and efficiently replicates in the upper respiratory tract in humans.

REFERENCES

Albo et al., *J. Virol.*, 70:9013 (1996).
Appleyard. *Gen. Virol.*, 3:249 (1977).
Auewarakul et al., *J. Virol.*, 81:9950 (2007).
Bilsel et al., *J. Virol.*, 67:6762 (1993).
Bosch et al., *Virology*, 113:725 (1981).
Bresson et al., *Lancet*. 367:1657 (2006).
Bridgen et al., *Proc. Natl. Acad. Sci. U.S.A.*, 93:15400 (1996).
Castrucci et al., *J. Virol.*, 66:4647 (1992).
Castrucci et al., *J. Virol.*, 69:2725 (1995).
Cheung et al., *J. Infect. Dis.*, 193:1626 (2006).
Claas et al., *Lanct.*, 351:472 (1998).
Connor et al., *Virology*. 205:17 (1994).
Cox et al., *Virology*. 167:554 (1988).
Daniels et al., *Cell*, 40:431 (1985).
de Jong et al., *N. Engl. J. Med.*, 353:2667 (2005).
Dedera et al., *J. Virol.*, 63:3205 (1989).
DuBridge et al., *Mol. Cell Biol.*, 2:379 (1987).
Duff et al., *FEBS Lett.*, 311:256 (1992).
Duff et al., *Virology*, 190, 485-489 (1992).
Dunn et al., *Virology*, 211:133 (1995).
Enami et al., *J. Virol.*, 65:2711 (1991).
Enami et al., *Proc. Natl. Acad. Sci. U.S.A.*, 87:3802 (1990).
Enami et al., *Virology*, 185:291 (1991).
Ewald et al., *J. Virol.*, 70:7108 (1996).
Gao et al., *J. Virol.*, 73:3184 (1999).
Garten et al., *Virology*. 115:361 (1981).
Goto et al., *Virology*, 238:265 (1997).
Grambas et al., *Virology*. 190:541 (1992).
Hagen et al., *J. Virol.*, 68:1509 (1994).
Hatta et al., *Science*, 293:1840 (2001).
Hay et al., (eds) *Options for the control of influenza II*. Excerpta Medica, Amsterdam, pp. 281-288 (1993).
Hay et al., *EMBO J.*, 4:3021 (1985).
Helenius, *Cell*, 69:577 (1992).
Herlocher et al., *Proc. Natl. Acad. Sci. USA*. 90:6032 (1993).
Holsinger et al., *J. Virol.*, 68:1551 (1994).
Horimoto et al., *J. Virol.*, 68:3120 (1994).
Horimoto et al., *Virology*, 206:755 (1995).
Horimoto et al., *Virology*, 213:223 (1995).
Ilyushina et al., *Virology*, 341:102 (2005).
Iwatsuki-Horimoto et al., *J. Virol.*, 80:5233 (2006).
Kato et al., *Virology*, 37:632 (1969).
Katz et al., *J. Virol.*, 64:1808 (1990).
Kawaoka et al., *Virology*, 139:303 (1984).
Keitel et al., in *Textbook of Influenza*, eds. Nickolson, K. G., Webster, R. G., and Hay, A. (Blackwell. Oxford), pp. 373-390 (1998).
Kida et al., *Virology*, 122:38 (1982).
Klenk et al., *Trends Microbiol.*, 2:39 (1994).
Klimkait et al., *J. Virol.* 64:621 (1990).
Lamb et al., *Cell*, 40:627 (1985).
Lamb et al., In Fields, B. N., Knipe, D. M., and Howley, P. M. (eds) *Fields Virology* 3rd ed. Lippincott-Raven Publishers, Philadelphia, Pa., pp. 1353-1395 (1996).
Le et al., *Nature*, 437:1108 (2005).
Leahy et al., *J. Virol.*, 71:8347 (1997).
Leahy et al., *J. Virol.*, 71:8352 (1997).
Leahy et al., *J. Virol.*, 72:2305 (1998).
Li et al., *Nature*, 430:209 (2004).
Li et al., *Virus Res.*, 37:153 (1995).
Lin et al., *Lancet*, 368:991 (2006).
Luytjes et al., *Cell*, 59:1107 (1989).
Maassab et al., *Rev. Med. Virol.*, 9:237 (1991).
Martin et al., *Cell*, 67:117 (1991).
McCown et al., *J. Virol.*, 79:3595 (2005).
McCown et al., *J. Virol.*, 80:8178 (2006).
Mena et al., *J. Virol.*, 70:5016 (1996).

Neirynck et al., *Nat. Med.*, 5:1157 (1999).
Neumann et al., *J. Virol.*, 71:9690 (1997).
Neumann et al., *Proc. Natl. Acad. Sci. USA*, 96:9345 (1999).
Neumann et al., *Virology*, 202:477 (1994).
Nicholson et al., *Lancet* 357:1937 (2001).
Niwa et al., *Gene*, 108:193 (1991).
Ochman et al., *Genetics*, 12:621 (1988).
Ohuchi et al., *J. Virol.*, 68:920 (1994).
Perez et al., *Virology*, 249:52 (1998).
Piller et al., *Proc. Natl. Acad. Sci. USA*, 93:111 (1996).
Pinto et al., *Cell*, 69:517 (1992).
Pleschka et al., *J. Virol.*, 70:4188 (1996).
Puthavathana et al., *J. Gen. Virol.*, 86:423 (2005).
Rogers et al., *Virology*, 173:317 (1989).
Rogers et al., *Virology* 127:361 (1983).
Roizman et al., (eds) *Fields Virology*, 3rd ed. Lippincott-Raven Publishers, Philadelphia, Pa., pp. 101-111 (1996).
Sansom et al., *Protein En.*, 6:65 (1993).
Schnell et al., *EMBO J.*, 13:4195 (1994).
Schubert et al., *FEBS Lett.*, 398:12 (1996).
Schubert et al., *J. Virol.*, 69:7699 (1995).
Sears et al., *J. Infect. Dis.*, 158:1209 (1988).
Senne et al., *Avian Dis.*, 40:425 (1996).
Skehel et al., *J. Gen. Virol*, 38:97 (1978).
Steinhauer, *Viroloy*, 258:1 (1999).
Steinhoff et al., *J. Infect. Dis.*, 162:394 (1990).
Steinhoff et al., *J. Infect. Dis.*, 163:1023 (1991).
Stephenson et al., *Vaccine*, 21:1687 (2003).
Stieneke-Grober et al., *EMBO J.*, 11:2407 (1992).
Strebel et al., *J. Virol.*, 63:3784 (1989).
Strebel et al., *Science*, 241:1221 (1988).
Suarez et al., *J. Virol.*, 72:6678 (1998).
Subbarao et al., *J. Virol.*, 67:7223 (1993).
Subbarao et al., *Science*, 279:393 (1998).
Sugrue et al., *EMBO J.*, 9:3469 (1990).
Sugrue et al., *Virology*, 180:617 (1991).
Suguitan et al., *PLoS Med.*, 2:e360 (2006).
Sunstrom et al., *J. Membr. Biol.*, 150:127 (1996).
Takada et al., *Vaccine*, 21:3212 (2003).
Takeuchi et al., *J. Virol.*, 68:911 (1994).
Talon et al., *Proc. Natl. Acad. Sci. USA*, 97:4309 (2000).
Terwilliger et al., *Proc. Natl. Acad. Sci. USA*, 86:5163 (1989).
Treanor et al., *N. Engl. J. Med.*, 354:1343 (2006).
Wang et al., *J. Virol.*, 67:5585 (1993).
Weber et al., *Arch. Virol*, 142:1029 (1997).
Weber et al., *J. Virol.*, 70:8361 (1996).
Wharton et al., *EMBO J.*, 14, 240-246 (1995).
World Health Organization. 2006. Avian influenza A (H5N1). *Wkly. Epidemiol. Rec.*, 81:249-260.
Yamada et al., *Nature*, 444:378 (2006).
Yang et al., *Science*, 317:825 (2007).
Yasuda et al., *J. Virol.*, 68:8141 (1994).
Zebedee et al., *J. Virol.*, 56:502 (1985).
Zebedee et al., *J. Virol.*, 62:2762 (1988).
Zhimov et al. *J. Gen. Virol.*, 65:1127 (1984).
Zhimov, *Virology*, 176:274 (1990).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An immunogenic composition comprising an isolated, live, in vivo attenuated recombinant influenza virus comprising a PA viral gene segment, a PB1 viral gene segment, a PB2 viral gene segment, a HA viral gene segment, a NA viral gene segment, a NP viral gene segment, a M viral gene segment having coding sequences for M1 and M2, and a NS viral gene segment having coding sequences for NS1 and NS2, wherein the M gene segment comprises a mutant M2 protein gene for a M2 protein which has a deletion consisting of 2 to 21 residues of the C-terminus of the cytoplasmic tail which M2 protein is encoded by the mutant M2 protein gene, wherein the deletion attenuates the replication of the recombinant virus in vivo relative to the corresponding influenza virus without the deletion, wherein the amount of the virus in the composition is about 0.1 micrograms to 200 micrograms of influenza virus hemagglutinin (HA) per influenza virus isolate or about $10^3$ to $10^7$ PFU per influenza virus isolate.

2. The immunogenic composition of claim 1, wherein the recombinant virus comprises influenza A HA.

3. The immunogenic composition of claim 2, wherein the recombinant virus comprises H5 HA.

4. The immunogenic composition of claim 2, wherein the HA is not H1 or H3 HA.

5. The immunogenic composition of claim 1, wherein the HA in the recombinant virus is modified at the HA cleavage site so that in vitro plaque formation occurs only in the presence of trypsin relative to an unmodified HA cleavage site where in vitro plaque formation occurs in the absence of trypsin.

6. The immunogenic composition of claim 1, wherein the recombinant virus further comprises an additional attenuating mutation.

7. The immunogenic composition of claim 1, further comprising at least one different influenza virus.

8. The immunogenic composition of claim 1, wherein 2 up to 7 C-terminal residues of the cytoplasmic tail of M2 are deleted.

9. The immunogenic composition of claim 1, wherein 9 up to 21 C-terminal residues of the cytoplasmic tail of M2 are deleted.

10. The immunogenic composition of claim 1, further comprising a pharmaceutically acceptable carrier.

11. The immunogenic composition of claim 1, wherein the mutant M2 protein gene has a mutation that codes for a deletion of 5 to 15 residues from the C-terminus of the M2 protein.

12. The immunogenic composition of claim 11, wherein the recombinant influenza virus has a HA gene segment for a H5 HA with an HA cleavage site of an avirulent influenza virus.

13. A method to raise an immune response against influenza virus in a vertebrate, comprising:
    contacting the vertebrate with the immunogenic composition of claim 1.

14. The method of claim 13, wherein the vertebrate is an avian or a mammal.

15. The method of claim 14, wherein the mammal is a human.

16. The method of claim 13, wherein 2 up to 7 C-terminal residues of the cytoplasmic tail of M2 are deleted.

17. The method of claim 13, wherein 9 up to 21 C-terminal residues of the cytoplasmic tail of M2 are deleted.

18. The method of claim 13, wherein the recombinant virus further comprises an additional attenuating mutation.

19. The method of claim 13, wherein the recombinant virus comprises H5 HA.

20. The method of claim 13, wherein the HA of the recombinant virus is not H1 or H3 HA.

* * * * *